US011013730B1

(12) United States Patent
Holmgren et al.

(10) Patent No.: US 11,013,730 B1
(45) Date of Patent: *May 25, 2021

(54) COMPOSITION COMPRISING SELENAZOL OR THIAZALONE DERIVATIVES AND SILVER AND METHOD OF TREATMENT THEREWITH

(71) Applicant: Thioredoxin Systems AB, Stockholm (SE)

(72) Inventors: Arne Holmgren, Stockholm (SE); Jun Lu, Stockholm (SE)

(73) Assignee: Thioredoxin Systems AB, Sollentuna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,847

(22) Filed: Aug. 27, 2018

Related U.S. Application Data

(63) Continuation of application No. 14/850,567, filed on Sep. 10, 2015, now Pat. No. 10,058,542.

(60) Provisional application No. 62/049,824, filed on Sep. 12, 2014.

(51) Int. Cl.
| | |
|---|---|
| *A61K 31/41* | (2006.01) |
| *A61K 31/437* | (2006.01) |
| *A61K 31/44* | (2006.01) |
| *A61K 31/4439* | (2006.01) |
| *A61K 31/444* | (2006.01) |
| *C12Q 1/18* | (2006.01) |
| *A61K 33/38* | (2006.01) |

(52) U.S. Cl.
CPC ............ *A61K 31/444* (2013.01); *A61K 31/41* (2013.01); *A61K 31/437* (2013.01); *A61K 31/44* (2013.01); *A61K 31/4439* (2013.01); *A61K 33/38* (2013.01); *C12Q 1/18* (2013.01); *Y02A 50/30* (2018.01)

(58) Field of Classification Search
CPC .... A61K 31/444; A61K 31/437; A61K 31/41; A61K 31/44; A61K 31/4439; A61K 33/38; C12Q 1/18
See application file for complete search history.

(56) References Cited

U.S. PATENT DOCUMENTS

| | | |
|---|---|---|
| 3,491,500 A | 1/1970 | Fischer et al. |
| 3,945,662 A | 3/1976 | Murase et al. |
| 3,975,155 A | 8/1976 | Geyer |
| 4,110,378 A | 8/1978 | Geyer |
| 4,150,026 A | 4/1979 | Miller et al. |
| 4,156,729 A | 5/1979 | Boshagen et al. |
| 4,190,663 A | 2/1980 | Boshagen et al. |
| 4,244,966 A | 1/1981 | Lippman et al. |
| 4,352,799 A | 10/1982 | Renson et al. |
| 4,397,858 A | 8/1983 | Welter et al. |
| 4,418,069 A | 11/1983 | Welter et al. |
| 4,454,068 A | 6/1984 | Welter et al. |
| 4,550,168 A | 10/1985 | Welter et al. |
| 4,599,605 A | 7/1986 | Froeb et al. |
| 4,602,011 A | 7/1986 | West et al. |
| 4,606,909 A | 8/1986 | Bechgaard et al. |
| 4,618,669 A | 10/1986 | Dereu et al. |
| 4,711,961 A | 12/1987 | Welter et al. |
| 4,730,053 A | 3/1988 | Dereu et al. |
| 4,751,309 A | 6/1988 | Daltrozzo et al. |
| 4,757,063 A | 7/1988 | Parnham |
| 4,766,113 A | 8/1988 | West et al. |
| 4,774,252 A | 9/1988 | Welter et al. |
| 4,778,814 A | 10/1988 | Cash |
| 4,778,815 A | 10/1988 | Cash |
| 4,784,994 A | 11/1988 | Romer et al. |
| 4,873,350 A | 10/1989 | Welter et al. |
| 4,876,347 A | 10/1989 | Daltrozzo et al. |
| 4,906,466 A | 3/1990 | Edwards et al. |
| 4,910,313 A | 3/1990 | Welter et al. |
| 4,932,948 A | 6/1990 | Kernes et al. |
| 4,940,134 A | 7/1990 | Aoki et al. |
| 4,960,890 A | 10/1990 | Daltrozzo et al. |
| 5,008,394 A | 4/1991 | Gunther et al. |
| 5,021,242 A | 6/1991 | Romer et al. |
| 5,114,954 A | 5/1992 | Biedermann et al. |
| 5,128,339 A | 7/1992 | Dunlap et al. |
| 5,223,525 A | 6/1993 | Wu et al. |
| 5,225,418 A | 7/1993 | Miller |
| 5,246,951 A | 9/1993 | Galet et al. |
| 5,250,696 A | 10/1993 | Dunlap et al. |
| 5,288,595 A | 2/1994 | Watanabe et al. |
| 5,288,734 A | 2/1994 | Hager et al. |
| 5,306,818 A | 4/1994 | Subramanyam et al. |
| 5,364,649 A | 11/1994 | Rossmoore et al. |
| 5,368,864 A | 11/1994 | Lahr et al. |
| 5,385,726 A | 1/1995 | Baldew et al. |
| 5,393,756 A | 2/1995 | Miller |
| 5,449,593 A | 9/1995 | Morigaki et al. |
| 5,460,829 A | 10/1995 | Bobee et al. |
| 5,480,888 A | 1/1996 | Kodama et al. |
| 5,480,898 A | 1/1996 | Lindner |
| 5,512,589 A | 4/1996 | Dunlap et al. |
| 5,543,300 A | 8/1996 | Inglot et al. |
| 5,576,151 A | 11/1996 | Morigaki et al. |
| 5,580,713 A | 12/1996 | Hara et al. |
| 5,597,841 A | 1/1997 | Dunlap et al. |
| 5,609,883 A | 3/1997 | Valentine et al. |
| 5,618,845 A | 4/1997 | Grebow et al. |
| 5,683,863 A | 11/1997 | Bergthaller et al. |
| 5,714,507 A | 2/1998 | Valcke et al. |
| 5,736,591 A | 4/1998 | Dunn |
| 5,738,872 A | 4/1998 | Ortyl et al. |
| 5,804,591 A | 9/1998 | Valcke et al. |

(Continued)

FOREIGN PATENT DOCUMENTS

| | | |
|---|---|---|
| JP | 2000256335 | 9/2000 |
| JP | 200086508 | 12/2000 |

(Continued)

*Primary Examiner* — Alma Pipic
(74) *Attorney, Agent, or Firm* — Hoffberg & Associates; Steven M. Hoffberg

(57) ABSTRACT

A method for treating a prokaryotic infection in an animal or human by administering a pharmaceutically acceptable composition, comprising administering a source of silver ions and a benzoisoselenazol derivative, e.g., an ebselen derivative.

19 Claims, 11 Drawing Sheets

(56) References Cited

U.S. PATENT DOCUMENTS

| | | | |
|---|---|---|---|
| 5,855,912 | A | 1/1999 | Ortyl et al. |
| 5,888,526 | A | 3/1999 | Tsubai et al. |
| 5,932,247 | A | 8/1999 | Ortyl et al. |
| 5,948,800 | A | 9/1999 | Maruyama et al. |
| 5,965,150 | A | 10/1999 | Wada et al. |
| 5,968,920 | A | 10/1999 | Erdelmeier et al. |
| 5,973,009 | A | 10/1999 | Tailhan-Lomont et al. |
| 6,001,825 | A | 12/1999 | Xu et al. |
| 6,039,974 | A | 3/2000 | MacLaren et al. |
| 6,040,328 | A | 3/2000 | Tailhan-Lomont et al. |
| 6,057,310 | A | 5/2000 | Xu et al. |
| 6,093,532 | A | 7/2000 | Erdelmeier et al. |
| 6,099,834 | A | 8/2000 | Stanley |
| 6,113,942 | A | 9/2000 | Ortyl et al. |
| 6,130,212 | A | 10/2000 | Xu et al. |
| 6,130,254 | A | 10/2000 | Fisher et al. |
| 6,224,910 | B1 | 5/2001 | Ullah et al. |
| 6,248,806 | B1 | 6/2001 | Codolar et al. |
| 6,306,851 | B1 | 10/2001 | Santilli et al. |
| 6,319,912 | B1 | 11/2001 | Grubb et al. |
| 6,329,416 | B1 | 12/2001 | Grubb et al. |
| RE37,516 | E | 1/2002 | Grebow et al. |
| 6,335,036 | B1 | 1/2002 | Nakagami et al. |
| 6,339,098 | B1 | 1/2002 | Collins et al. |
| 6,342,510 | B1 | 1/2002 | Isakson et al. |
| 6,344,218 | B1 | 2/2002 | Dodd et al. |
| 6,355,648 | B1 | 3/2002 | Fensome et al. |
| 6,358,947 | B1 | 3/2002 | Zhi et al. |
| 6,358,948 | B1 | 3/2002 | Zhang et al. |
| 6,365,630 | B1 | 4/2002 | Fisher et al. |
| 6,369,056 | B1 | 4/2002 | Zhang et al. |
| 6,380,178 | B1 | 4/2002 | Grubb et al. |
| 6,380,235 | B1 | 4/2002 | Zhang et al. |
| 6,391,907 | B1 | 5/2002 | Fensome et al. |
| 6,399,593 | B1 | 6/2002 | Grubb et al. |
| 6,407,083 | B1 | 6/2002 | Xu et al. |
| 6,407,101 | B1 | 6/2002 | Collins et al. |
| 6,417,214 | B1 | 7/2002 | Ullrich et al. |
| 6,423,699 | B1 | 7/2002 | Grubb et al. |
| 6,436,929 | B1 | 8/2002 | Zhang et al. |
| 6,441,019 | B2 | 8/2002 | Santilli et al. |
| 6,444,668 | B1 | 9/2002 | Grubb et al. |
| 6,444,726 | B1 | 9/2002 | Brunt et al. |
| 6,454,813 | B1 | 9/2002 | Chan |
| 6,461,386 | B1 | 10/2002 | Chan et al. |
| 6,462,032 | B1 | 10/2002 | Grubb et al. |
| 6,495,517 | B2 | 12/2002 | Tanaka |
| 6,498,154 | B1 | 12/2002 | Grubb et al. |
| 6,503,939 | B2 | 1/2003 | Grubb et al. |
| 6,509,334 | B1 | 1/2003 | Zhang et al. |
| 6,521,657 | B2 | 2/2003 | Fensome et al. |
| 6,525,040 | B1 | 2/2003 | Erdelmeier et al. |
| 6,528,467 | B1 | 3/2003 | Takemura et al. |
| 6,544,970 | B2 | 4/2003 | Grubb et al. |
| 6,562,857 | B2 | 5/2003 | Collins et al. |
| 6,566,358 | B2 | 5/2003 | Zhang et al. |
| 6,583,145 | B1 | 6/2003 | Fensome et al. |
| 6,601,580 | B1 | 8/2003 | Bloch et al. |
| 6,608,068 | B2 | 8/2003 | Fensome et al. |
| 6,617,345 | B1 | 9/2003 | Gregory et al. |
| 6,641,829 | B1 | 11/2003 | Green et al. |
| 6,656,456 | B2 | 12/2003 | Dodd et al. |
| 6,673,828 | B1 | 1/2004 | Green et al. |
| 6,683,036 | B1 | 1/2004 | Foley et al. |
| 6,693,103 | B2 | 2/2004 | Zhang et al. |
| 6,710,017 | B2 | 3/2004 | Unhoch et al. |
| 6,713,478 | B2 | 3/2004 | Zhang et al. |
| 6,723,692 | B2 | 4/2004 | Foley et al. |
| 6,727,057 | B2 | 4/2004 | Suzuki et al. |
| 6,733,113 | B2 | 5/2004 | Yoshizawa et al. |
| 6,740,628 | B2 | 5/2004 | Bennie et al. |
| 6,750,187 | B2 | 6/2004 | Alam et al. |
| 6,759,408 | B2 | 7/2004 | Grubb et al. |
| 6,794,373 | B2 | 9/2004 | Grubb et al. |
| 6,800,427 | B2 | 10/2004 | Yamane |
| 6,811,711 | B2 | 11/2004 | Unhoch et al. |
| 6,815,459 | B2 | 11/2004 | Ko et al. |
| 6,835,744 | B2 | 12/2004 | Ullrich et al. |
| 6,841,568 | B2 | 1/2005 | Fensome et al. |
| 6,908,962 | B1 | 6/2005 | Frankenbach et al. |
| 6,927,199 | B2 | 8/2005 | Takemura et al. |
| 6,935,334 | B2 | 8/2005 | Bloch et al. |
| 6,942,870 | B2 | 9/2005 | Fisher et al. |
| 6,946,454 | B2 | 9/2005 | Fensome et al. |
| 6,949,654 | B2 | 9/2005 | Oh et al. |
| 6,982,261 | B2 | 1/2006 | Collins et al. |
| 6,984,636 | B2 | 1/2006 | Murphy et al. |
| 7,008,531 | B2 | 3/2006 | Unhoch et al. |
| 7,008,990 | B2 | 3/2006 | Raether et al. |
| 7,022,823 | B2 | 4/2006 | Nomura et al. |
| 7,081,457 | B2 | 7/2006 | Zhang et al. |
| 7,083,906 | B2 | 8/2006 | Suzuki et al. |
| 7,084,168 | B2 | 8/2006 | Fensome et al. |
| 7,087,107 | B2 | 8/2006 | Tateishi et al. |
| 7,091,234 | B2 | 8/2006 | Fensome et al. |
| 7,097,701 | B2 | 8/2006 | Tateishi et al. |
| 7,098,174 | B2 | 8/2006 | Takemura et al. |
| 7,109,189 | B2 | 9/2006 | Murphy et al. |
| 7,112,602 | B2 | 9/2006 | D'Amato et al. |
| 7,118,761 | B2 | 10/2006 | Canada et al. |
| 7,118,844 | B2 | 10/2006 | Fujita et al. |
| 7,129,021 | B2 | 10/2006 | Noglik et al. |
| 7,132,012 | B2 | 11/2006 | Tateishi et al. |
| 7,141,599 | B2 | 11/2006 | Gregory et al. |
| 7,211,134 | B2 | 5/2007 | Tateishi et al. |
| 7,217,429 | B2 | 5/2007 | Garcia et al. |
| 7,219,988 | B2 | 5/2007 | Hanaki et al. |
| 7,244,865 | B2 | 7/2007 | Liang |
| 7,253,203 | B2 | 8/2007 | Fensome et al. |
| 7,264,951 | B1 | 9/2007 | Bringi et al. |
| 7,268,148 | B2 | 9/2007 | Voorhees et al. |
| 7,291,449 | B2 | 11/2007 | Nakamura et al. |
| 7,316,738 | B2 | 1/2008 | Richardson et al. |
| 7,345,008 | B1 | 3/2008 | Suzuki et al. |
| 7,351,838 | B2 | 4/2008 | Benson et al. |
| 7,426,948 | B2 | 9/2008 | Richardson et al. |
| 7,488,822 | B2 | 2/2009 | Zhang et al. |
| 7,495,019 | B2 | 2/2009 | Zeng |
| 7,527,683 | B2 | 5/2009 | Kawakami et al. |
| 7,569,564 | B2 | 8/2009 | Zhang et al. |
| 7,579,389 | B2 | 8/2009 | Ong |
| 7,585,980 | B2 | 9/2009 | Lindner |
| 7,601,355 | B2 | 10/2009 | Howard et al. |
| 7,635,491 | B2 | 12/2009 | Forceville et al. |
| 7,645,761 | B2 | 1/2010 | Fensome et al. |
| 7,648,943 | B2 | 1/2010 | Fujiwara et al. |
| 7,651,990 | B2 | 1/2010 | Asmus |
| 7,666,858 | B2 | 2/2010 | Palma |
| 7,667,046 | B2 | 2/2010 | Benson et al. |
| 7,671,155 | B2 | 3/2010 | Shah et al. |
| 7,671,211 | B1 | 3/2010 | Holmgren et al. |
| 7,776,925 | B2 | 8/2010 | Stamler et al. |
| 7,790,905 | B2 | 9/2010 | Tawa et al. |
| 7,820,829 | B2 | 10/2010 | Zeng |
| 7,824,557 | B2 | 11/2010 | Whitekettle et al. |
| 7,846,924 | B2 | 12/2010 | Collins et al. |
| 7,884,037 | B2 | 2/2011 | Sirovatka et al. |
| 7,884,064 | B2 | 2/2011 | Bernhardt et al. |
| 7,888,514 | B2 | 2/2011 | Lindner |
| 7,923,434 | B2 | 4/2011 | Davioud-Charvet et al. |
| 7,927,613 | B2 | 4/2011 | Almarsson et al. |
| 7,932,230 | B2 | 4/2011 | McDaniel |
| 7,939,500 | B2 | 5/2011 | McDaniel |
| 7,951,232 | B2 | 5/2011 | Zullo et al. |
| 7,988,982 | B2 | 8/2011 | Andre et al. |
| 7,998,653 | B2 | 8/2011 | O'Donoghue et al. |
| 8,022,162 | B2 | 9/2011 | Maton et al. |
| 8,067,519 | B2 | 11/2011 | Maton et al. |
| 8,076,411 | B2 | 12/2011 | Maton et al. |
| 8,084,535 | B2 | 12/2011 | Maton et al. |
| 8,101,200 | B2 | 1/2012 | Whitbourne et al. |
| 8,119,684 | B2 | 2/2012 | Yeh et al. |
| 8,129,328 | B2 | 3/2012 | Bernhardt et al. |
| 8,129,408 | B2 | 3/2012 | Ortyl et al. |

(56) References Cited

U.S. PATENT DOCUMENTS

| | | |
|---|---|---|
| 8,188,088 B2 | 5/2012 | Stierli et al. |
| 8,222,283 B2 | 7/2012 | Yoshida et al. |
| 8,273,685 B2 | 9/2012 | Dairiki et al. |
| 8,309,612 B2 | 11/2012 | Hirai et al. |
| 8,313,760 B2 | 11/2012 | Hunter et al. |
| 8,329,690 B2 | 12/2012 | Zhang et al. |
| 8,338,143 B2 | 12/2012 | Bringi et al. |
| 8,338,358 B2 | 12/2012 | Bernhardt et al. |
| 8,343,437 B2 | 1/2013 | Patel |
| 8,343,536 B2 | 1/2013 | Bates et al. |
| 8,344,087 B2 | 1/2013 | Maton et al. |
| 8,349,353 B2 | 1/2013 | Lichter et al. |
| 8,350,049 B2 | 1/2013 | Lindner |
| 8,372,869 B2 | 2/2013 | Billack et al. |
| 8,415,419 B2 | 4/2013 | Yamasaki et al. |
| 8,420,595 B2 | 4/2013 | Kopke et al. |
| 8,425,880 B1 | 4/2013 | Lyczak et al. |
| 8,426,452 B2 | 4/2013 | Billack et al. |
| 8,466,146 B2 | 6/2013 | Zhang et al. |
| 8,470,815 B2 | 6/2013 | Saulnier Sholler et al. |
| 8,476,262 B2 | 7/2013 | Collins et al. |
| 8,496,952 B2 | 7/2013 | Falk et al. |
| 8,496,957 B2 | 7/2013 | Lichter et al. |
| 8,524,796 B2 | 9/2013 | Kim et al. |
| 8,536,207 B2 | 9/2013 | Yoshida et al. |
| 8,575,122 B2 | 11/2013 | Lichter et al. |
| 8,580,308 B2 | 11/2013 | Heacock et al. |
| 8,592,468 B2 | 11/2013 | Holmgren et al. |
| 8,609,702 B2 | 12/2013 | Zeng |
| 8,648,119 B2 | 2/2014 | Lichter et al. |
| 8,673,367 B2 | 3/2014 | Weibeta et al. |
| 8,685,372 B2 | 4/2014 | Tsien et al. |
| 8,784,870 B2 | 7/2014 | Lichter et al. |
| 8,846,770 B2 | 9/2014 | Lichter et al. |
| 8,877,204 B2 | 11/2014 | Srivastava et al. |
| 8,895,610 B1 | 11/2014 | Kay |
| 8,901,158 B2 | 12/2014 | Churchill et al. |
| 9,023,805 B2 | 5/2015 | Hausheer |
| 9,066,855 B2 | 6/2015 | Lichter et al. |
| 9,072,773 B2 | 7/2015 | Gonzalez et al. |
| 9,085,598 B2 | 7/2015 | Alaoui-Jamali et al. |
| 9,132,087 B2 | 9/2015 | Lichter et al. |
| 9,220,714 B2 | 12/2015 | Saulnier Sholler et al. |
| 9,320,760 B2 | 4/2016 | Hausheer |
| 9,566,348 B2 | 2/2017 | Srivastava et al. |
| 10,058,542 B1 * | 8/2018 | Holmgren |
| 2001/0021704 A1 | 9/2001 | Ghyczy et al. |
| 2001/0027176 A1 | 10/2001 | Tanaka |
| 2001/0046946 A1 | 11/2001 | Unhoch et al. |
| 2002/0035051 A1 | 3/2002 | Alam et al. |
| 2002/0037817 A1 | 3/2002 | Foley et al. |
| 2002/0037822 A1 | 3/2002 | Foley et al. |
| 2002/0039982 A1 | 4/2002 | Foley et al. |
| 2002/0058216 A1 | 5/2002 | Nakamura et al. |
| 2002/0106339 A1 | 8/2002 | Fisher et al. |
| 2002/0107238 A1 * | 8/2002 | Bandyopadhyay |
| 2002/0123443 A1 | 9/2002 | Bennie et al. |
| 2002/0142931 A1 | 10/2002 | DeNome et al. |
| 2002/0169090 A1 | 11/2002 | Foley et al. |
| 2002/0176879 A1 | 11/2002 | Dodd et al. |
| 2002/0183222 A1 | 12/2002 | Foley et al. |
| 2003/0032569 A1 | 2/2003 | Takemura et al. |
| 2003/0043238 A1 | 3/2003 | Yoshizawa et al. |
| 2003/0086916 A1 | 5/2003 | Goligorsky et al. |
| 2003/0170306 A1 | 9/2003 | Raether et al. |
| 2003/0189013 A1 | 10/2003 | Unhoch et al. |
| 2003/0198907 A1 | 10/2003 | Suzuki et al. |
| 2003/0202969 A1 | 10/2003 | Bloch et al. |
| 2003/0203136 A1 | 10/2003 | Takeuchi |
| 2003/0207217 A1 | 11/2003 | Suzuki et al. |
| 2003/0220337 A1 | 11/2003 | Ko et al. |
| 2003/0224303 A1 | 12/2003 | Toda |
| 2003/0232288 A1 | 12/2003 | Oka et al. |
| 2004/0002021 A1 | 1/2004 | Yamane |
| 2004/0005364 A1 | 1/2004 | Klein et al. |
| 2004/0029851 A1 | 2/2004 | Murphy et al. |
| 2004/0029934 A1 | 2/2004 | Ebihara et al. |
| 2004/0039180 A1 | 2/2004 | Nomura et al. |
| 2004/0045478 A1 | 3/2004 | Tateishi et al. |
| 2004/0047852 A1 | 3/2004 | Kennedy |
| 2004/0053888 A1 | 3/2004 | Suzuki et al. |
| 2004/0058952 A1 | 3/2004 | Kajiwara |
| 2004/0063021 A1 | 4/2004 | Fujita et al. |
| 2004/0067922 A1 | 4/2004 | Palma |
| 2004/0081911 A1 | 4/2004 | Noglik et al. |
| 2004/0147581 A1 | 7/2004 | Taylor et al. |
| 2004/0157763 A1 | 8/2004 | Foley et al. |
| 2004/0157848 A1 | 8/2004 | Maziasz |
| 2004/0175407 A1 | 9/2004 | McDaniel |
| 2004/0204471 A1 | 10/2004 | Seibert |
| 2004/0204472 A1 | 10/2004 | Briggs et al. |
| 2004/0220155 A1 | 11/2004 | Seibert |
| 2004/0235783 A1 | 11/2004 | Ghyczy et al. |
| 2004/0235950 A1 | 11/2004 | Voorhees et al. |
| 2004/0247655 A1 | 12/2004 | Asmus et al. |
| 2005/0004224 A1 | 1/2005 | Needleman |
| 2005/0014729 A1 | 1/2005 | Pulaski |
| 2005/0014789 A1 | 1/2005 | Andrews et al. |
| 2005/0014801 A1 | 1/2005 | Zeng |
| 2005/0036982 A1 | 2/2005 | Unhoch et al. |
| 2005/0058709 A1 | 3/2005 | Fisher et al. |
| 2005/0073563 A1 | 4/2005 | Hanaki et al. |
| 2005/0101563 A1 | 5/2005 | Pulaski et al. |
| 2005/0103709 A1 | 5/2005 | Takemura et al. |
| 2005/0107349 A1 | 5/2005 | Seibert |
| 2005/0107350 A1 | 5/2005 | Olson |
| 2005/0113409 A1 | 5/2005 | Connor et al. |
| 2005/0113427 A1 | 5/2005 | Goligorsky et al. |
| 2005/0119262 A1 | 6/2005 | Wax |
| 2005/0132927 A1 | 6/2005 | Tateishi et al. |
| 2005/0148612 A1 | 7/2005 | Stamler et al. |
| 2005/0163862 A1 | 7/2005 | Forceville et al. |
| 2005/0187172 A1 | 8/2005 | Masferrer |
| 2005/0187278 A1 | 8/2005 | Taylor |
| 2005/0215773 A1 | 9/2005 | Tateishi et al. |
| 2005/0222218 A1 | 10/2005 | Meier et al. |
| 2005/0227929 A1 | 10/2005 | Masferrer |
| 2005/0227957 A1 | 10/2005 | Murphy et al. |
| 2005/0233925 A1 | 10/2005 | Foley et al. |
| 2005/0277695 A1 | 12/2005 | Voorhees et al. |
| 2006/0009357 A1 | 1/2006 | Fujiwara et al. |
| 2006/0009494 A1 | 1/2006 | Voorhees et al. |
| 2006/0017792 A1 | 1/2006 | Tateishi et al. |
| 2006/0075921 A1 | 4/2006 | Richardson et al. |
| 2006/0084573 A1 | 4/2006 | Grech et al. |
| 2006/0086841 A1 | 4/2006 | Richardson et al. |
| 2006/0115440 A1 | 6/2006 | Arata et al. |
| 2006/0135569 A1 | 6/2006 | Wang et al. |
| 2006/0182701 A1 | 8/2006 | Gohla et al. |
| 2006/0268086 A1 | 11/2006 | Kawakami et al. |
| 2007/0014764 A1 | 1/2007 | Levy et al. |
| 2007/0021528 A1 | 1/2007 | Ong |
| 2007/0059255 A1 * | 3/2007 | Tichy |
| 2007/0123555 A1 | 5/2007 | Rao et al. |
| 2007/0142462 A1 | 6/2007 | Kennedy |
| 2007/0161609 A1 | 7/2007 | Buck et al. |
| 2007/0203239 A1 | 8/2007 | Gehenne et al. |
| 2007/0225255 A1 | 9/2007 | Frohlich et al. |
| 2007/0231295 A1 | 10/2007 | Hoppe et al. |
| 2007/0275945 A1 | 11/2007 | Lindner |
| 2008/0044399 A1 | 2/2008 | Levy |
| 2008/0070874 A1 | 3/2008 | Voorhees et al. |
| 2008/0108115 A1 | 5/2008 | Bringi et al. |
| 2008/0112909 A1 | 5/2008 | Faler et al. |
| 2008/0145664 A1 | 6/2008 | Sirovtka et al. |
| 2008/0146484 A1 | 6/2008 | Sirovtka et al. |
| 2008/0181950 A1 | 7/2008 | Bates et al. |
| 2008/0207679 A1 | 8/2008 | Berkowitz |
| 2008/0213608 A1 | 9/2008 | Richardson et al. |
| 2008/0213785 A1 | 9/2008 | Levy |
| 2008/0227766 A1 | 9/2008 | Wunder et al. |
| 2008/0234283 A1 | 9/2008 | Berkowitz |
| 2008/0241557 A1 | 10/2008 | Hoshi et al. |
| 2008/0241732 A1 | 10/2008 | Hosokawa et al. |

(56) References Cited

U.S. PATENT DOCUMENTS

| | | |
|---|---|---|
| 2008/0293777 A1 | 11/2008 | Erlanson et al. |
| 2008/0312365 A1 | 12/2008 | Maton et al. |
| 2008/0312366 A1 | 12/2008 | Maton et al. |
| 2008/0312367 A1 | 12/2008 | Maton et al. |
| 2009/0005422 A1 | 1/2009 | Holmgren et al. |
| 2009/0018110 A1 | 1/2009 | Levy et al. |
| 2009/0023103 A1 | 1/2009 | Toda |
| 2009/0039035 A1 | 2/2009 | Whitekettle et al. |
| 2009/0054390 A1 | 2/2009 | Levy et al. |
| 2009/0060973 A1 | 3/2009 | Hunter et al. |
| 2009/0074740 A1 | 3/2009 | Berkowitz et al. |
| 2009/0105313 A1 | 4/2009 | Yoshida et al. |
| 2009/0117204 A1 | 5/2009 | Zeng |
| 2009/0123567 A1 | 5/2009 | Zeng |
| 2009/0137617 A1 | 5/2009 | Levy |
| 2009/0143478 A1 | 6/2009 | Richardson et al. |
| 2009/0178211 A1 | 7/2009 | Wahl et al. |
| 2009/0178212 A1 | 7/2009 | Wahl et al. |
| 2009/0214606 A1 | 8/2009 | Bujard et al. |
| 2009/0215944 A1 | 8/2009 | Maton et al. |
| 2009/0220749 A1 | 9/2009 | O' Donoghue et al. |
| 2009/0239913 A1 | 9/2009 | Billack et al. |
| 2009/0246770 A1 | 10/2009 | Levy |
| 2009/0297533 A1 | 12/2009 | Lichter et al. |
| 2009/0301382 A1 | 12/2009 | Patel |
| 2009/0306225 A1 | 12/2009 | Lichter et al. |
| 2009/0318495 A1 | 12/2009 | Stierli et al. |
| 2009/0324552 A1 | 12/2009 | Lichter et al. |
| 2010/0003431 A1 | 1/2010 | Raybuck |
| 2010/0004225 A1 | 1/2010 | Lichter et al. |
| 2010/0008961 A1 | 1/2010 | Takeko |
| 2010/0015263 A1 | 1/2010 | Lichter et al. |
| 2010/0016198 A1 | 1/2010 | Bernhardt et al. |
| 2010/0021416 A1 | 1/2010 | Lichter et al. |
| 2010/0022661 A1 | 1/2010 | Lichter et al. |
| 2010/0041292 A1 | 2/2010 | Kim et al. |
| 2010/0075939 A1 | 3/2010 | Lindner |
| 2010/0081159 A1 | 4/2010 | Lebedeva et al. |
| 2010/0120873 A1 | 5/2010 | Hirai et al. |
| 2010/0184633 A1 | 7/2010 | Bernhardt et al. |
| 2010/0210745 A1 | 8/2010 | McDaniel et al. |
| 2010/0227899 A1* | 9/2010 | Billack |
| 2010/0231670 A1 | 9/2010 | Arai et al. |
| 2010/0233146 A1 | 9/2010 | McDaniel |
| 2010/0234402 A1 | 9/2010 | Dreyfuss et al. |
| 2010/0239679 A1 | 9/2010 | Greene et al. |
| 2010/0243221 A1 | 9/2010 | Yamasaki et al. |
| 2010/0260813 A1 | 10/2010 | Schnabel et al. |
| 2010/0273651 A1 | 10/2010 | Dietz et al. |
| 2010/0273864 A1 | 10/2010 | Lichter et al. |
| 2010/0280427 A1 | 11/2010 | Larsen et al. |
| 2010/0317515 A1 | 12/2010 | Dietz et al. |
| 2011/0009376 A1 | 1/2011 | Hirai et al. |
| 2011/0020914 A1 | 1/2011 | Abou-Nemeh |
| 2011/0024355 A1 | 2/2011 | Mansouri et al. |
| 2011/0039807 A1 | 2/2011 | Kim |
| 2011/0046088 A1 | 2/2011 | Worthington et al. |
| 2011/0052655 A1 | 3/2011 | Whitekettle et al. |
| 2011/0052656 A1 | 3/2011 | Whitekettle et al. |
| 2011/0070376 A1 | 3/2011 | Wales et al. |
| 2011/0086397 A1 | 4/2011 | Bringi et al. |
| 2011/0150956 A1 | 6/2011 | Lindner |
| 2011/0150961 A1 | 6/2011 | Perry et al. |
| 2011/0160055 A1 | 6/2011 | Ulmschneider et al. |
| 2011/0160056 A1 | 6/2011 | Ulmschneider et al. |
| 2011/0166020 A1 | 7/2011 | Renner et al. |
| 2011/0166021 A1 | 7/2011 | Ulmschneider et al. |
| 2011/0172095 A1 | 7/2011 | Dietz et al. |
| 2011/0172096 A1 | 7/2011 | Ulmschneider et al. |
| 2011/0172097 A1 | 7/2011 | Dietz et al. |
| 2011/0172098 A1 | 7/2011 | Dietz et al. |
| 2011/0172099 A1 | 7/2011 | Dietz et al. |
| 2011/0177147 A1 | 7/2011 | Hunter et al. |
| 2011/0177950 A1 | 7/2011 | Dietz et al. |
| 2011/0183842 A1 | 7/2011 | Dietz et al. |
| 2011/0190122 A1 | 8/2011 | Dietz et al. |
| 2011/0203018 A1 | 8/2011 | Gewehr et al. |
| 2011/0224170 A1 | 9/2011 | Wagner et al. |
| 2011/0240064 A1 | 10/2011 | Wales et al. |
| 2011/0250626 A1 | 10/2011 | Williams et al. |
| 2011/0257233 A1 | 10/2011 | Cosford et al. |
| 2011/0259571 A1 | 10/2011 | Yamasaki et al. |
| 2011/0274893 A1 | 11/2011 | Kaser et al. |
| 2011/0288013 A1 | 11/2011 | Levy |
| 2011/0288130 A1 | 11/2011 | Holmgren et al. |
| 2011/0301186 A1 | 12/2011 | Levy |
| 2011/0301235 A1 | 12/2011 | Erlanson et al. |
| 2012/0010103 A1 | 1/2012 | Brandli et al. |
| 2012/0016063 A1 | 1/2012 | Maton et al. |
| 2012/0021358 A1 | 1/2012 | Taguchi et al. |
| 2012/0045624 A1 | 2/2012 | Campbell et al. |
| 2012/0097194 A1 | 4/2012 | McDaniel et al. |
| 2012/0129955 A1 | 5/2012 | Bernhardt et al. |
| 2012/0148499 A1 | 6/2012 | Tsien et al. |
| 2012/0164203 A1 | 6/2012 | Premachandran et al. |
| 2012/0177713 A1 | 7/2012 | Weiss et al. |
| 2012/0211031 A1 | 8/2012 | Loeffler et al. |
| 2012/0232119 A1 | 9/2012 | Yoshida et al. |
| 2012/0258507 A1 | 10/2012 | Adams et al. |
| 2012/0258900 A1 | 10/2012 | Adams et al. |
| 2012/0309063 A1 | 12/2012 | Adams et al. |
| 2012/0328696 A1 | 12/2012 | Kim |
| 2013/0017582 A1 | 1/2013 | Bringi et al. |
| 2013/0045241 A1 | 2/2013 | Premachandran et al. |
| 2013/0115263 A1 | 5/2013 | Hunter et al. |
| 2013/0150239 A1 | 6/2013 | Premachandran et al. |
| 2013/0189516 A1 | 7/2013 | Sugino et al. |
| 2013/0202537 A1 | 8/2013 | Gonzalez et al. |
| 2013/0288985 A1 | 10/2013 | Jurkunas |
| 2013/0338105 A1 | 12/2013 | Worthington et al. |
| 2014/0004331 A1 | 1/2014 | Hida et al. |
| 2014/0018395 A1 | 1/2014 | Lichter et al. |
| 2014/0073030 A1 | 3/2014 | Jones et al. |
| 2014/0073548 A1 | 3/2014 | Jones et al. |
| 2014/0083324 A1 | 3/2014 | Wales et al. |
| 2014/0088149 A1 | 3/2014 | Holmgren et al. |
| 2014/0091031 A1 | 4/2014 | Mansouri et al. |
| 2014/0094449 A1 | 4/2014 | Churchill et al. |
| 2014/0135252 A1 | 5/2014 | Jones et al. |
| 2014/0142213 A1 | 5/2014 | Weiss et al. |
| 2014/0148339 A1 | 5/2014 | Smejkal et al. |
| 2014/0154808 A1 | 6/2014 | Patel |
| 2014/0182483 A1 | 7/2014 | Brandstadt et al. |
| 2014/0183398 A1 | 7/2014 | Brandstadt et al. |
| 2014/0187783 A1 | 7/2014 | Brandstadt et al. |
| 2014/0194627 A1 | 7/2014 | Brandstadt et al. |
| 2014/0243425 A1 | 8/2014 | Lichter et al. |
| 2014/0256659 A1 | 9/2014 | Alaoui-Jamali et al. |
| 2014/0329777 A1 | 11/2014 | Morici et al. |
| 2014/0364510 A1 | 12/2014 | Lichter et al. |
| 2015/0031712 A1 | 1/2015 | Rogosnitzky |
| 2015/0192564 A1 | 7/2015 | Lebedeva et al. |
| 2015/0313839 A1 | 11/2015 | Lichter et al. |
| 2015/0353604 A1 | 12/2015 | Gonzalez et al. |

FOREIGN PATENT DOCUMENTS

| | | |
|---|---|---|
| JP | 2000344663 | 12/2000 |
| JP | 6327431 | 9/2001 |
| JP | 6456615 | 9/2001 |
| JP | 63183528 | 9/2001 |
| JP | 2001261555 | 9/2001 |
| JP | 1131113 | 12/2015 |
| JP | 1131114 | 12/2015 |
| JP | 1132522 | 12/2015 |
| JP | 1135718 | 12/2015 |
| JP | 1180825 | 12/2015 |
| JP | 1294622 | 12/2015 |
| WO | WO1995027706 | 10/1995 |
| WO | WO9633712 | 10/1996 |
| WO | WO9726968 | 7/1997 |
| WO | WO9829417 | 7/1998 |
| WO | WO02053154 | 7/2002 |
| WO | WO02055076 | 7/2002 |

(56) References Cited

FOREIGN PATENT DOCUMENTS

| | | |
|---|---|---|
| WO | WO2007011773 | 1/2007 |
| WO | WO2008100628 | 8/2008 |
| WO | WO2008100629 | 8/2008 |
| WO | WO2008143879 | 11/2008 |
| WO | WO2008143883 | 11/2008 |
| WO | WO2008153906 | 12/2008 |
| WO | WO2008153908 | 12/2008 |
| WO | WO2009066299 | 5/2009 |
| WO | 2011/116355 A2 * | 9/2011 |

* cited by examiner

COMPOSITION COMPRISING SELENAZOL OR THIAZALONE DERIVATIVES AND SILVER AND METHOD OF TREATMENT THEREWITH

CROSS REFERENCE TO RELATED APPLICATIONS

The present application is a Continuation of U.S. patent application Ser. No. 14/850,567, filed Sep. 10, 2015, now U.S. Pat. No. 10,085,542, issued Aug. 28, 2018, which is a Non-provisional of, and claims benefit of priority from, U.S. Provisional Patent Application No. 62/049,824, filed Sep. 12, 2014, the entirety of which are expressly incorporated herein by reference.

FIELD OF THE INVENTION

The present invention deals with drugs and pharmaceutical compositions thereof for treatment or prevention of bacterial infections and prevention of bacterial biofilm of bacterial origin.

BACKGROUND OF THE INVENTION

The use of antibiotics for the treatment of infectious diseases is compromised due to the increase in the number of antibiotic-resistant bacterial strains. Thus, multi-resistant bacteria are a major health problem and the need for new antibiotics is apparent. In this invention a novel combination of silver ions with selenazol and thiazolone drugs targeting the thioredoxin system has been discovered. The strong synergistic effects observed will allow a wide range of bacteria to be targets of this new drug.

Thioredoxin

The thioredoxin (Trx) system and the GSH-glutaredoxin (Grx) system are two major thiol dependent disulfide reductases in the cells, which transfer the electrons from NADPH to their substrates (1-3). The two thiol dependent electron transferring pathways play critical roles in defense against oxidative stress by reducing methionine sulfoxide reductases (MSR) to repair proteins or peroxiredoxins (Prx) to remove peroxides. They are also electron donors for ribonucleotide reductase (RNR), which is essential for the production of deoxyribonucleotides and DNA (FIG. 6).

The thioredoxin (Trx), thioredoxin reductase (TrxR), and NADPH are together called the thioredoxin system, which serves as a hydrogen donor for ribonucleotide reductase and has a general powerful disulfide reductase activity (4, 5, 11, 13). The thioredoxin system is present in cells and in all forms of life (4, 5, 11, 13). Thioredoxin reductase (TrxR) is a dimeric FAD containing enzyme that catalyzes the reduction of its main protein substrate oxidized thioredoxin, to reduced thioredoxin at the expense of NADPH. The enzyme mechanism involves the transfer of reducing equivalents of NADPH to a redox active site disulfide via an FAD domain. Thioredoxin reductase from *Escherichia coli* with subunits of 35 kDa has been extensively characterized (46). X-ray crystal structure reveals that the active site disulfide is located in a buried position in the NADPH domain (22) and suggests that it should undergo a large conformational change to create a binding site for Trx-$S_2$ and reduction by a dithiol-disulfide exchange.

Trx system is composed with thioredoxin reductase (TrxR), Trx and NADPH. Trx is ubiquitous in all living organisms with its conserved CGPC active site and the Trx fold (1). In contrast, the TrxRs in mammalian cells and bacteria showed notable differences in structure and reaction mechanism (4-6). Bacteria have a smaller (70 kDa) sulfur-dependent enzyme whereas human and animal cells have a large (115 kDa) selenocysteine-containing enzyme (1-3,6). Moreover, many pathogenic bacteria contain distinct thiol-dependent redox systems (7). Particularly, some pathogenic bacteria lack glutathione (GSH) and glutaredoxin (Grx) and thus TrxR and Trx are essential for DNA synthesis and the Trx system should be a suitable target for development of antibacterial drugs (4, 8, 9).

Thioredoxin reductase is a ubiquitous enzyme present in all cells. However, the enzyme is often over-expressed in tumor cells compared to normal tissues, and tumor proliferation seems to be crucially dependent on an active thioredoxin system, making it a potential target for anticancer drugs (16). Over the last decade, a number small organic and organometallic molecules that include platinum and gold containing complexes (47-50), naphthoquinone spiroketal based natural products (51-53), different naphthazarin derivatives (54), certain nitrosoureas (55-56), and general thiol (or selenol) alkylating agents such as 4-vinylpyridine, iodoacetamide, or iodoacetic acid (57), have been identified as inhibitors of Trx or TrxR or both. Engman et al. have reported the inhibition of mammalian thioredoxin reductase by diaryldichalcogenides (58) and organotellurium compounds (59-61). However, no inhibition has been presented for bacterial TrxR.

Thioredoxins together with glutaredoxins are the two dithiol hydrogen donors for the essential enzyme ribonucleotide reductase required for DNA synthesis (FIG. 6) (4, 5). As shown in FIG. 6 the two enzymes glutathione reductase (GR encoded by the gor gene) and thioredoxin reductase (TrxR encoded by the trxB gene) in *E. coli* are central in electron transport from NADPH (6). Thioredoxin reductase from human and animal cells is a large selenoenzyme and very different from the enzymes present in all prokaryotes (7, 8). In contrast to the mammalian enzymes the *E. coli* enzyme is highly specific and utilizes a different mechanism with an involvement of protein conformation change as mentioned above (9).

Thioredoxin reductase (TrxR), catalyzes the electron donation from NADPH via thioredoxin (Trx) to ribonucleotide reductase (RNR) and may be essential for DNA synthesis if no other system is present. Cytosolic Trx is a highly conserved 12 kDa protein whereas the cytosolic TrxRs from mammalian and bacterial, e.g. *Escherichia coli*, are very different in their structure and catalytic mechanisms, with mammalian TrxR being a large selenoenzyme.

Ebselen, 2-phenyl-1,2-benzisoselenazol-3(2H)-one is an antioxidant and anti-inflammatory selenoorganic compound (1) used in clinical trials against e.g. stroke (2). It is thus known to be safely administered to humans. Ebselen and ebselen diselenide have been reported as substrates for mammalian thioredoxin reductase (3a) and its reaction mechanisms have been published (3b, 32). There are several reports of synthesis of substituted benzisoselenazol-3(2H)-ones. Some of these compounds were reported as inhibitors of viral cytopathogenicity and active immunostimulants inducing cytokines, such as interferons (IFNs), tumor necrosis factors (TNFs) and interleukin (IL-2) in human peripheral blood leukocytes (62-64). However, none of the reports indicates thioredoxin reductase activity.

It has been shown that ebselen, which has been known as a glutathione peroxidase (GSPx) mimic (1), is a substrate for human and mammalian thioredoxin reductase and a highly efficient oxidant of reduced thioredoxin (3a,3b). This strongly suggested that the thioredoxin system (NADPH, thioredoxin reductase and thioredoxin) is the primary target of ebselen, since a highly efficient reduction of hydroperoxides was given by ebselen in the presence of the thioredoxin system (3).

The cyclic-di-GMP (cdiGMP) signaling pathway regulates biofilm formation, motility, and pathogenesis. *Pseudomonas aeruginosa* is an important opportunistic pathogen that utilizes cdiGMP-regulated polysaccharides, including alginate and pellicle polysaccharide (PEL), to mediate virulence and antibiotic resistance. CdiGMP activates PEL and alginate biosynthesis by binding to specific receptors including PelD and Alg44. Ebselen was identified as an inhibitor of cdiGMP binding to receptors containing an RxxD domain including PelD and diguanylate cyclases (DGC). Ebselen reduces diguanylate cyclase activity by covalently modifying cysteine residues. Ebselen oxide, the selenone analogue of ebselen, also inhibits cdiGMP binding through the same covalent mechanism. Ebselen and ebselen oxide inhibit cdiGMP regulation of biofilm formation and flagella-mediated motility in *P. aeruginosa* through inhibition of diguanylate cyclases. Lieberman, O. J. et al., "High-Throughput Screening Using the Differential Radial Capillary Action of Ligand Assay Identifies Ebselen As an Inhibitor of Diguanylate Cyclases", ACS Biology 2014, 9, 183-192.

Ebselen and Derivatives

It was previously discovered that that ebselen [2-phenyl-1,2 benzisoselenazol-3(2H)-one], (EbSe) which is a substrate of mammalian TrxR and a competitive reversible inhibitor of bacterial TrxR, displays selective antibacterial activity toward certain bacteria lacking glutathione (48). The pathogenic bacteria including *Helicobacter pylori, Mycobacterium tuberculosis*, and *Staphyloccus aureus* exhibit high sensitivity to ebselen (48).

The thioredoxin (Trx), thioredoxin reductase (TrxR), and NADPH are together called the thioredoxin system, which serves as a hydrogen donor for ribonucleotide reductase and has the most general powerful disulfide reductase activity (4, 5, 11, 13). The thioredoxin system is present in cells and in all living systems (4, 5, 11, 13). Thioredoxin reductase (TrxR) is a dimeric FAD containing enzyme that catalyzes the reduction of its main protein substrate oxidized thioredoxin, to reduced thioredoxin at the expense of NADPH. The enzyme mechanism involves the transfer of reducing equivalents of NADPH to a redox active site disulfide via FAD domain. Thioredoxin reductase from *Escherichia coli* with subunits of 35 kDa has been extensively characterized (46). X-ray crystal structure reveals that the active site disulfide is located in a buried position in the NADPH domain (22), and suggests that it should undergo a large conformational change to create a binding site for Trx-Ω and reduction by a dithiol-disulfide exchange.

Thioredoxin reductase is a ubiquitous enzyme present in all living cells. However, the enzyme is often over-expressed in tumor cells compared to normal tissues, and tumor proliferation seems to be crucially dependent on an active thioredoxin system, making it a potential target for anticancer drugs. (16) Over the last decade, a number small organic and organometallic molecules that include platinum and gold containing complexes (47, 48, 49, 50), naphthoquinone spiroketal based natural products, (51, 52, 53) different naphthazarin derivatives (54), certain nitrosoureas (55, 56), and general thiol (or selenol) alkylating agents such as 4-vinylpyridine, iodoacetamide, or iodoacetic acid (57), have been identified as inhibitors of Trx or TrxR or both.

Engman et al. have reported the inhibition of thioredoxin reductase by diaryldichalcogenides (58) and organotellurium compounds (60, 61).

Ebselen and ebselen diselenide have been reported as substrates for mammalian thioredoxin reductase and its reaction mechanism (32, 77). Using glutathione as the reductant, the $H_2O_2$ reductase activity of ebselen was compared with that in the presence of the mammalian thioredoxin system. Formation of ebselen diselenide may serve as a dose-dependent storage form of ebselen, which can be relatively slowly activated to the catalytically active selenol by the mammalian thioredoxin system. The studies were extended to *E. coli* TrxR, and surprisingly, ebselen was found to inhibit *E. coli* TrxR. These findings lead to a search for the new organoselenium compounds containing the basic structure of ebselen, to study their reactivity with thioredoxin reductase.

There are several reports of synthesis of substituted benzisoselenazol-3(2H)-ones. Some of these compounds were reported as inhibitors of viral cytopathogenicity and active immunostimulants inducing cytokines, such as interferons (IFNs), tumor necrosis factors (TNFs) and interleukin (IL-2) in human peripheral blood leukocytes (62, 63, 64). 2-(4-caroboxyphenyl)benzisoselenazol-3(2H)-one was found to be potent and selective inhibitor of endothelial nitric oxide synthase (78). However, none of the reports indicates thioredoxin reductase activity.

Ebselen, a small isoselenazol drug well known for its antioxidant and anti-inflammatory properties, also has antibacterial properties. The mechanism has been unknown and there is a remarkable difference in sensitivity between *Staphyloccus aureus* being a 100-fold more sensitive than *E. coli* (10). The growth of methicillin resistant *Staphylococcus aureus* was shown to be inhibited by 0.20 µg per ml of ebselen, whereas strains of Enterobacteriaceae like *E. coli* NHHJ were much more resistant requiring up to 50 µg per ml. The MIC for 90% of *S. aureus* strains was 1.56 µg per ml and the drug was bacteriocidal (10).

Control of bacterial infection using chemotherapeutic principles and antibiotics are based on inhibition of cell wall synthesis, protein synthesis and other metabolic pathways. The presently used drugs have limitations and resistant bacterial infections is an increasing problem as evident by development of vancomycin and methicillin resistant bacteria. Since genetic material in the form of DNA is common to all microorganisms, inhibition of DNA synthesis is an attractive principle. In addition, drugs interrupting the defense of bacteria against oxidative stress should be a useful principle for developing new antibacterial agents.

The thioredoxin system, including thioredoxin (Trx), thioredoxin reductase (TrxR) and NADPH, is the most powerful protein disulfide reductase in cells (4, 5, 11-13). Together with the glutaredoxin system, including glutaredoxin (Grx), glutathione (GSH), glutathione reductase (GR) and NADPH, thioredoxins are important hydrogen donors of ribonucleotide reductase for DNA synthesis and play key roles in cell redox regulation and growth control (4-6, 12, 14).

Thioredoxin reductase is one of those few examples of enzymes where the same reaction is catalyzed by more than one structure and mechanism (9, 15). Extensive studies on the features and redox properties of TrxR from various organisms resulted in the classification of two TrxRs, one from higher eukaryotes with high molecular weight and structurally resembles the other oxidoreductases; the other from prokaryotes, fungi, and plants with low molecular weight and distinct in structures and catalytic mechanism.

Thus the striking difference between the enzymes would make them ultimate targets for novel antibiotic drug designs (16) although this has not yet been reported.

The TrxR from mammalian is a large selenoprotein with homodimer of 55 kD per subunits and a structure closely related to glutathione reductase but with an elongation containing a catalytically active selenol-thiol/selenosulfide in the conserved C-terminal sequence Gly-Cys(496)-Sec (497)-Gly, and thus a wide substrate specificity (7, 8, 15, 17-19). The bacterial counterpart of TrxR is however a non-selenoprotein with homodimer of 35 kD per subunits (9, 20, 21). Each E. coli TrxR monomer consists of an NADPH-binding domain and an FAD binding domain connected by a double-stranded ß-sheet. The active site Cys (135)-Ala-Thr-Cys(138) is located in the NADPH domain. A well-recognized characteristic of the E. coli enzyme is its large conformational change during catalysis. In its 3-D structure, the flow of electrons from NADPH to the active-site disulfide via the flavin can only be possible if the NADPH domain graphically rotating over 67° relative to the FAD domain, allowing an efficient hydride transfer from NADPH to FAD (the nicotinamide ring and the isoalloxazine would be in close contact) and simultaneously exposing the redox-active disulfide to the surface of the protein, accessible for the substrate (22, 23). Mammalian TrxRs are large dimeric selenoproteins ($M_r$ 114.000), with structures closely related to glutathione reductase, but with a C-terminal 16 amino acid elongation containing a unique catalytically active conserved sequence Gly-Cys-Sec-Gly. Mammalian thioredoxin reductases have a remarkably wide substrate specificity. E. coli TrxR is smaller (Mr 70.000/dimer), with the active-site Cys-Ala-Thr-Cys disulfide loop located in the NADPH domain. During catalysis, a large conformational change is required, i.e., from FO (flavin oxidation by disulfide) to FR (flavin reduction by NADPH) form as discussed above.

Ribonucleotide reductase is a universal enzyme, which for aerobic organisms supply all four deoxyribonucleotides required for DNA synthesis de novo, for either replication or repair (FIG. 6). Electrons for the reduction ultimately are from NADPH via either thioredoxin or glutaredoxin. These two small protein thiol electron donors are reduced by separate pathways. Thioredoxin is reduced by thioredoxin reductase, and glutaredoxin by the tripeptide glutathione (GSH), which is present in high millimolar concentrations in most cells. Oxidized glutathione (GSSG) is reduced by glutathione reductase.

Whereas, there are general overall similarities between thioredoxin, glutaredoxin and ribonucleotide reductase in bacteria and human and other mammalian cells, there are fundamental differences between thioredoxin reductase enzymes. Thus, the enzyme is by convergent evolution either low molecular weight specific enzymes like that in E. coli or other bacteria or a high molecular weight selenocysteine-containing enzyme with broad specificity like the three isozymes in human cells.

Ebselen, 2-phenyl-1,2-benzoisoselenazol-3(2H)-one, is an isoselenazol well known for its antioxidant and anti-inflammatory properties (1, 24) and is widely used in laboratories as peroxide reducing antioxidant in in vivo models and has been proved in clinical trials against acute ischemic stroke (2, 25-31). We have previously shown that ebselen and its diselenide are substrates for mammalian TrxR and efficient oxidants of reduced Trx forming the ebselen selenol, the active form of ebselen with its hydrogen peroxide reductase activity (3a,3b). The mechanism of antioxidant action of ebselen, together with its diselenide, was mainly through its interactions with the mammalian TrxR and Trx, providing the electrons for the reduction of hydrogen peroxide from NADPH (3a, 3b, 32). In the present invention we have discovered that ebselen, however, is not a substrate of E. coli TxrR, but instead it is a competitive inhibitor for the reduction of thioredoxin with a $K_i$ of 0.15 μM. E. coli mutants lacking a functional glutaredoxin system (glutathione reductase, GSH or glutaredoxin 1) were much more sensitive to inhibition by ebselen, which thereby will inhibit the essential enzyme ribonucleotide reductase (RNR) required for DNA synthesis. A main target of action of ebselen is the thioredoxin system. It follows that gram positive bacteria or other microorganisms lacking GSH will be particularly susceptible to ebselen. The present invention demonstrates that the well tolerated drug ebselen inhibits bacterial growth due to the large differences in structure and mechanism of the bacterial and mammalian thioredoxin reductases, establishing the drug as a novel chemotherapeutic principle.

It has been reported that ebselen inhibits bacteria growth with much higher sensitivity towards Staphylococcus aureus than E. coli (10, 33). However, the mechanism behind this inhibition was not previously known. The present inventors have found that ebselen and its diselenide are strong inhibitors of E. coli TrxR. In bacterial inhibition experiments using mutant strains lacking the enzyme glutathione reductase (GR encoded by the gor gene) or glutathione (gshA⁻ strain can not synthesize GSH) showed increased sensitivity towards ebselen. The interaction mechanism of ebselen and its diselenide with E. coli was studied showing the formation of a relative stable ebselen-TrxR complex at the active site of the enzyme. Interestingly, we found that the sulfur analogue of ebselen, ebsulfur (PZ25), and its disulfide were not inhibitors of the E. coli enzyme, but rather were substrates for the E. coli TrxR. However, as shown below, this is not the case for all bacterial enzymes since the Helicobacter pylori TrxR is inhibited.

Comparing the kinetic parameters of the interaction between the compounds and the two enzyme systems, provides better understanding of the chemical basis for the inhibition mechanism of ebselen and its diselenide towards the E. coli TrxR. This enhanced understanding of the principle chemical mechanism of ebselen diverse activity towards mammalian and E. coli TrxR is very important for the use of the drug and also for the development of effective antibiotic drugs based on same mechanism.

Furthermore, the finding that ebselen can inhibit E. coli TrxR leads us to a search for the new organoselenium compounds containing the basic structure of ebselen, to study their reactivity with E. coli thioredoxin reductase. We synthesized benzisoselenazol-3(2H)-ones and studied their reaction towards the thioredoxin reductase, to find out the relationship between the structure and reactivity. These compositions have, to varying extent, inhibitory effects on E. coli TrxR and bacterial growth, and therefore may be useful as antibiotics.

Different classes of benzisoselenazol-3(2H)-one compounds such as N-aryl (EbSe 7-10), N-unsubstituted (EbSe 6), N-alkyl (EbSe 2-4), N-2-pyridyl (EbSe 11 & 12) and N-4-pyridyl (EbSe 13) substituted benzisoselenazol-3(2H)-ones as well as bis-benzisoselenazol-3(2H)-ones (EbSe 14-16) were synthesized. Their inhibition effect on E. coli thioredoxin reductase (TrxR) was studied by thioredoxin dependent DTNB disulfide reduction assay in vitro. Detailed kinetic studies show that bisbenzisoselenazol-3(2H)-ones compounds (EbSe 14-16) inhibit TrxR at nanomolar concentrations while compounds EbSe 7-10, 12-13, 2-4 and parent ebselen, 2-phenyl-1,2-benzisoselenazol-3(2H)-one (EbSe 6) inhibit at micromolar concentrations. Other compounds did not inhibit *E. coli* TrxR. Tryptophan fluorescence measurements were carried out to follow the reaction of these compounds with reduced thioredoxin. Like ebselen, these compounds also rapidly oxidized reduced thioredoxin.

Different classes of benzisoselenazol-3(2H)-one-aryl (EbSe 1-5), unsubstituted (EbSe 6), alkyl (EbSe 7-8), 2-pyridyl (EbSe 9 & 10) and 4-pyridyl (11) substituted benzisoselenazol-3(2H)-ones, bisbenzisoselenazol-3(2H)-ones (EbSe 12-14), 7-azabenzisoselenazol-3(2H)-one (EbSe 17), selenamide (EbSe 20) and bis(2-carbamoyl)phenyl diselenide (EbSe 21) have various levels of antibiotic activity, and for example inhibit bacterial (e.g., *E. coli*) thioredoxin reductase (TrxR). Detailed kinetic studies show that bisbenzisoselenazol-3(2H)-ones compounds (EbSe 12-14) inhibit TrxR at nanomolar concentrations while compounds EbSe 6, 2, 9, 11-13, 17, and parent ebselen, 2-phenyl-1,2-benzisoselenazol-3(2H)-one (EbSe 1) inhibit at micromolar concentrations. Like ebselen, these compounds also rapidly oxidized reduced thioredoxin. See, U.S. Pat. No. 8,592,468, expressly incorporated herein by reference.

U.S. Pat. No. 8,592,468, expressly incorporated herein by reference discloses that benzisoselenazol-3(2H)-one and bisbenzisoselenazol-3(2H)-one derivatives were tested as potential *E. coli* TrxR inhibitors, Measured $IC_{50}$ and $K_i$ values (Table 1) indicate that the compounds EbSe 1-4, 10-14 are potent inhibitors for *E. coli* TrxR. The presence of covalent bond between selenium and nitrogen is important for the biological property of ebselen derivatives. The inhibition effect of selenamide (EbSe 20) was tested, which also possess direct Se—N bond. However, it has reduced inhibition effect than ebselen derivatives. Other derivatives EbSe 5-9 did not show significant inhibition on *E. coli* TrxR.

The oxidation properties of benzisoselenazol-3(2H)-one derivatives on reduced *E. coli* Trx-$(SH)_2$ were studied. Ebselen is reported as superfast thioredoxin oxidant, (32) and hence, used as the reference to compare the oxidant property of other compounds. The change of fluorescence intensity of 0.2 μM Trx-$(SH)_2$ by mixing with 0.2 μM benzisoselenazol-3(2H)-one show that all of the ebselen derivatives can oxidize the reduced Trx as the reference compound ebselen under identical conditions.

From the data shown in Table 1, it can be clearly seen that the substitution at the nitrogen atom of the benzisoselenazol-3(2H)-one ring has a significant effect on the inhibition of TrxR. The substitution of benzisoselenazol-3(2H)-one linked by alkyl chains (EbSe 12-14) has stronger inhibitory effect than unsubstituted (EbSe 6), alkyl (EbSe 7-8), aryl (EbSe 1-5), 2-pyridyl (EbSe 9-10) substituted ones, and also than compound EbSe 11 where the condensed benzene ring of benzisoselenazol-3(2H)-one is replaced by a pyridine ring. Compounds EbSe 12-14 show similar inhibitory effect irrespective of substitution at the second nitrogen atom and the number of alkyl chains between the two nitrogen atoms. From this observation it seems the second heteroatom nitrogen present in these compounds seems to important characteristic for their strong inhibition. Comparison of EbSe 6-8 show there is no inhibition when hydrogen is substituted by methyl (EbSe 6) or tert-butyl (EbSe 7) group. On the other hand, comparison of between EbSe 1, 10 and 11 indicates that modification of 2-phenyl-1,2-benzisoselenazol-3(2H)-one to 2-pyridyl benzisoselenazol-3(2H)-one or 7-azabenzisoselenazol-3(2H)-one does not have significant effect. Also inhibition is not much affected by the substitution of phenyl group attached to the nitrogen of benzisoselenazol-3(2H)-one. Selenamide EbSe 20 has by far less inhibition effect than the ebselen derivatives though direct Se—N bond present. It indicates the presence of five membered heterocyclic ring in addition to direct Se—N bond in the basic ebselen structure seems to so essential for their biological activities.

Bacterial TrxR is potent target for antibiotics development, in particular for the bacteria lacking glutathione system (see, US 2014/0088149; 2011/0288130; and 2009/0005422, expressly incorporated herein by reference). Here *E. coli* DHB4 strains wt, gshA$^-$, gor$^-$, oxyR$^-$ were used as the model to test the antibiotics activity of these ebselen derivatives. The MICs of these compounds were list in Table 1. Corresponding to the inhibition capacity of *E. coli* TrxR, ebselen derivatives EbSe 1-4 and EbSe 11-14 had strong ability to inhibit the bacterial growth. *E. coli* wt strain, strains gshA$^-$ or gor$^-$ which lost a functional glutathione system show more sensitive to ebselen derivatives EbSe 1-4 and 11, suggesting glutathione system plays a critical role in the protection of bacteria from these compounds. Whereas, all these strains exhibited the same sensitivity to EbSe 12, 14. This observation was verified by the further GPx activity measurement of these compounds (Table 1). The compounds EbSe 1-4 and 11 can react with glutathione and then induce the consumption of NADPH. In contrast, no GPx activity was observed for compound EbSe 12.

The inhibition of mammalian TrxR and the cytotoxicity of these ebselen derivatives (Table 1) was also examined. Ebselen EbSe 12-14 was the strongest inhibitor for mammalian TrxR with a nanomolar inhibitory level, and also showed toxicity for mammalian cells. Ebselen EbSe 4 had some activity to inhibit mammalian TrxR, but it was one of the least reagent among these compounds. This result may be explained by the property that the compound is the best reagent to react with glutathione. The other ebselen derivatives EbSe 1-3 did not inhibit mammalian TrxR and were less toxic reagents for the mammalian cells.

In summary, different classes of benzisoselenazol-3(2H)-one substituted compounds were found to exhibit different antibiotic properties because of their inhibition capacity on bacterial thioredoxin reductase. Generally, the -aryl, 2-pyridyl and 4-pyridyl substituted compounds possess a good inhibition ability to bacterial TrxR as well as the strong inhibition on bacterial growth and less toxicity. But the more substitution such as with chloro, carbono, or nitro substitution can alter antibiotic property. The Se—N bond structure is essential for the inhibition of bacterial TrxR as well as the inhibition of bacteria. Benzisoselenazol-3(2H)-one-unsubstituted or alkyl substituted compounds do not have the ability to inhibit bacterial TrxR. Bisbenzisoselenazol-3(2H)-ones have the strong inhibition for bacteria but also have the strongest toxicity for the mammalian cells.

Results

Ebselen and Ebselen Diselenide are Strong Competitive Inhibitors Towards *E. coli* TrxR.

When ebselen and ebselen diselenide are directly added in the solutions of *E. coli* TrxR and NADPH, no oxidations of NADPH were found. This is in line with the known fact that *E. coli* TrxR is strictly specific towards *E. coli* Trx. Further we examined the effect of ebselen in the reduction of disulfide by *E. coli* Trx and TrxR using both DTNB and insulin as substrates. Ebselen and its diselenide strongly inhibited the *E. coli* TrxR reduction towards *E. coli* Trx in a typical DTNB coupled assay. The same inhibition patterns are also shown for ebselen and ebselen diselenide in the insulin reduction assays (data not shown).

*E. coli* Trx largely increases the rate of reduction of ebselen and ebselen diselenide by mammalian TrxR (3, 32).

Direct reduction of ebselen and the diselenide reduced *E. coli* Trx also were observed by fluorescence spectroscopy and the second-order rate constants were determined to be $2\times10^7$ $M^{-1}s^{-1}$ and $1.7\times10^3$ $M^{-1}s^{-1}$, respectively (32). Thus ebselen and the diselenide are targeting the *E. coli* TrxR rather than the *E. coli* Trx.

The degree of inhibition caused by ebselen appears to depend on the concentrations of Trx and ebselen. An increase in [Trx] at constant [EbSe] decreases the degree of inhibition and an increase in [EbSe] at constant [Trx] increases the degree of inhibition, showing a typical competitive inhibition towards the TrxR. A series of Lineweaver-Burk plots of the initial rate for the reduction of DTNB in the presence of ebselen and ebselen diselenide gave a typical pattern of competitive inhibitions. The dissociation constants $K_i$ for the ebselen-TrxR and ebselen diselenide-TrxR complexes derived from the slopes $[(K_M/k_{cat})(1+[I]/K_i)]$ were $0.14\pm0.05$ μM and $0.46\pm0.05$ μM, respectively.

TABLE 2

Kinetic parameters determined for ebselen, its diselenide and their sulphur analogues with mammalian and *E. coli* TrxR.

| Compounds | Mammalian TrxR | | $k_{cat}/K_M$ ($μM^{-1}$ $min^{-1}$) | *E. coli* TrxR | | |
|---|---|---|---|---|---|---|
| | $k_{cat}$ ($min^{-1}$) | $K_M$ (μM) | | $k_{cat}$ ($min^{-1}$) | $K_M$ (μM) | $k_{cat}/K_M$ ($μM^{-1}min^{-1}$) |
| EbSe[a] | 588 | 2.5 | 235 | Inhibitor with $K_i$ = 0.15 ± 0.05 μM | | |
| (EbSe)$_2$[b] | 79 | 40 | 2 | Inhibitor with $K_i$ = 0.46 ± 0.03 μM | | |
| EbS | 1400 | 2.5 | 560 | 700 | 2.5 | 280 |
| (EbS)$_2$ | 1500 | 47 | 32 | 100 | 27.6 | 3.63 |

[a]from ref (3);
[b]from ref (32).

Ebselen inhibits the growth of *E. coli* strains and more sensitive towards gor$^-$ and grxA$^-$ mutants.

Since ebselen was a potent inhibitor of *E. coli* thioredoxin reductase we examined whether strains lacking components of the GSH-glutaredoxin reducing pathway (FIG. 6) would be more sensitive to the drug. Thus we examined the sensitivity of gor$^-$ and gshA$^-$ mutants to ebselen, which reside heavily on the TrxR reducing pathway. Wild type bacteria were more resistant than gor$^-$ and gshA$^-$ strains with gor$^-$ and gshA$^-$ strains being the most sensitive. This indicates that elimination of parts of the GSH pathway renders cells sensitive to ebselen. The explanation could be that ebselen inhibits TrxR or the thioredoxins, or is eliminated in cells by GSH. The sensitivity of strain trxA$^-$C$^-$ was similar, if not less, than that of the wild type, suggesting that the two *E. coli* thioredoxins were not primary targets for the compound. However, ebselen may be affecting a thioredoxin 1 related function as the gshA$^-$trxA$^-$ strain was more sensitive to the compound. In rich LB liquid cultures, resistance could additionally be associated with GSH from the culture medium which binds and neutralizes ebselen. The sensitivity to ebselen was increased in minimal media where gor$^-$ and gshA$^-$ strains hardly grew in its presence.

Sensitivity of Pathogenic Bacteria to Ebselen

Glutathione system is lacking and thus thioredoxin system is critical in many bacteria including some important pathogenic bacteria, such as methicillin resistant *Staphylococcus aureus*, *Helicobacter pylori*, *Mycobacterium tuberculosis*, etc. (36-40). Based on our principle that ebselen can target thioredoxin system in glutathione deficient bacteria, ebselen is the potential drug for inhibition of these bacterial. As also shown in reference 10, methicillin resistant *Staphylococcus aureus*, *Bacillus subtilis* are quite sensitive to ebselen. We also investigated *Mycobacterium tuberculosis* sensitivity on ebselen, the test was done in the radiometric BACTEC 460 system. As shown in Table 3, several multi-drug resistant *Mycobacterium tuberculosis* strains are sensitive to ebselen. The medium contains 5 g/l of albumin or 70 μM which will bind ebselen. Ebselen at 10 mg/l is 26 μM. The albumin free SH groups are about 50% or 35 μM. Therefore, the MIC is dependent upon albumin saturation and probably lower than 20 mg/l.

The inhibition of ebselen on *H. pylori* was therefore investigated. For two macrolide sensitive strains, the minimal bactericidal concentration (MBC) are 3.125 and 6.25 μg/ml, for macrolide resistant strains, the MBC is 12.5 μg/ml. Taken together, our results strongly support that the inhibition of ebselen on these glutathione deficient bacteria is due to the oxidization of thioredoxin system by ebselen.

TABLE 3

Sensitivity of MDR *Mycobacterium tuberculosis* to ebselen

| | | Sensitivity to ebselen (μg/ml) | | | |
|---|---|---|---|---|---|
| Strain | Ab-res | 80 | 40 | 20 | 10 |
| H37Rv | S | S | S | S | R |
| Panel3:24 | MDR | S | S | S | R |
| BTB 98-310 | MDR | S | S | S | R |

S: sensitive to rifampicin as positive control (no growth); R: resistant.

TABLE 4

Bactericidal effects of ebselen on *Helicobacter pylori*

| Strain | Sensitivity to Macrolide | Sensitivity to ebselen (μg/ml) | | | | | | | |
|---|---|---|---|---|---|---|---|---|---|
| | | 100 | 50 | 25 | 12.5 | 6.25 | 3.125 | 1.56 | 0.78 |
| MS G6 | S | S | S | S | S | S | S | S | R | R |
| MS G142 | S | S | S | S | S | S | R | R | R |
| MR G162 | R | S | S | S | S | R | R | R | R |
| MR G193 | R | S | S | S | S | R | R | R | R |

S: sensitive; R: resistant.

*E. coli* TrxR Inhibition by Ebselen Derivatives

All the benzisoselenazol-3(2H)-one and bisbenzisoselenazol-3(2H)-one derivatives were tested as potential *E. coli* TrxR inhibitors by standard DTNB assay. IC$_{50}$ values were calculated by following the activity of TrxR reducing DTNB by NADPH at 412 nm. The reactions were started by adding 1 mM DTNB to the mixture of 100 nM TrxR, 2 μM Trx, 240 μM NADPH, and different concentration of inhibitor (1-40 μM). For determining the inhibition constants ($K_i$), indicated amount of inhibitor was mixed with total volume 500 μL containing 1 mM DTNB, 240 μM NADPH, fixed thioredoxin concentration (1 or 2 or 4 μM) and buffer containing 50 mM Tris-Cl, 2 mM EDTA, pH 7.5. The reactions were started by adding 6 nM TrxR at room temperature. Inhibition constants ($K_i$) for all the compounds were measured from Dixon plot, which plots 1/v versus [I]=$A_{412}$/min, I=Inhibitor concentration). Measured IC$_{50}$ and $K_i$ values (Table 1) indicate that the compounds EbSe 6-9, 12-16 are potent inhibitors for *E. coli* TrxR. The presence of covalent bond between selenium and nitrogen is so important for the biological property of ebselen derivatives. Other derivatives did not show significant inhibition on *E. coli* TrxR.

Oxidation *E. coli* Trx-(SH)$_2$ by Ebselen Derivatives

Oxidant property of benzisoselenazol-3(2H)-one derivatives on reduced *E. coli* Trx-(SH)$_2$ were studied by fluorescence spectroscopy. This property was chosen to follow the reaction of Trx with benzisoselenazol-3(2H)-one derivatives since *E. coli* Trx-(SH)$_2$ has 3-fold higher tryptophan fluorescence than Trx-S$_2$. Ebselen is reported as superfast thioredoxin oxidant[32] and hence, used as the reference to compare the oxidant property of other compounds. The change of fluorescence intensity of 0.2 µM Trx-(SH)$_2$ by mixing with 0.2 µM benzisoselenazol-3(2H)-one show that they all can oxidize the reduced Trx as the reference compound ebselen under identical conditions.

Correlation Between the Structure and their Inhibition

From the data shown in Table 1, it can be clearly seen that the substitution at nitrogen atom of benzisoselenazol-3(2H)-one ring has a significant effect on the inhibition of TrxR. The substitution of benzisoselenazol-3(2H)-one linked by alkyl chains (14-16) has stronger inhibitory effect than unsubstituted (EbSe 6), alkyl (EbSe 2-4), aryl (EbSe 7-10), 2-pyridyl (EbSe 11-12) and 4-pyridyl (EbSe 13) substituted ones. Compounds EbSe 14-16 show similar inhibitory effect irrespective of substitution at the second nitrogen atom and the number of alkyl chains between the two nitrogen atoms. From this observation it seems the second heteroatom nitrogen present in these compounds seems to important characteristic for their strong inhibition. Comparison of EbSe 2-4 show there is no inhibition when hydrogen is substituted by methyl (6) or tert-butyl (7) group. On the other hand, comparison of EbSe 6, 12 and 13 indicates that modification of the 2-phenyl-1,2-benzisoselenazol-3(2H)-one into an N-2-pyridyl benzisoselenazol-3(2H)-one or an N-4-pyridyl benzisoselenazol-3(2H)-one does not have a significant effect. Also inhibition is not much affected by the substitution of phenyl group attached to the nitrogen of benzisoselenazol-3(2H)-one.

Inhibition of Bacterial Growth by Ebselen Derivatives

Bacterial TrxR is potent target for antibiotics development, in particular for the bacteria lacking glutathione system. Here *E. coli* DHB4 strains wt, gshA$^-$, gor$^-$, oxyR$^-$ were used as the model to test the antibiotics activity of these ebselen derivatives corresponding to the inhibition capacity of *E. coli* TrxR, ebselen derivatives EbSe 6-9 and 13-16 had strong ability to inhibit the bacterial growth. *E. coli* wt strain, strains gshA$^-$ or gor$^-$ which lost a functional glutathione system show more sensitive to ebselen derivatives EbSe 6-9 and 13, suggesting that the glutathione system plays a critical role in the protection of bacteria from these compound. Whereas, all these strains exhibited the same sensitivity to EbSe 14, 16.

Inhibition of *H. pylori* TrxR and *H. pylori* Strains by PZ-25 (Ebsulfur).

*H. pylori* TrxR activity was inhibited by 4, 20, and 40 µM of PZ-25 by insulin reduction assay. Consistent with the inhibition of *H. pylori* TrxR activity, *H. pylori* strains were shown to be sensitive to ebsulfur. For NCTC11637 strain, the MIC for ebselen, PZ-25, metronidazole was 3.13, 1.56, and 0.78 µg/ml respectively. For strain YS-16, The MIC for ebselen, PZ-25, metronidazole was 3.13, 0.39, 6.25 µg/ml respectively.

Discussion

Ebselen is an antioxidant due to the special selenium chemistry it interplayed with thiol and hydrogen peroxide (1, 3, 24, 32). The mechanism was recently described to be via the mammalian thioredoxin system with the formation of ebselen diselenide as an important part of the mechanism (3, 32). Ebselen also has low toxicity for the human body because the selenium moiety is not liberated during biotransformation so it does not enter the selenium metabolism of the organism (41-43). At low concentrations, ebselen even inhibits a number of enzymes involved in inflammation such as lipoxygenases, NO synthesase, protein kinase C and H$^+$/K$^+$-ATPase (1). The inhibitions were manifested on the cellular level and may contribute to the anti-inflammatory potential of ebselen (1).

Ebselen has another interesting pharmaceutical profile, namely its antibacterial character, targeting the bacterial thioredoxin reductase as shown herein, with structure and properties distinct from the mammalian counterpart.

The inhibition kinetic parameters determined for the ebselen and its diselenide towards *E. coli* TrxR indicate that both compounds are strong inhibitors with nanomolar affinities. It was reported that the growth of *Staphylococcus aureus* 209P was inhibited by 0.20 µg/ml of ebselen, while strains of the family Enterobacteriaceae were more resistant to the drug (10). The selenium in PZ51 was essential, since its sulfur analogue (PZ25) lost the antibacterial activity (10). In results of cell experiments shown in FIGS. 8 and 9, it also clearly showed that ebselen inhibited bacterial strains. The mutants lacking glutathione reductase (gor$^-$) and glutathione (gshA$^-$) showed increased sensitivity.

In *E. coli*, it was long proposed that thioredoxin system and glutaredoxin system are two crucial pathways for the electron flow to be delivered to the ribonucleotide reductase for DNA synthesis (FIG. 6) (4, 6, 14, 15, 35). Thiol reductions by the two systems also play key roles in cell growth as well as redox regulation of a variety of biological functions. FIG. 8 shows that the sensitivity to ebselen increased with mutants lacking glutathione reductase (gor$^-$) and glutathione (gshA$^-$), indicating that perturbations of the GSH reducing pathway render cells more sensitive to ebselen. The sensitivity to ebselen was increased in minimal media where gor$^-$ and gshA$^-$ strains hardly grew. The increased sensitivity in minimal media could be expected since lack of GSH would increase demands for electrons from the thioredoxin system for sulfate reduction (4).

The results clearly show that elimination of GSH or glutathione reductase which makes cells more dependent on the thioredoxin system leads to a greater degree of inhibition. From the results previously published (10) the large difference in sensitivity of bacteria to ebselen is clearly correlated to having GSH or not. Gram positive strains of bacteria like *S. aureus* or *B. subtillus* lack GSH (44). *Bacillus subtilis* e.g. has formally no glutaredoxin pathway but several thioredoxins which are essential (37). The bacterial thioredoxin reductases are therefore drug targets for ebselen.

From a simple chemical point of view, the reaction of Ebselen with the *E. coli* TrxR is much slower or completely stopped for the reasons of a highly polar CysS-SeEb bond in the second disulfide interchange reaction. *E. coli* TrxR is known to undergo an essential conformation change allowing electron flows to go through from NADPH to FAD and the active disulfide in each catalytic cycle. The kinetic constant of this conformation change was observed to be ca 53 s$^{-1}$ at 25° C. The inhibition of the *E. coli* TrxR by ebselen and its diselenide are therefore believed to result from the slow release of ebselen selenol from the relatively polar selenenolsulfide bridge, and the determined conformation change from FR to FO of the *E. coli* TrxR-SeEbSe complex.

The *E. coli* TrxR is known for its high specificity towards its Trx, and in fact, PZ25 and its disulfide are the first two small molecules found as substrates. The specificity of *E. coli* TrxR as compared with its mammalian counterpart may be principally attributed to this specific conformation change, which differentiates between substrate oxidants except where their disulfide exchange reactions with the active-site thiols in the *E. coli* TrxR are fast enough to not disrupt the normal conformation change of the enzyme.

The drug has no inhibitory activity of mammalian thioredoxin reductases due to their highly different structures and mechanisms when compared with the ubiquitous bacterial enzymes (8, 18). The ebselen molecule is thus an antioxidant drug with useful antibacterial spectrum and two effects for the price of one.

Thus the non-toxic drug ebselen inhibits bacterial growth due to the large differences in its mechanism of action towards bacterial and mammalian TrxR, the two structurally very distinct enzymes. In pathogenic bacteria like *M. tuberculosis* the defense from the bacterium against the host killing by reactive oxygen species derived from macrophages is dependent on thioredoxin coupled peroxidases. Thus the inhibition of the thioredoxin system would also sensitize the bacteria in the intracellular environment. Therefore, ebselen and derivatives would be effective agents against the survival and virulence of *M. tuberculosis* in its dormant stage in macrophages where the pathogen has to defend itself against reactive oxygen species from the host as well as to repair its DNA. The latter process is dependent on the thioredoxin system and ribonucleotide reductase and targeted by ebselen. In fact, ebselen is also an effective direct inhibitor of *E. coli* ribonucleotide reductase (data not shown).

In summary, different classes of benzisoselenazol-3(2H)-one substituted compounds were found to exhibit different antibiotic properties because of their inhibition capacity on bacterial thioredoxin reductase. Generally, the N-aryl, N-2-pyridyl and N-4-pyridyl substituted compounds as well as bis-benzisoselenazol-3(2H)-ones possess a good inhibition ability towards bacterial TrxR. But substitution with chloro, carboxy, or nitro groups can alter the antibiotic properties.

REFERENCES

References (Each of the Following is Expressly Incorporated Herein by Reference in its Entirety)

1. Schewe, T. (1995) *General Pharmacology* 26, 1153-1169.
2. Ogawa, A., Yoshimoto, T., Kikuchi, H., Sano, K., Saito, I., Yamaguchi, T., Yasuhara, H. & Grp, E. S. (1999) *Cerebrovascular Diseases* 9, 112-118.
3a. Patent application Ser. No. 09/926,218, United States Patent and Trademark Office, Arne Holmgren et al, Substrate for thioredoxin reductase, National Stage of PCT JP00/02076.
3b. Zhao, R., Masayasu, H. & Holmgren, A. (2002) *Proc Natl Acad Sci USA* 99, 8579-84.
4. Holmgren, A. (1985) *Annu Rev Biochem* 54, 237-71.
5. Holmgren, A. (1989) *J Biol Chem* 264, 13963-6.
6. Jordan, A. & Reichard, P. (1998) *Annu Rev Biochem* 67, 71-98.
7. Zhong, L., Arner, E. S., Ljung, J., Aslund, F. & Holmgren, A. (1998) *J Biol Chem* 273, 8581-91.
8. Zhong, L. & Holmgren, A. (2000) *J Biol Chem* 275, 18121-8.
9. Williams, C. H., Arscott, L. D., Muller, S., Lennon, B. W., Ludwig, M. L., Wang, P. F., Veine, D. M., Becker, K. & Schirmer, R. H. (2000) *Eur J Biochem* 267, 6110-7.
10. Nozawa, R., Yokota, T. & Fujimoto, T. (1989) *Antimicrob Agents Chemother* 33, 1388-90.
11. Arner, E. S. & Holmgren, A. (2000) *Eur J Biochem* 267, 6102-9.
12. Ritz, D. & Beckwith, J. (2001) *Annu Rev Microbiol* 55, 21-48.
13. Arner, E. S., Zhong, L. & Holmgren, A. (1999) *Methods Enzymol* 300, 226-39.
14. Ortenberg, R., Gon, S., Porat, A. & Beckwith, J. (2004) *Proc Natl Acad Sci USA* 101, 7439-44.
15. Luthman, M. & Holmgren, A. (1982) *Biochemistry* 21, 6628-33.
16. Becker, K., Gromer, S., Schirmer, R. H. & Muller, S. (2000) *Eur J Biochem* 267, 6118-25.
17. Tamura, T. & Stadtman, T. C. (1996) *Proceedings of the National Academy of Sciences of the United States of America* 93, 1006-1011.
18. Zhong, L., Arner, E. S. & Holmgren, A. (2000) *Proc Natl Acad Sci USA* 97, 5854-9.
19. Sandalova, T., Zhong, L., Lindqvist, Y., Holmgren, A. & Schneider, G. (2001) *Proc Natl Acad Sci USA* 98, 9533-8.
20. Lennon, B. W., Williams, C. H., Jr. & Ludwig, M. L. (2000) *Science* 289, 1190-4.
21. Lennon, B. W., Williams, C. H., Jr. & Ludwig, M. L. (1999) *Protein Sci* 8, 2366-79.
22. Waksman, G., Krishna, T. S., Williams, C. H., Jr. & Kuriyan, J. (1994) *J Mol Biol* 236, 800-16.
23. Lennon, B. W. & Williams, C. H., Jr. (1997) *Biochemistry* 36, 9464-77.
24. Sies, H. (1994) *Oxygen Radicals in Biological Systems, Pt D* 234, 476-482.
25. Maulik, N., Yoshida, T. & Das, D. K. (1998) *Free Radic. Biol. Med.* 24, 869-875.
26. Dawson, D. A., Masayasu, H., Graham, D. I. & Macrae, I. M. (1995) *Neurosci. Lett.* 185, 65-69.
27. Takasago, T., Peters, E. E., Graham, D. I., Masayasu, H. & Macrae, I. M. (1997) *Br. J. Pharmacol.* 122, 1251-1256.
28. Imai, H., Masayasu, H., Dewar, D., Graham, D. I. & Macrae, I. M. (2001) *Stroke* 32, 2149-2154.
29. Namura, S., Nagata, I., Takami, S., Masayasu, H. & Kikuchi, H. (2001) *Stroke* 32, 1906-1911.
30. Saito, I., Asano, T., Sano, K., Takakura, K., Abe, H., Yoshimoto, T., Kikuchi, H., Ohta, T. & Ishibashi, S. (1998) *Neurosurgery* 42, 269-278.
31. Yamaguchi, T., Sano, K., Takakura, K., Saito, I., Shinohara, Y., Asano, T. & Yasuhara, H. (1998) *Stroke* 29, 12-17.
32. Zhao, R. & Holmgren, A. (2002) *J Biol Chem* 277, 39456-62.
33. Bien, M., Blaszczyk, B., Kalinowska, K., Mlochowski, J. & Inglot, A. D. (1999) *Arch Immunol Ther Exp (Warsz)* 47, 185-93.
34. Holmgren, A. & Bjornstedt, M. (1995) *Methods Enzymol* 252, 199-208.
35. Prinz, W. A., Aslund, F., Holmgren, A. & Beckwith, J. (1997) *J Biol Chem* 272, 15661-7.
36. Windle, H. J., Fox, A., Ni Eidhin, D. & Kelleher, D. (2000) *J Biol Chem* 275, 5081-9.
37. Scharf, C., Riethdorf, S., Ernst, H., Engelmann, S., Volker, U. & Hecker, M. (1998) *J Bacteriol* 180, 1869-77.
38. Uziel, O., Borovok, I., Schreiber, R., Cohen, G. & Aharonowitz, Y. (2004) *J Bacteriol* 186, 326-34.
39. Comtois, S. L., Gidley, M. D. & Kelly, D. J. (2003) *Microbiology-Sgm* 149, 121-129.

40. Jaeger, T., Budde, H., Flohe, L., Menge, U., Singh, M., Trujillo, M. & Radi, R. (2004) *Archives of Biochemistry and Biophysics* 423, 182-191.
41. Fischer, H., Terlinden, R., Lohr, J. P. & Romer, A. (1988) *Xenobiotica* 18, 1347-1359.
42. Muller, A., Gabriel, H., Sies, H., Terlinden, R., Fischer, H. & Romer, A. (1988) *Biochem. Pharmacol.* 37, 1103-1109.
43. Sies, H. (1989) in *Selenium in Biology and Medicine*, ed. Wendel, A. (Springer-Verlag, Heidelberg), pp. 153-162.
44. Newton, G. L. & Fahey, R. C. (1995) *Methods Enzymol* 251, 148-66.
45. Trujillo, M Mauri, P. L., Benazzi, L., Comini, M., De Palma, A., Flohé, L., Radi, R. Stehr, M., Singh, M. Ursini, F., and Jaeger, T. (2006) J. Biol. Chem. In press on May 8 M601008200.
46. C. H. J. Williams, *In chemistry and biochemistry of flavoenzymes* (F. Müller, Eds, vol 3 pp 121-211. CRC Press Inc. Boca Raton Fla.
47. A.-B. Witte, K. Anestal, E. Jerremalm, H. Ehrsson, E. S. J. Arnér, *Free Rad. Biol. Med.,* 2005, 39, 696-703.
48. R. Millet, S. Urig, J. Jacob, E. Amtmann, J.-P. Moulinoux, S. Gromer, K. Becker and E. Davioud-Charvet, *J. Med. Chem.,* 2005, 48, 7024-7039.
49. M. P. Rigobello, G. Scutari, A. Folda and A. Bindoli, *Biochem. Pharmacol.,* 2004, 67, 689-696.
50. K. Becker, C. Herold-Mende, J. J. Park, G. Lowe and R. H. Schirmer, *J. Med. Chem.,* 2001, 44, 2784-2792.
51. P. Wipf, S. M. Lynch, G. Powis, A. Birmingham and E. E. Englund, Org. Biomol. Chem., 2005, 3, 3880-3882.
52. P. Wipf, S. M. Lynch, A. Birmingham, G. Tamayo, A. Jimenez, N. Campos and G. Powis, Org. Biomol. Chem., 2004, 2, 1651-1658.
53. P. Wipf, T. D. Hopkins, J.-K. Jung, S. Rodriguez, A. Birmingham, E. C.
Southwick, J. S. Lazoc and G. Powis, Biorg. Med. Chem. Lett. 2001, 11, 2637-2641.
54. J. Dessolin, C. Biot and E. Davioud-Charvet, J. Org. Chem., 2001, 66, 5616-5619.
55. K. U. Schallreuter, F. K. Gleason, J. M. Wood, Biochim. Biophys. Acta 1990, 1054, 14-20.
56. S. Gromer, R. H. Schirmer and K. Becker, FEBS Lett. 1997, 412, 318-320.
57. J. Nordberg, L. Zhong, A. Holmgren and E. S. J Arner, J. Biol. Chem., 1998, 273, 10835-10842.
58. L. Engman, I. Cotgreave, M. Angulo, C. W. Taylor, G. D. Paine-Murrieta and G. Powis Anticancer Res., 1997, 17, 4599-4605.
59. L. Engman, T. Kandra, A. Gallegos, R. Williams and G. Powis, Anticancer Drug Des., 2000, 15, 323-330.
60. L. Engman, N. Al-Maharik, M. McNaughton, A. Birmingham and G. Powis, Bioorg. Med. Chem., 2003, 11, 5091-5100.
61. L. Engman, N. Al-Maharik, M. McNaughton, A. Birmingham and G. Powis, Anti-Cancer Drugs 2002, 14, 153-161.
62. H. Wojtowicz, K. Kloc, I. Maliszewska, J. Mlochowski, M. Pietka and E. Piasecki, I L FARMACO 2004, 59, 863-868.
63. J. Mlochowski, K. Kloc, L. Syper, A. D. Inglot and Piasecki, Liebigs Ann. Chem., 1993, 1239-1244.
64. M. Osajda, K. Kloc, J. Mlochowski, E. Piasecki and K. Rybka, Polish J. Chem., 2001, 75, 823-830.
65. D. D. Perrin, W. L. F. Armargo and D. R. Ferrin, Purification of Laboratory Chemicals; Pergamon: New York, 1980.
66. H. J. Windle, A. Fox, D. Ni Eidhin and D. Kelleher, J Biol Chem. 2000, 275, 5081-9.
67. Lillig C H & Holmgren A (2007) Thioredoxin and related molecules—from biology to health and disease. *Antioxid Redox Signal* 9(1):25-47.
68. Lu J & Holmgren A (2014) The thioredoxin antioxidant system. *Free radical biology & medicine* 66:75-87.
69. Lu J, et al. (2013) Inhibition of bacterial thioredoxin reductase: an antibiotic mechanism targeting bacteria lacking glutathione. *FASEB journal: official publication of the Federation of American Societies for Experimental Biology* 27(4):1394-1403.
70. Russell A D & Hugo W B (1994) Antimicrobial activity and action of silver. *Progress in medicinal chemistry* 31:351-370.
71. Chopra I (2007) The increasing use of silver-based products as antimicrobial agents: a useful development or a cause for concern? *J Antimicrob Chemother* 59(4):587-590.
72. Wilkinson L J, White R J, & Chipman J K (2011) Silver and nanoparticles of silver in wound dressings: a review of efficacy and safety. *Journal of wound care* 20(11):543-549.
73. Liau S Y, Read D C, Pugh W J, Fun J R, & Russell A D (1997) Interaction of silver nitrate with readily identifiable groups: relationship to the antibacterial action of silver ions. *Letters in applied microbiology* 25(4):279-283.
74. Morones-Ramirez J R, Winkler J A, Spina C S, & Collins J J (2013) Silver enhances antibiotic activity against gram-negative bacteria. *Science translational medicine* 5(190):190ra181.
75. Zhang X, et al. (2011) Disruption of the mitochondrial thioredoxin system as a cell death mechanism of cationic triphenylmethanes. *Free Radic Biol Med* 50(7):811-820.
76. Lu J, et al. (2013) Ebsulfur is a benzisothiazolone cytocidal inhibitor targeting the trypanothione reductase of *Trypanosoma brucei*. *J Biol Chem* 288(38):27456-27468.
77. R. Zhao, H. Masayasu and A. Holmgren, Proc. Natl. Acad. Sci. U.S.A, 2002, 99, 8579-8584.
78. R. J. Hatchett, R. J Gryglewski, J. Mlochowski, A. Zembowicz and W. Radziszewski, *J. Physiol. Pharmacol.,* 1994, 45, 55-67.
79. N. Kamigata, H. Lizuka, A. Lizuoka and M. Kobayashi, Bull. Chem. Soc. Jpn. 1986, 59, 2179-2183.
80. K. Kloc, I. Maliszewska and J. Mlochowski, Synth. Commun., 2003, 33, 3805-3815.
81. M. Osajda and J. Mlochowski, Tetrahedron 2002, 58, 7531-7537.
82. Phosphorous Sulfur Silicon Reltd. Element. 2000, 163, 211-218.
83. Mag. Res. Chem. 1987, 25, 955.
84. K. Kandasamy, S. Kumar, H. B. Singh, R. J. Butcher and K. T. Holman, Eur. J. Inorg. Chem., 2004, 1014-1023.
85. S. S. Zade, H. B. Singh and R. J. Butcher, *Angew. Chem., Int. Ed.,* 2004, 43, 4513-4515. and references therein.
86. Luo Z, Liang L, Sheng J, Pang Y, Li J, Huang L, Li X, "Synthesis and biological evaluation of a new series of ebselen derivatives as glutathione peroxidase (GPx) mimics and cholinesterase inhibitors against Alzheimer's disease", Bioorg Med Chem. 2014 Feb. 15; 22(4):1355-61. doi: 10.1016/j.bmc.2013.12.066. Epub 2014 Jan. 9.

Ebse 2

1. Wojtowicz, H.; Kloc, K.; Maliszewska, I.; Mlochowski, J.; Pietka, M.; Piasecki, E. Azaanalogs of ebselen as antimicrobial and antiviral agents: Synthesis and properties. Farmaco (2004), 59(11), 863-868.
2. Mlochowski, Jacek; Brzaszcz, Monika; Chojnacka, Magdalena; Giurg, Miroslaw; Wojtowicz, Halina. Diaryl diselenides and benzisoselenazol-3(2H)-ones as oxygen-transfer agents. ARKIVOC (Gainesville, Fla., United States) (2004), (3), 226-248.
3. Sakimoto, Yukiko; Hirao, Kimihiko; Musaev, Djamaladdin G. Reactivity of Ebtellur Derivatives with the Peroxynitrite Anion: Comparison with their Ebselen Analogues. Journal of Physical Chemistry A (2003), 107(29), 5631-5639.
4. Musaev, Djamaladdin G.; Geletii, Yurii V.; Hill, Craig L.; Hirao, Kimihiko. Can the Ebselen Derivatives Catalyze the Isomerization of Peroxynitrite to Nitrate? Journal of the American Chemical Society (2003), 125(13), 3877-3888.
5. Pfeiffer, W.-D. Product class 21: annulated isoselenazole compounds. Science of Synthesis (2002), 11 931-940.
6. Dakova, B; Walcarius, A; Lamberts, L; Evers, M. Electrochemical behaviour of seleno-organic compounds Part 5. [2H] Benziso-1,2-selenazol-3-one, [3H] benzo-2,1-thiaselenol-3-one and [3H] benzo-1,2-dithiol-3-one. Electrochimica Acta (2001), 46(9), 1259-1265.
7. Xu, Han-Sheng; Hu, Li-Ming; Liu, Zhao-Jie; Peng, Yun-Shan; Guo, Zhen-Qiu. Synthesis of 2-ethoxycarbonylphenylselenoaminomethylphosphonate. Phosphorus, Sulfur and Silicon and the Related Elements (2000), 163 211-218.
8. Mhizha, Sungano; Mlochowski, Jacek. Synthesis of 2-acyl- and 2-sulfonylbenzisoselenazol-3-(2H)-ones. Synthetic Communications (1997), 27(2), 283-291.
9. Bergthaller, Peter; Borst, Hans-Ulrich; Bell, Peter; Buescher, Ralf; Willsau, Johannes; Stetzer, Thomas. Selenium compound as photographic stabilizer. Ger. Offen. (1996), 22 pp.
10. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
11. Witting, Paul K.; Westerlund, Christer; Stocker, Roland. A rapid and simple screening test for potential inhibitors of tocopherol-mediated peroxidation of LDL lipids. Journal of Lipid Research (1996), 37(4), 853-867.
12. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
13. Kuehn-Velten, N.; Sies, H. Optical spectral studies of ebselen interaction with cytochrome P-450 of rat liver microsomes. Biochemical Pharmacology (1989), 38(4), 619-25.
14. Piette, Jean Louis; Loehr, Josef Peter; Leyck, Sigurd. Benzisoselenazolone-containing pharmaceutical preparation and its use. Ger. Offen. (1982), 10 pp.

Ebse 3

1. Musaev, Djamaladdin G.; Geletii, Yurii V.; Hill, Craig L.; Hirao, Kimihiko. Can the Ebselen Derivatives Catalyze the Isomerization of Peroxynitrite to Nitrate? Journal of the American Chemical Society (2003), 125(13), 3877-3888.
2. Pfeiffer, W.-D. Product class 21: annulated isoselenazole compounds. Science of Synthesis (2002), 11 931-940.
3. Inglot, Anna D.; Mlochowski, Jacek; Zielinska-Jenczylik, Janina; Piasecki, Egbert; edwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Mlochowski, Jacek; Giurg, Miroslaw; Kubicz, Elzbieta; Said, Samy B. Benzisoselenazol-3(2H)-ones and bis(2-carbamoylphenyl) diselenides as new catalysts for hydrogen peroxide oxidation of organic compounds. Synthetic Communications (1996), 26(2), 291-300.
5. Piatek, M.; Oleksyn, B.; Sliwinski, J. 2-Methyl-2H-1,2-benzisoselenazol-3-one. Acta Crystallographica, Section C: Crystal Structure Communications (1995), C51(2), 298-301.
6. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
7. Mlochowski, J.; Syper, L.; Stefaniak, L.; Domalewski, W.; Schilf, W.; Webb, G. A. A proton, carbon-13, nitrogen-15 and selenium-77 NMR study of three organoselenium compounds. Journal of Molecular Structure (1992), 268(1-3), 311-14.
8. Dakova, B.; Kauffmann, J. M; Evers, M.; Lamberts, L.; Patriarche, G. J. Electrochemical behavior of pharmacologically interesting seleno-organic compounds—I. N-alkyl- and N-aryl-1,2-benzisoselenazol-3(2H)-one, Electrochimica Acta (1990), 35(7), 1133-8.
9. Parnham, M. J.; Biedermann, J.; Bittner, C.; Dereu, N.; Leyck, S.; Wetzig, H. Structure-activity relationships of a series of anti-inflammatory benzisoselenazolones (BISAs). Agents and Actions (1989), 27(3-4), 306-8.
10. Kuehn-Velten, N.; Sies, H. Optical spectral studies of ebselen interaction with cytochrome P-450 of rat liver microsomes. Biochemical Pharmacology (1989), 38(4), 619-25.
11. Welter, Andre; Fischer, Hartmut; Christiaens, Leon; Wendel, Albrecht; Etschenberg, Eugen. 2,2-Diselenobis [benzamide]s of primary amines with glutathione peroxidase-like activity. Ger. Offen. (1986), 26 pp
12. Piette, Jean Louis; Loehr, Josef Peter; Leyck, Sigurd. Benzisoselenazolone-containing pharmaceutical preparation and its use. Ger. Offen. (1982), 10 pp.
13. Van Caneghem, P. Comparative effects of selenium compounds and their sulfur analogs on the stability of lysosomes and mitochondria in vitro. Biochemical Pharmacology (1974), 23(24), 3491-500.

Ebse 4

1. Nakashima, Yusuke; Shimizu, Toshio; Hirabayashi, Kazunori; Kamigata, Nobumasa. Optically Active Seleninamides: Isolation, Absolute Configuration, and Racemization Mechanism. Journal of Organic Chemistry (2005), 70(3), 868-873.
2. Pfeiffer, W.-D. Product class 21: annulated isoselenazole compounds. Science of Synthesis (2002), 11 931-940.
3. Fong, Mei C.; Schiesser, Carl H. Intramolecular Homolytic Substitution with Amidyl Radicals: A Free-Radical Synthesis of Ebselen and Related Analogs. Journal of Organic Chemistry (1997), 62(10), 3103-3108.

4. Bergthaller, Peter; Borst, Hans-Ulrich; Bell, Peter; Buescher, Ralf; Willsau, Johannes; Stetzer, Thomas. Selenium compound as photographic stabilizer. Ger. Offen. (1996), 22 pp.
5. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
6. Mlochowski, Jacek; Giurg, Miroslaw; Kubicz, Elzbieta; Said, Samy B. Benzisoselenazol-3(2H)-ones and bis(2-carbamoylphenyl) diselenides as new catalysts for hydrogen peroxide oxidation of organic compounds. Synthetic Communications (1996), 26(2), 291-300.
7. Fong, Mei C.; Schiesser, Carl H. Reactions of 2,2'-diselenobis(N-alkylbenzamides) with peroxides: a free-radical synthesis of ebselen and related analogs. Tetrahedron Letters (1995), 36(40), 7329-32.
8. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
9. Welter, Andre; Dereu, Norbert. Benzisoselenazolones as antiarthritics. Ger. Offen. (1986), 13 pp.
10. Welter, Andre; Fischer, Hartmut; Christiaens, Leon; Wendel, Albrecht; Etschenberg, Eugen. 2,2-Diselenobis [benzamide]s of primary amines with glutathione peroxidase-like activity. Ger. Offen. (1986), 26 pp.

Ebse 6

This is the parent compound, ebselen and there are a number of reports.

Ebse 7

1. Pfeiffer, W.-D. Product class 21: annulated isoselenazole compounds. Science of Synthesis (2002), 11 931-940
2. Bien, Malgorzata; Blaszczyk, Barbara; Kalinowska, Katarzyna; Mlochowski, Jacek; Inglot, Anna D. Antifungal activity of 2-(4-chlorophenyl)-1,2-benzisoselenazol-3 (2H)-one, the analog of Ebselen. Archivum Immunologiae et Therapiae Experimentalis (1999), 47(3), 185-193.
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Blaszczyk, Barbara; Inglot, Anna D.; Kowalczyk-Bronisz, Stefania H.; Szymaniec, Stanislaw; Mlochowski, Jacek. Immunotropic activities of benzisoselenazolones and organic diselenides in mice. Archivum Immunologiae et Therapiae Experimentalis (1995), 43(5-6), 305-11.
5. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.
6. Dakova, B.; Lamberts, L.; Evers, M.; Dereu, N. Electrochemical behavior of pharmacologically interesting seleno-organic compounds—2. 7-Substituted-N-aryl-1,2-benzisoselenazol-3(2H)-one. Electrochimica Acta (1991), 36(3-4), 631-7.
7. Dakova, B; Kauffmann, J. M; Evers, M.; Lamberts, L; Patriarche, G. J, Electrochemical behavior of pharmacologically interesting seleno-organic compounds—I. N-alkyl- and N-aryl-1,2-benzisoselenazol-3(2H)-one. Electrochimica Acta (1990), 35(7), 1133-8.
8. Kuehn-Velten, Nikolaus; Sies, Helmut. Optical spectral studies of ebselen interaction with cytochrome P-450 of rat liver microsomes. Biochemical Pharmacology (1989), 38(4), 619-25.
9. Kamigata, Nobumasa; Takata, Mayumi; Matsuyama, Haruo; Kobayashi, Michio. Oxidation of thiols and sulfides by 2-aryl-1,2-benzisoselenazol-3(2H)-one 1-oxide. Sulfur Letters (1986), 5(1), 1-7.
10. Welter, Andre; Fischer, Hartmut; Christiaens, Leon; Wendel, Albrecht; Etschenberg, Eugen. 2,2-Diselenobis [benzamide]s of primary amines with glutathione peroxidase-like activity. Ger. Offen. (1986), 26 pp.
11. Dereu, Norbert; Welter, Andre; Wendel, Albrecht; Leyck, Sigurd; Parnham, Michael; Graf, Erich; Sies, Helmut. Glutathione derivatives and pharmaceuticals containing them. Ger. Offen. (1986), 17 pp.
12. Dereu, Norbert; Welter, Andre; Wendel, Albrecht; Leyck, Sigurd; Parnham, Michael; Graf, Erich; Sies, Helmut; Betzing, Hans; Fischer, Hartmut. S-(Carbamoylphenylselenyl) derivatives of glutathione and of aminomercaptocarboxylic acids and pharmaceutical preparations containing them. Eur. Pat. Appl. (1985), 22 pp.
13. Welter, Andre; Christiaens, Leon; Wirtz-Peitz. Benzisoselenazolinones and pharmaceutical preparations containing them. Eur. Pat. Appl. (1982), 30 pp.

Ebse 8

No references known for this exact structure at time of search

Ebse 9

1. Yang, Dongxu; Cheng, Guifang. Effects of seleno-organic compounds as antiinflammatory and antiallergic drugs. Zhongguo Yaoxue Zazhi (Beijing) (1996), 31(8), 470-473.
2. Welter, Andre; Fischer, Hartmut; Christiaens, Leon; Wendel, Albrecht; Etschenberg, Eugen. 2,2-Diselenobis[benzamide]s of primary amines with glutathione peroxidase-like activity. Ger. Offen. (1986), 26 pp.

Ebse 10

1. Liu, Yu; Li, Bin; Li, Li; Zhang, Heng-Yi. Synthesis of organoselenium-modified β-cyclodextrins possessing a 1,2-benzisoselenazol-3(2H)-one moiety and their enzyme-mimic study. Helvetica Chimica Acta (2002), 85(1), 9-18.
2. Mlochowski, Jacek; Gryglewski, Ryszard J.; Inglot, Anna D.; Jakubowsky, Andrzej; Juchniewics, Leszek; Kloc, Krystian. Synthesis and properties of 2-carboxyalkyl-1, 2-benzisoselenazol-3(2H)-ones and related organoselenium compounds as nitric oxide synthase inhibitors and cytokine inducers. Liebigs Annalen (1996), (11), 1751-1755.
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Xiao, Ying Xin; Liu, Xiu Fang; Xu, Han Sheng; Sun, Shi Yong; Xu, Bo. Synthesis and anti-lipid peroxidation activity of amino acid derivatives of Ebselen. Chinese Chemical Letters (1994), 5(8), 651-4.
5. Hatchett, R. J.; Gryglewski, R. J.; Mlochowski, J.; Zembowicz, A.; Radziszewski, W. Carboxyebselen, a potent and selective inhibitor of endothelial nitric oxide synthase. Journal of
Physiology and Pharmacology (1994), 45(1), 55-67.
6. Mlochowski, Jacek; Kloc, Krystian; Syper, Ludwik; Inglot, Anna D.; Piasecki, Egbert. Aromatic and azaromatic diselenides, benzisoselenazolones, and related compounds as immunomodulators active in humans: synthesis and properties. Liebigs Annalen der Chemie (1993), (12), 1239-44.

Ebse11

1. Wojtowicz, H.; Kloc, K.; Maliszewska, I.; Mlochowski, J.; Pietka, M.; Piasecki, E. Azaanalogs of ebselen as antimicrobial and antiviral agents: Synthesis and properties. Farmaco (2004), 59(11), 863-868.
2. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp
3. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
4. Blaszczyk, Barbara; Inglot, Anna D.; Kowalczyk-Bronisz, Stefania H.; Szymaniec, Stanislaw; Mlochowski, Jacek. Immunotropic activities of benzisoselenazolones and organic diselenides in mice. Archivum Immunologiae et Therapiae Exp. (1995), 43(5-6), 305-11.
5. Welter, Andre; Leyck, Sigurd; Etschenberg, Eugen. 1,2-Benzisoselenazolethiones and pharmaceutical preparations containing them. Ger. Offen. (1985), 27 pp.
6. Welter, Andre; Leyck, Sigurd; Etschenberg, Eugen. Benzisoseleniumazolones and pharmaceutical preparations containing them. Ger. Offen. (1984), 26 pp.

Ebse12

1. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp.

Ebse 13

1. Wang, Xiaoliang; Gou, Zongru; Lu, Jing; Chu, Fengming; Pan, Yaping; Wang, Ling. The use of benzisoselenazolone compounds against ischemic myocardial damage. PCT Int. Appl. (2003), 77 pp.
2. Inglot, Anna D.; Mlochowski, Jacek; Zielinska-Jenczylik, Janina; Piasecki, Egbert; Ledwon, Tomasz K.; Kloc, Krystian. Seleno-organic compounds as immunostimulants: An approach to the structure-activity relationship. Archivum Immunologiae et Therapiae Experimentalis (1996), 44(1), 67-75.
3. Welter, Andre; Leyck, Sigurd; Etschenberg, Eugen. 1,2-Benzisoselenazolethiones and pharmaceutical preparations containing them. Ger. Offen. (1985), 27 pp.
4. Welter, Andre; Leyck, Sigurd; Etschenberg, Eugen. Benzisoseleniumazolones and pharmaceutical preparations containing them. Ger. Offen. (1984), 26 pp.

Ebse14

1. Shi, Changjin; Yu, Lizhang; Yang, Fengguang; Yan, Jun; Zeng, Huihui. A novel organoselenium compound induces cell cycle arrest and apoptosis in prostate cancer cell lines. Biochemical and Biophysical Research Communications (2003), 309(3), 578-583.
2. Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830.
3. Zhao F, Yan J, Deng S, Lan L, He F, Kuang B, Zeng H. A thioredoxin reductase inhibitor induces growth inhibition and apoptosis in five cultured human carcinoma cell lines. Cancer. Lett. 2005 (in press)

Ebse 15

1. Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830

Ebse 16

1. Osajda, M.; Kloc, K.; Mlochowski, J.; Piasecki, E.; Rybka, K. Bisbenzisoselenazol-3(2H)-ones, a new group of ebselen analogues. Polish Journal of Chemistry (2001), 75(6), 823-830

Ebse 19

1. Wojtowicz, H.; Kloc, K.; Maliszewska, I.; Mlochowski, J.; Pietka, M.; Piasecki, E. Azaanalogs of ebselen as antimicrobial and antiviral agents: Synthesis and properties. Farmaco (2004), 59(11), 863-868.
2. Kloc, Krystian; Maliszewska, Irena; Mlochowski, Jacek. Synthesis of 7-azabenzisoselenazol-3(2H)-ones. A new group of selenium-containing antimicrobials. Synthetic Communications (2003), 33(21), 3805-3815.

Silver Antimicrobials

Silver has a long history to be used an antibacterial agent (10) and now it is still widely applied for the control of bacterial growth for the medical or non-medical purposes (11, 12). Silver antibacterial activity is known to be related to the reaction with thiols (10, 13), but the exact mechanism is not clear. Recently, silver has been shown to be involved in the disruption of multiple bacterial cellular processes, including disulfide bond formation, metabolism, and iron homeostasis, which are closely related to enhancement of production of reactive oxygen species (14).

See, U.S. Pat. Nos. 8,496,952; 4,150,026; 4,906,466; 5,364,649; 5,480,898; 5,736,591; 6,641,829; 6,444,726; 6,454,813; 6,461,386; 8,673,367; 8,524,796; 8,476,262; 8,466,146; 8,415,419; 8,350,049; 8,344,087; 8,343,536; 8,343,437; 8,338,358; 8,338,143; 8,329,690; 8,313,760; 8,273,685; 8,188,088; 8,129,328; 8,101,200; 8,084,535; 8,076,411; 8,067,519; 8,022,162; 7,998,653; 7,951,232; 7,939,500; 7,932,230; 7,888,514; 7,884,064; 7,884,037; 7,846,924; 7,824,557; 7,671,155; 7,667,046; 7,651,990;

7,648,943; 7,645,761; 7,585,980; 7,579,389; 7,569,564;
7,527,683; 7,488,822; 7,426,948; 7,351,838; 7,345,008;
7,316,738; 7,291,449; 7,264,951; 7,253,203; 7,219,988;
7,211,134; 7,132,012; 7,129,021; 7,118,844; 7,112,602;
7,098,174; 7,097,701; 7,091,234; 7,087,107; 7,084,168;
7,083,906; 7,081,457; 7,022,823; 7,008,990; 7,008,531;
6,982,261; 6,946,454; 6,927,199; 6,908,962; 6,841,568;
6,835,744; 6,811,711; 6,800,427; 6,794,373; 6,759,408;
6,750,187; 6,740,628; 6,733,113; 6,727,057; 6,723,692;
6,713,478; 6,710,017; 6,693,103; 6,683,036; 6,673,828;
6,656,456; 6,608,068; 6,583,145; 6,566,358; 6,562,857;
6,544,970; 6,528,467; 6,521,657; 6,509,334; 6,503,939;
6,498,154; 6,462,032; 6,444,668; 6,441,019; 6,436,929;
6,423,699; 6,417,214; 6,407,101; 6,399,593; 6,391,907;
6,380,235; 6,380,178; 6,369,056; 6,358,948; 6,358,947;
6,355,648; 6,344,218; 6,339,098; 6,329,416; 6,319,912;
6,306,851; 6,248,806; 5,965,150; 5,888,526; 5,804,591;
5,714,507; 5,597,841; 5,580,713; 5,576,151; 5,512,589;
5,449,593; 5,306,818; 5,288,595; 5,250,696; 5,223,525;
5,128,339; 4,940,134; 4,932,948; 4,766,113; 4,602,011;
4,244,966; 4,190,663; 4,156,729; 4,110,378; 3,975,155;
20080227766, 20140194627; 20140187783; 20140183398;
20140182483; 20140154808; 20140148339; 20140142213;
20140135252; 20140091031; 20140083324; 20140073548;
20140073030; 20140004331; 20130338105; 20130189516;
20130150239; 20130115263; 20130045241; 20130017582;
20120309063; 20120258900; 20120258507; 20120211031;
20120177713; 20120164203; 20120129955; 20120097194;
20120045624; 20120021358; 20120016063; 20110274893;
20110259571; 20110250626; 20110240064; 20110224170;
20110203018; 20110190122; 20110183842; 20110177950;
20110177147; 20110172099; 20110172098; 20110172097;
20110172096; 20110172095; 20110166021; 20110166020;
20110160056; 20110160055; 20110150961; 20110150956;
20110086397; 20110070376; 20110052656; 20110052655;
20110046088; 20110024355; 20110020914; 20100317515;
20100280427; 20100273651; 20100260813; 20100243221;
20100239679; 20100233146; 20100231670; 20100210745;
20100184633; 20100075939; 20100041292; 20100016198;
20100008961; 20100003431; 20090318495; 20090301382;
20090220749; 20090215944; 20090214606; 20090178212;
20090178211; 20090143478; 20090060973; 20090039035;
20090023103; 20080312367; 20080312366; 20080312365;
20080241732; 20080241557; 20080213608; 20080181950;
20080146484; 20080145664; 20080112909; 20080108115;
20070275945; 20070231295; 20070021528; 20060268086;
20060115440; 20060086841; 20060084573; 20060075921;
20060017792; 20060009357; 20050233925; 20050215773;
20050132927; 20050103709; 20050073563; 20050036982;
20040247655; 20040175407; 20040157763; 20040081911;
20040063021; 20040045478; 20040039180; 20040002021;
20030232288; 20030224303; 20030207217; 20030203136;
20030198907; 20030189013; 20030170306; 20030043238;
20030032569; 20020183222; 20020176879; 20020169090;
20020142931; 20020123443; 20020058216; 20020039982;
20020037822; 20020037817; 20020035051; 20010046946;
WO-A-01/00021; EP-A-0116865; EP-A-0251783; EP-A-1382248; EP-A-0251783; and EP-A-0734651, each of which is expressly incorporated herein by reference.

SUMMARY OF THE INVENTION

Investigation the antibacterial effects of the combination of silver and ebselen was conducted. The roles of bacterial Trx and GSH/Grx systems in the defense against the combination treatment were studied.

It is an object therefore to provide a method for treating a prokaryotic infection in an animal or human, comprising administering a source of silver, typically in ionized form, though optionally provided as a colloid or complex, e.g., organic complex, and at least one compound ebselen derivative.

Ebselen derivatives generally have the Formula I (and include ebselen itself), and pharmaceutically acceptable salts thereof:

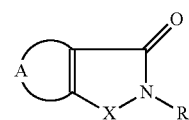

(I)

wherein X is selenium, and optionally adducts of the selenium (which may be active or prodrugs for the active ebselen derivative); in some cases, X can be S, with the proviso that the resulting ebselen derivative is an inhibitor of prokaryotic thioredoxin reductase having an $IC_{50}$ of less than about 25 μM, and exhibits an at least additive, and preferably synergistic inhibition of the thioredoxin reductase with a source of metal ions, and wherein R is hydrogen or an organic side chain, for example a side chain selected from the group consisting of:

alkyl having a carbon chain of 1 to 14 carbon atoms wherein the carbon chain is branched or unbranched which is optionally substituted with bensisoselenazol-3(2H)-one-2-yl, bensisotiazol-3(2H)-one-2-yl, OH, alkoxyl, SH, $NH_2$, N-alkylamino, N,N-dialkylamino, COOH, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, I, and heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, and wherein A represents an organic ring structure, for example a saturated, unsaturated or polyunsaturated 3 to 6 member carbon chain wherein N may optionally substitute for one or more carbons, and which is optionally substituted with one or more of OR, SR, and alkylamino, $C_1$-$C_5$ alkyl, OH, alkoxyl, SH, $NH_2$, N-alkylamino, N,N-dialkylamino, COOH, CHO, $NO_2$, F, Cl, Br, and I, or pharmaceutically acceptable derivatives thereof.

The present technology also encompasses administering to a human, animal, plant, or medium an ebselen derivative and a source of a metal ion, to achieve a synergistic inhibition of prokaryotic thioredoxin, e.g., of an organism infecting or colonizing the human, animal or plant, or prokaryotic organism in the medium. The ebselen derivative is selected and administered to achieve on a regular or continual basis, at least a concentration at or near the $IC_{50}$ for the ebselen derivative for the respective prokaryotic organism thioredoxin reductase. Because of the synergistic effect of the concurrently active metal ions, the dose can in some cases drop or remain below the $IC_{50}$, though typically it will be administered to achieve a concentration of at least 1% 5% or 10% of the $IC_{50}$. Typically, the administration of the pharmacological therapy and dose are designed to maintain continuous conditions of inhibition of bacterial growth, though this depends on the sensitivity of the organism to the combined therapy, which can be tested in a laboratory. The silver therapy may be provided in the same dosage form as the ebselen derivative, and in some cases in a molecular complex with the ebselen itself, but need not be. The silver therapeutic typically is limited by host toxicity, but in industrial uses a significant limitation may be cost or longevity of a source of the silver (or other metal ions). Such toxic limits are well known; note that in some cases, the ebselen derivative may alleviate heavy metal toxicity, and thus increase the acceptable dose and achieved concentration. However, in the case of silver, reactivity of the ions is also an issue, and the silver when administered to the organism may be sequestered away from the intended site of action, such as by precipitation with chloride, reduction to silver colloid, reaction with biomolecules, such as connective tissue, etc. Therefore, the dose of silver is typically set at a level beneath the acute toxic limit (except in cases of chronic administration, in which a maintenance dose should be set beneath the chronic toxic limit), based on the seriousness of the condition being treated to balance the potential side effects.

According to a method of treatment, a culture of an organism to be treated is obtained, and its sensitivity to one or more ebselen derivatives is ascertained, in a typical manner for determining antibiotic sensitivity for known and unknown organisms. Upon determination of the sensitivity of the organism to an ebselen derivative within a feasible clinical treatment concentration for the respective one or more ebselen derivatives, a further test may be optionally conducted to determine a synergy of silver, or other metal ion, in either reducing bacterial growth, or specifically on the respective bacterial thioredoxin. If such a study is performed, it can then determine an optimal range of the ebselen derivative and metal ion, and the range of effectiveness. Using known pharmacodynamic data, the therapy for a patient may then be defined. However, in a typical clinical setting, an ebselen derivative will be administered as a standard dose (range of mg/kg or mg/m$^3$), having a standard repetition (i.d. [per day], b.i.d. [twice per day], t.i.d. [3 times per day], q.i.d. [4 times per day], etc.). Therefore, the range of concentrations will generally be defined by the standard dosage forms, though the patient size may also be calculated to achieve a better estimate. As discussed above, the silver or metal ion therapy is also typically limited by avoidance of acute toxicity, and the actual tissue concentrations achievable or achieved may be variable over a range. Therefore, the investigation may often be reduced to the inquiry, is the concentration of ebselen derivative using standard dosage forms and administration, and the silver or metal ion concentration achievable using standard dosage forms and administration, sufficient to achieve, and optionally continuously maintain, conditions above the minimum inhibitory concentration for the bacteria in question? Under these circumstances, a limited number of laboratory tests might be conducted at the extremes of the conditions specified in the inquiry.

Note that the ebselen derivative is typically itself antibiotic, and therefore an ancillary question is whether the silver or metal ion therapy significantly improves efficacy of therapy of the ebselen derivative from a subtherapeutic range to a therapeutic range, for a target dose and administration mode.

The method may also comprise administering a thioredoxin reductase inhibitor antibiotic to a human, animal or plant in need of such treatment due to a bacterial infection or colonization, and concurrently administering an effective subtoxic dose of a source of metal ions sufficient to further inhibit the thioredoxin reductase activity of the bacteria causing the infection beyond the inhibition due to the thioredoxin reductase inhibitor antibiotic. Preferably, the thioredoxin reductase has a differential effect between eukaryotic thioredoxin reductase and prokaryotic thioredoxin reductase, selectively causing a greater degree of inhibition of the prokaryotic than eukaryotic type. The source of metal ions is preferably silver. The thioredoxin reductase inhibitor antibiotic is preferably a pharmaceutically acceptable (or flora-ceutically acceptable) benzoisoselenazol compound, e.g., ebselen derivatives.

A further object provides a method for inhibiting growth of a prokaryotic organism, comprising coadministering to an environment of the prokaryotic organism at least one benzoisoselenazol or a derivative, complex or salt thereof, the at least one benzoisoselenazol or a derivative, complex or salt thereof being a selective prokaryotic thioredoxin reductase inhibitor having a 50% inhibitory concentration ($IC_{50}$) of less than about 15 μM for $E.\ coli$ thioredoxin reductase; and an effective amount of at least metal ion, to achieve a dose-dependent 33% reduction in the inhibitory concentration ($IC_{50}$) for $E.\ coli$ thioredoxin reductase of the at least one benzoisoselenazol or a derivative, complex or salt thereof in the absence of the to least one metal ion. The benzoisoselenazol may comprise ebselen. The metal ion may comprise a silver ion. The benzoisoselenazol may act synergistically with the metal ion. The metal ion may be provided by an insoluble source of metal ions which release the metal ions for an extended duration at a constant rate.

A still further object provides method comprising: obtaining a microbiological sample; and determining a sensitivity of the microbiological sample to at least one pharmaceutically acceptable treatment comprising an ebselen derivative or salt or complex thereof, and silver ions. A patient may be treated based on the determined sensitivity with a therapy including the at least one pharmaceutically acceptable treatment. The ebselen derivative may be selected from the group consisting of EbSe2, EbSe3, EbSe4, EbSe5, EbSe6, EbSe7, EbSe8, EbSe9, EbSe10, EbSe11, EbSe12, EbSe13, EbSe14, EbSe15, EbSe16, and EbSe19. EbSe11 has a higher $IC_{50}$ than the other compounds, and therefore is not preferred on at least that basis. The ebselen derivative or salt or derivative may comprise a silver salt or a silver complex of the ebselen derivative.

As noted above, in some cases, the selenium may be replaced with sulfur, resulting in an ebsulfur derivative. As discussed below, most such compositions are ineffective to meet the criteria associated with an efficacious therapy. However, at least ebsulfur-23, the sulfur analog of ebselen-10, showed promise as a therapy in conjunction with metal ions, e.g., silver. Therefore, and object also provides a pharmaceutical formulation comprising ebsulfur-23.

U.S. Pat. No. 5,480,898 discloses storage-stable aqueous solutions of isothiazolin-3-ones comprising a noble metal ion, such as silver.

The ebselen derivatives are characterized in that they inhibit a prokaryotic thioredoxin reductase, while serving as a substrate for mammalian or eukaryotic thioredoxin reductase. In particular, the method generally seeks to employ an ebselen derivative that inhibits a thioredoxin reductase of a pathogenic bacteria or prokaryotic parasite, and acts as a substrate for a thioredoxin reductase of a eukaryote, e.g., human or mammal, to be treated. In some cases, the R group may be replaced with a silver anion which complexes with the resulting nitrogen cation, providing some similarities to silver sulfadiazine.

The two components need not be mixed or provided through the same route of administration. For example, the ebselen derivative may be administered orally and the silver composition administered topically.

In some cases, the composition is not employed as a medicine, and can be used as part of in industrial process. For example, in cell culture systems, the combination of ebselen and a silver ion source may be used to reduce bacterial contamination. Likewise, the compositions may be provided as part of a coating or slow release system to reduce or prevent biofilms.

The selection of the ebselen derivative employed may be based on sensitivity of the target organism, toxicity to the host organism (if there is one), pharmacodynamics or dynamics, cost, and the like.

The silver compounds may be, for example, silver salts, silver complex ions, colloidal silver, silver/zeolite composites, silver/phosphate, silver/glass particles (antimicrobial, controlled release), and mixtures thereof. Preferred silver salts are silver chloride, silver nitrate, silver acetate, silver benzoate, silver bromate, silver chlorate, silver lactate, silver molybdate, silver nitrite, silver(I) oxide, silver perchlorate, silver permanganate, silver selenate, silver selenite, silver sulfadiazine, silver sulfate, and mixtures thereof. Preferred silver complex ions are silver chloro complex ions, silver thiosulfato complex ions, or mixtures thereof. Preferred colloidal silver particles are silver nanoparticles The silver compounds may be present in an amount of silver content of about 0.01% by weight to about 75% by weight. Likewise, the ebselen derivative may be present in an amount of 0.1% to about 95% by weight. When administered systemically, the ebselen derivative is preferable maintained in a range below a system toxic dose, and above a minimum inhibitory concentration (MIC) for a target pathogen. However, the MIC is considered with respect to the coadministered silver.

The silver may be provided in a soluble or insoluble form, such as silver chloride, adsorbed on a support or particles selected from the group consisting of titanium oxide, magnesium oxide, aluminum oxide, silicon oxide, calcium oxide, barium oxide, calcium hydroxyapatite, chalk, natural ground or precipitated calcium carbonates, calcium magnesium carbonates, silicates, sheet silicates, zeolites, clays, bentonites and titanium oxide. The support material may have a particle size of less than 25 µm, e.g., <5 µm, or <1 µm, or <120 nm, or <25 nm, or <25 nm. Insoluble silver on a support material is useful for non-medical applications and topical application, for example.

The composition may also include an effective amount of a dispersant, such as polynaphthalenesulfonate, naphthalenesulfonate or alkyl sulfosuccinate, e.g., in an amount of about 0.1 to 40% by weight.

The composition may further include an isothiazoline derivative. See, U.S. Pat. Nos. 8,496,952, 5,364,649, and 4,150,026.

The silver may be in the form of compound such as silver chloride, silver bromide, silver iodide, silver nitrate, $Ag_3PO_4$, $Ag_2SO_4$, $Ag_2CO_3$, silver citrate, silver stearate, silver acetate, silver lactate, silver salicylate, silver oxide (silver hydroxide), preferably silver chloride, silver citrate and silver nitrate. In some cases, colloidal silver may be employed.

The composition may be administered as a pharmaceutical for use in animals or on plants, or as an industrial microbiocide. The route of administration may be topical (as a cream, ointment, lavage, powder, or bandage or packing), orally, especially the ebselen derivative component, rectally or intravaginally, intravenously, intraperitoneally, or through other known routes of administration. The composition is preferably provided in a pharmaceutically acceptable formulation, having concentrations of the respective components that are below the acute toxic dose, especially when provided in unit dosage form.

The benzisoselenazolonyl derivatives according to the present invention or their salts may be administered in form of pure substance or proper pharmaceutical composition comprising the ebselen derivatives, as an active agent optionally in combination with other agents, via any acceptable administration route. Therefore, the invention also includes a pharmaceutical composition comprising the benzisoselenazolonyl derivatives or their pharmaceutically acceptable salts and pharmaceutically acceptable excipient or carrier, which can be used for treating bacterial and certain other prokaryotic infections.

The ebselen derivatives can be administered by a number of routes, including but not limited to orally, intranasally, rectally, vaginally, buccally, transdermally, or parenterally, in form of solid, semi-solid, micronized powder, lyophilized powder, or liquid. For example, the composition can be used in the form of tablet, suppository, pill, soft and hard gelatin capsule, granule, solution, suspension or aerosol. Preferred is single unit form for exact dosage. The pharmaceutical composition includes conventional excipient or carrier and one or more ebselen derivatives. The composition may additionally contain other therapeutic agent and the like. The composition may include silver or a silver compound, or silver or a silver compound may be administered separately. The silver or silver compound is preferably water-soluble, nanoscale particles, or a nanoscale layer of silver on micron scale particles.

Generally, depending on the mode of administration, the pharmaceutically acceptable composition may comprise 1 to 99% by weight of the ebselen derivative as active agent and 99 to 1% by weight of appropriate pharmaceutical excipient. If provided together, the silver content may be 0.01% to about 75%. The preferred composition comprises about 5 to 75% by weight of ebselen derivative compound, and the other is appropriate excipient or carrier and/or other therapeutic agent, e.g., silver or silver compound.

Preferred administration route is by intravenous injection, using conventional daily dosage protocol, which may be adjusted according to the severity of the illnesses. The compounds or their pharmaceutically acceptable salts can be formulated into dosage form for injection, for example, dispersing about 0.5 to 50% by weight of the ebselen derivative as an active agent in liquid excipient or carrier, such as water, saline, aqueous glucose solution, ethanol and glycerol, to for a solution or suspension.

The pharmaceutical composition, which can be administered in form of a solution or suspension, can be obtained, for example, by dissolving or dispersing the ebselen derivatives (for example, about 0.5 to 20% by weight) and optionally other adjuvants in carriers, including but not limited to water, saline, aqueous glucose solution, ethanol and glycerol solution. For intravenous administration, a soluble silver salt is preferred, in an amount of 0.01% to 10%, and preferably <1% by weight.

Further, if necessary, the pharmaceutical composition according to the invention may include the assistant substances, such as wetting agent or emulsifier, pH buffer, antioxidant and the like. The particular examples are citric acid, sorbitan monolaurate, triethanolamine oleate, butylated hydroxybenzene and the like.

The ebselen or bisbenzisoselenazolonyl derivatives may be administered together with, before or after the source of silver ions. Other antimicrobial agents may also be employed concurrently, before or after. One or more ebselen derivatives may be administered through the same route of administration or a different route of administration as the source of silver ions.

In some cases, the source of silver ions is produced electrochemically on a continual basis from a reduced silver or otherwise sequestered source. This is especially suitable to provide in the source of a silver ion producing topical bandage. In other cases, an implant can be provided, with a self-contained or energy harvesting power source. Alternately, s slow release system or polymer may be provided to generate a continuous low level of silver ions. For example, a polylactic acid block with a soluble silver salt or an organo-silver compound may be provided.

In some cases, another noble metal, such as gold or copper may be administered or coadministered. See, U.S. Pat. No. 8,425,880, expressly incorporated herein by reference.

In some embodiments, an area to be treated includes an oral cavity, a gastrointestinal tract, a nasal cavity, a respiratory tract, an ulceration, a connective tissue, and/or a wound.

In some embodiments, the one or more silver-containing materials are bactericidal and/or sporicidal. The one or more silver-containing materials can include, but are not limited to, silver, silver oxide, silver nitrate, an atomically disordered silver-containing material and/or nanocrystalline silver.

In some embodiments, contacting the area with one or more silver-containing materials includes oral administration, inhalation, rectal administration, intravaginal administration, intravessicular administration, and/or topical administration of the one or more silver-containing materials. In some embodiments, the method further includes contacting the area with one or more non-metal antibiotic medications, in addition to the ebselen derivative. The one or more non-metal antibiotic medications can include vancomycin, metronidazole, benzoxazinorifamycin, and/or rifaximin. The one or more non-metal antibiotic medications can be contacted to the area before, after, or simultaneous with contacting the area with the one or more silver-containing materials.

In some embodiments, the one or more silver-containing material is contacted with the area at a dose of from 0.1 to 1000 mg/kg or from 0.1 to 10,000 mg, and/or at a frequency of from one to four times per day. In some embodiments, the non-metal antibiotic medication is contacted with the area at a dose of from 50 to 4000 mg/kg or from 50 to 4000 mg, and/or at a frequency of from one to four times per day.

In some embodiments, the one or more silver-containing materials includes a controlled-release composition (e.g., a composition having controlled-release properties, a coated controlled-release composition, an enteric composition, an enteric-coated composition), a solution, a nanodispersion, an aerosol, a cream, and/or a gel. The controlled-release composition can include a suspension, a capsule, a tablet, and/or a pill. In some embodiments, the controlled-release composition includes a bead that includes from 0.01 to 20 percent by weight of the one or more silver-containing materials. The bead can be coated with the one or more silver-containing material and/or a controlled-release coating. The bead can include sugar or starch. The bead can have a maximum average dimension of from 0.5 to 2 mm.

In some embodiments, the article can include a suspension, a capsule, a tablet, and/or a pill. The article can include one or more metal-containing materials, such as an atomically disordered metal-containing material, and/or an atomically disordered, nanocrystalline metal-containing material. In some embodiments, the article including the one or more metal-containing material can include silver-containing materials, gold-containing materials, platinum-containing materials, palladium-containing materials, copper-containing materials, and/or zinc-containing materials. For example, the one or more metal-containing materials can include nanocrystalline silver, and/or an atomically disordered, nanocrystalline silver. As an example, the one or more metal-containing materials can include silver oxide.

In some embodiments, the article includes from 0.01 to 20 percent by weight of the controlled-release coating, which can include beeswax, beeswax and glyceryl monostearate, shellac and cellulose, cetyl alcohol, mastic and shellac, shellac and stearic acid, polyvinyl acetate and ethyl cellulose, neutral copolymer of polymethacrylic acid ester (Eudragit L30D), copolymer of methacrylic acid and methacrylic acid methylester (Eudragits), neutral copolymers of polymethacrylic acid esters containing metallic stearates, and/or neutralized hydroxypropyl methylcellulose phthalate polymer.

In some embodiments, the metal-containing material is both sporicidal and bactericidal. Hence, the metal-containing material can kill both the bacteria and bacterial spores of an infected area, and can thereby decrease the likelihood of recurrence of a bacterial infection by decreasing the number of viable spores. In some embodiments, the metal-containing material can interfere with germination of the bacterial spores. In some embodiments, infection of an area of a subject does not occur within a year (e.g., within six months, within three months, or within one month) of a conclusion of treatment with a therapeutic agent, such as a metal-containing material, or a metal-containing material and an ebselen derivative. In some embodiments, a combination treatment with a metal-containing material and an ebselen derivative antibiotic medication is more effective in killing bacteria and bacterial spores than a treatment with either a metal-containing material or a non-metal antibiotic medication. In some embodiments, continuous or intermittent treatment including a metal-containing material is less likely to result in resistant strains of bacteria and/or bacterial spores over a period of time (e.g., greater than three months, greater than six months, greater than one year, greater than two years) than a treatment without a metal-containing material (e.g., with a non-metal antibiotic medication).

In some embodiments, the composition (e.g., a cream) is an anti-microbial barrier. The composition can be anti-inflammatory.

The silver may be provided, for example, as nanocrystalline silver dispersions with polyvinyl alcohol (PVA) or lecithin (LEC) used as dispersant, administrable at doses of 40 or 8 mg/kg/day.

In some embodiments, the area of a subject affected with a condition having bacteria and/or bacterial spores is treated with a therapeutically effective amount of one or more metal-containing materials. Treatment can continue until the condition ameliorates or disappears. As used herein, a therapeutically effective amount refers to an amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptoms of the disease; or decreasing the likelihood of a relapse of a disease, condition, or disorder in an individual;

(2) inhibiting the disease; for example, inhibiting a disease, condition or disorder in an individual who is experiencing or displaying the pathology or symptoms of the disease, condition or disorder (i.e., arresting further development of the pathology and/or symptoms) such as lowering the bacterial load in the case of a bacterial infection, and (3) ameliorating the disease; for example, ameliorating a disease, condition or disorder in an individual who is experiencing or displaying the pathology or symptoms of the disease, condition or disorder (i.e., reversing the pathology and/or symptoms) such as reducing infection-related tissue damage in the case of a bacterial infection.

The metal-containing material can be contacted to an area in a variety of forms. For example, a dressing containing an appropriate metal-containing material (e.g., antimicrobial, atomically disordered, silver-containing material) can be applied to an area of the skin having a condition. As another example, a controlled-release composition containing an appropriate metal-containing material can be contacted with an area (e.g., a gastrointestinal area) having a condition, by ingesting the controlled-release composition. As another example, an aerosol containing an appropriate metal-containing materials can be contacted with an area (e.g., a respiratory area) having a condition, by breathing in the aerosol. As a further example, a metal-containing material can be contacted with the area having a condition (e.g., a systemic condition) by injecting a solution including a metal-containing material.

Moreover, while the foregoing has described embodiments that involve one method of contacting a subject with the metal-containing material, in other embodiments, more than one method of contacting a subject with the metal-containing material can be used. For example, the methods can include one or more of ingestion (e.g., oral ingestion), injection (e.g., using a needle, using a needleless injector), topical administration, inhalation (e.g., inhalation of a dry powder, inhalation of an aerosol) and/or application of a dressing. The methods for application of a metal-containing material to the subject can vary in a number of ways, generally depending upon the form of the material as applied and/or the location of the condition to be treated. In general, the amount of material used is selected so that the desired therapeutic effect (e.g., reduction in the condition being treated) is achieved while the material introduces an acceptable level of toxicity (e.g., little or no toxicity) to the subject. Generally, the amount of the material used will vary with the conditions being treated, the stage of advancement of the condition, the age and type of host, and the type, concentration and form of the material as applied. In some embodiments, a single application of the material may be sufficient. In certain embodiments, the material may be applied repeatedly over a period of time, such as several times a day for a period of days, weeks, months or years.

Furthermore, while the foregoing has described embodiments in which one form of the metal-containing material is used, in other embodiments, more than one form of the metal-containing material can be used. For example, the methods can include using the metal-containing material in the form of a controlled-release composition, a coating (e.g., a dressing), a free standing powder, a freeze-dried powder, a solution and/or a pharmaceutical carrier composition.

In some embodiments, the ebselen derivative and silver-containing material is disposed in a hand sanitizer, or in a disinfectant spray, and can be applied to a surface of interest to reduce and/or prevent bacterial/bacterial spore growth.

Moreover, the ebselen derivative and silver-containing material can be used in various industrial applications. For example, it can be used to reduce and/or prevent microbial growth on industrial surfaces (e.g., industrial surfaces where microbial growth may occur, such as warm and/or moist surfaces). Examples of industrial surfaces include heating pipes and furnace filters. In certain embodiments, the metal-containing material can be disposed (e.g., coated or sprayed) on the surface of interest to reduce and/or prevent microbial growth. This can be advantageous in preventing the spread of microbes via, for example, heating and/or air circulation systems within buildings.

In general, treatment and/or inhibition of conditions having bacteria/bacterial spores involves contacting the metal-containing material with the area of the body having the condition. As an example, a condition can be inhibited and/or treated by contacting the area having the condition with a controlled-release composition, a coating (e.g., a dressing), a free standing powder, a freeze-dried powder, a solution and/or a pharmaceutical carrier composition containing the metal-containing material.

In some embodiments, treatment and/or inhibition of conditions can involve contacting the metal-containing material with the area of the body having the condition in combination with one or more non-metal antibiotic medications, e.g., the ebselen derivative which may be supplemented with an additional antibiotic. Examples of other non-metal antibiotic medications include vancomycin, metronidazole, benzoxazinorifamycin, and/or rifaximin. Treatment with the non-metal antibiotic medications different from the metal-containing material can occur before, after, or simultaneously with treatment with metal-containing material. The non-metal antibiotic medication can be administered to a subject in a variety of ways that can be the same as or different from the anti-microbial material.

The dose when using the metal-containing material and/or the non-metal antibiotic medication can vary within wide limits, and as is customary and is known to the physician, it is to be tailored to the individual conditions in each individual case. It depends, for example, on the nature and severity of the illness to be treated, on the condition of the patient, on the therapeutic agent(s) employed or on whether an acute or chronic disease state is treated or prophylaxis is conducted or on whether further therapeutic agents are administered in addition to the silver-containing material and/or ebselen derivative medication.

In some embodiments, the metal-containing material, e.g. silver ion, is administered at a dose of from 0.05 milligram (mg) to 1.5 gram (g) (e.g., from 0.1 mg to 1.0 g, from 0.1 g to 0.5 g, or from 0.5 g to 1.0 g). In some embodiments, the metal-containing material is administered at a dose of at least 0.05 mg (e.g., at least 0.1 mg, at least 100 mg, at least 500 mg, or at least 800 mg) and/or at most 1.5 g (e.g., at most one gram, at most 800 mg, at most 500 mg, at most 100 mg, or at most 0.1 mg).

In some embodiments, the ebselen derivative medication is administered at a dose of from 1 mg to four grams (e.g., from 25 mg to three grams, from 100 mg to two grams, from one to two grams). In some embodiments, the ebselen derivative medication is administered at a dose of at least 40 mg (e.g., at least 100 mg, at least 500 mg, at least one gram, at least two grams, or at least three grams) and/or at most four grams (e.g., at most three grams, at most two grams, at most one gram, at most 500 mg, or at most 100 mg).

In some embodiments, the combination can be administered to a subject (e.g., a human subject) at a frequency of at least one dose per day (e.g., at least one dose per 12 hours, or at least one dose per 6 hours) and/or at most one dose per three hours (e.g., at most one dose per six hours, or at most one dose per 12 hours). In some embodiments, the silver-containing material and/or ebselen derivative antibiotic medication are administered to a subject (e.g., a human subject) at a frequency of from one dose per day to one dose per three hours (e.g., from one dose per day to one dose per six hours, from one dose per day to one dose per 12 hours). The metal-containing material and/or non-metal antibiotic medication can contact the area continuously, or for a duration of about one hour per dose (e.g., about a half hour per dose, about 15 minutes per dose, about five minutes per dose, about one minute per dose).

In some embodiments, a treatment cycle with the metal-containing material and/or the non-metal antibiotic medication can last at least one day (at least three days, at least one week, or at least two weeks) and/or at most one month (e.g., at most two weeks, at most one week, or at most three days). In some embodiments, a treatment cycle with the metal-containing material and/or the non-metal antibiotic medication can last from one day to two months (e.g., from one day to one month, from one day to two weeks, from one day to one week, or from one to three days). As used herein, a treatment cycle refers to length of time at which the active compound or pharmaceutical agent achieves the biological or medicinal response that is being sought in a tissue, system, animal, individual or human by a researcher, veterinarian, medical doctor or other clinician.

In some embodiments, when the condition having bacteria and/or bacterial spores is treated with the metal-containing material in conjunction with an non-metal antibiotic medication, the treatment cycle with the metal-containing material can start at the same time as, before, and/or after a treatment cycle with the non-metal antibiotic medication. In some embodiments, the treatment cycle with the metal-containing material overlaps with the treatment cycle with a non-metal antibiotic medication. For example, the treatment cycle with the metal-containing material at a prescribed dose and frequency can start at most a month (e.g., at most two weeks, at most a week, at most three days, or at most a day) and/or at least a day (at least three days, at least a week, or at least two weeks) in advance of, or after, the start of a treatment cycle with the non-metal antibiotic medication.

In some embodiments, when the condition having a bacteria and/or a bacterial spores is treated with the silver-containing material in conjunction with one or more non-metal antibiotic medications including an ebselen derivative, delivery of each dose of the metal-containing material can occur at the same time as, before, or after delivery of a dose of non-metal antibiotic medication. The doses of the metal-containing material and the non-metal antibiotic medication can be the same or different. The dose delivery frequency of the metal-containing material and the non-metal antibiotic medication can be the same or different.

In some embodiments, the microbial conditions to be treated are characterized by the presence of bacterial (e.g., sporulating bacteria) biofilms. A biofilm is a complex aggregation of bacteria, which secrete a protective and adhesive matrix. Biofilms can attach to a surface, and exhibit structural heterogeneity, genetic diversity, complex community interactions, and an extracellular matrix of polymeric substances. Biofilm conditions can be the cause of persistent and chronic infections, and can affect a variety of tissues such as the gum and jawbone (periodontal tissue), the eye (e.g., infection by contact lenses having biofilms), the lung (e.g., chronic lung infections), the gastrointestinal tract, internal tissue (e.g., endocarditis) and the skin (e.g., infected skin, infected burn wounds). Biofilms can also form on medical devices implanted in the body such as catheters and heart valves, or on contact lenses.

In general, treatment and/or inhibition of microbial conditions involves contacting the metal-containing material with the area of the body having the condition. As an example, a microbial condition can be inhibited and/or treated by contacting the area having the condition with a formulation such as a controlled-release composition, a cream, a foam, a gel, a lotion, a paste, an ointment, a nanodispersion, and/or a solution containing the metal-containing material.

In some embodiments, the microbial condition can be treated and/or prevented by contacting the metal-containing material with the area of the body or device having a microbial condition and/or susceptible to the formation of a microbial condition. As an example, a microbial condition (e.g., a biofilm condition) can be treated and/or prevented by contacting or coating the susceptible area or device with a formulation such as a controlled-release composition, a cream, a foam, a gel, a lotion, a paste, an ointment, a nanodispersion, and/or a solution containing the metal-containing material. In some embodiments, for an internal administration, the formulation can have a metal-containing material administered at a metal dosage, e.g., silver, of at least 0.1 mg of a metal-containing material per one kg of a subject (e.g., at least 0.4 mg/kg, at least 40 mg/kg, or at least 400 mg/kg) and/or at most 1000 mg/kg (e.g., at most 400 mg/kg, at most 40 mg/kg, or at most 0.4 mg/kg), and for a period sufficient to treat/alleviate/cure the condition. For example, the metal dosage can be from 0.1 to 10,000 mg (e.g., e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material per one kg of a subject. In some embodiments, for a topical administration, the formulation can have a metal-containing material administered at a metal dosage of at least 0.1 mg of a metal-containing material (e.g., at least 0.4 mg, at least 40 mg, or at least 400 mg) and/or at most 10,000 mg (e.g., at most 5,000 mg, at most 1,000 mg, at most 400 mg, at most 40 mg, or at most 0.4 mg), and for a period sufficient to treat/alleviate/cure the condition. In some embodiments, the metal dosage is from 0.1 to 10,000 mg (e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material. In some embodiments, for a 70 kg person, at least 20 mg (e.g., at least 50 mg, at least 100 mg, at least 200 mg, at least 300 mg, at least 400 mg, or at least 500 mg) and/or at most 600 mg (e.g., at most 500 mg, at most 400 mg, at most 300 mg, at most 200 mg, at most 100 mg, or at most 50 mg) of a metal-containing material is administered per single dose, or from 20 to 600 mg (e.g., from 50 to 500 mg, from 50 to 400 mg, from 20 to 400 mg, from 20 to 300 mg, from 20 to 200 mg) of a metal-containing material is administered per single dose.

The formulation can be administered to a subject (e.g., a human subject) at a dosage of at least one dose per day (e.g., at least one dose per 12 hours, or at least one dose per 6 hours) and/or at most one dose per three hours (e.g., at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours). The formulation can contact the area continuously, or for a duration of about one hour (e.g., about a half hour, about 15 minutes, about five minutes, about one minute).

In some embodiments, e.g., for a gastrointestinal condition, the condition can be treated using by orally administering a formulation of metal-containing material, and/or by rectally administering a suppository and/or an enema including the metal-containing material. For example, the formulation can be a controlled-release composition (e.g., a tablet, pill, capsule, or bead having controlled-release properties and/or a controlled-release coating, an enteric-coated tablet, an enteric-coated pill, an enteric-coated capsule, a suspension including an enteric-coated bead), a nanodispersion, or a suppository having a metal-containing material administered at a metal dosage of at least 0.1 mg of a metal-containing material per one kg of a subject (e.g., at least 0.4 mg/kg, at least 40 mg/kg, or at least 400 mg/kg) and/or at most 1000 mg/kg (e.g., at most 400 mg/kg, at most 40 mg/kg, or at most 0.4 mg/kg), and for a period sufficient to treat/alleviate/cure the condition. In some embodiments, the metal dosage is from 0.1 to 10,000 mg (e.g., from 0.1 to 5,000 mg, from 0.1 to 1,000 mg, from 0.4 to 1000 mg, from 0.4 to 400 mg, from 0.4 to 40 mg, from 40 to 400 mg) of metal-containing material per one kg of a subject. In some embodiments, for a 70 kg person, at least 20 mg (e.g., at least 50 mg, at least 100 mg, at least 200 mg, at least 300 mg, at least 400 mg, or at least 500 mg) and/or at most 600 mg (e.g., at most 500 mg, at most 400 mg, at most 300 mg, at most 200 mg, at most 100 mg, or at most 50 mg) of a metal-containing material is administered per single dose, or from 20 to 600 mg (e.g., from 50 to 500 mg, from 50 to 400 mg, from 20 to 400 mg, from 20 to 300 mg, from 20 to 200 mg) of a metal-containing material is administered per single dose. In some embodiments, the formulation can take the form of an enema having a volume of about 60 ml (about 30 ml, about 40 ml, about 50 ml, about 70 ml, about 80 ml, or about 90 ml). The formulation can be administered to a subject at a dosage of at least one dose per day (e.g., at least one dose per 12 hours, or at least one dose per 6 hours) and/or at most one dose per three hours (e.g., at most one dose per six hours, or at most one dose per 12 hours). In some embodiments, the formulation is administered to a subject (e.g., a human subject) at a dosage of from one dose per day to one dose per three hours (e.g., from one dose per day to one dose per six hours, from one dose per day to one dose per 12 hours).

In some embodiments, for a circulatory and/or a systemic condition, the condition can be treated by injecting (e.g., via a small needle injector, via an intravenous needle) a nanodispersion and/or a solution containing the metal-containing material into the subject. As another example, certain circulatory and/or systemic conditions can be treated by injecting (e.g., via a needleless injector) a powder (e.g., a freeze-dried powder, a free standing powder) of the metal-containing material into the subject. As a further example, certain circulatory and/or systemic conditions can be treated by orally administering a metal-containing material. Areas of the circulatory system include, for example, the heart, the lymphatic system, blood, blood vessels (e.g., arteries, veins).

In certain embodiments, the circulatory and/or systemic condition is a bacterial and/or bacterial spore circulatory condition, a biofilm circulatory condition, a microbial circulatory condition, an inflammatory circulatory condition, an autoimmune circulatory condition, and/or an idiopathic circulatory condition. As referred to herein, circulatory conditions include lymphatic conditions. Examples of circulatory and/or systemic conditions include gas gangrene, tetanus, septicemia, leukemia, and lymphangitis.

In general, the treatment of respiratory conditions involves contacting the metal-containing material with the area of the respiratory system having the condition. Areas of the respiratory system include, for example, the oral cavity, the nasal cavity, and the lungs. As an example, certain respiratory conditions can be treated by inhaling a free standing powder and/or a freeze-dried powder of the metal-containing material (e.g., with a dry powder inhaler). As another example, certain respiratory conditions can be treated by inhaling a nanodispersion and/or solution containing the metal-containing material (e.g., in the form of an aerosol with an inhaler). The nanodispersion and/or solution can have a near-neutral pH. In some embodiments, when the nanodispersion and/or solution is in the form of an aerosol, the aerosol includes droplets having a diameter from 0.1 to 10 µm (e.g., from 0.1 to one µm, from one to five µm, or from five to 10 µm). The droplet size of an aerosol can determine how far down the respiratory tree the droplet travels. For example, a 10 µm droplet can pass the larynx and penetrate the trachea and bronchial regions of a lung, and settle at the pulmonary bifurcations. Droplets having a diameter of 0.1 to 2.5 µm can enter the nonciliated alveolar regions and deposit deep into the lungs of a subject.

The respiratory condition can be a bacterial and/or bacterial spore respiratory condition, a biofilm respiratory condition, a microbial respiratory condition, an inflammatory respiratory condition, an autoimmune respiratory condition, and/or an idiopathic respiratory condition. Examples of respiratory conditions include anthrax infection, bronchitis, pulmonary edema, acute respiratory distress syndrome, bronchopulmonary dysplasia, fibrotic conditions (e.g., pulmonary fibrosis), tuberculosis, pneumonia, sinusitis, allergic rhinitis, pharyngitis, mucositis, stomatitis, chronic obstructive pulmonary disease, bronchiectasis, lupus pneumonitis, and/or cystic fibrosis.

Generally, the treatment of skin or integument conditions involves contacting the metal-containing material with the area of the skin having the condition. As an example, a skin or integument condition can be treated by contacting the area of skin having the condition with a dressing having a coating of the metal-containing material. As another example, a skin or integument condition can be treated by contacting the area of skin having the condition with a nanodispersion/solution containing the metal-containing material. As an additional example, a skin or integument condition can be treated by contacting the area of skin having the condition with a pharmaceutical carrier composition containing the metal-containing material, such as a cream, a foam, a gel, a lotion, a paste, an ointment, a nanodispersion and/or a solution. Treatment can continue until the condition is cured or ameliorated. In some embodiments, when the condition is anthrax, gas gangrene, or tetanus, the material may be applied to the affected skin area in the form of foam, gel, lotion, paste, and/or ointment at a concentration of from 100 µg to 20000 µg metal-containing material per gram of the formulation; or nanodispersion and/or solution that can include the metal-containing material at a concentration of from 100 µg to 20000 µg per ml of the formulation. In some embodiments, the nanodispersion and/or solution can include from one µg to 100 µg (e.g., from one µg to 50 µg, from one µg to 25 µg, from 50 µg to 100 µg) metal-containing material per ml of the formulation. A topical administration can kill the spores and bacteria at an area of skin such that the infection does not become systemic. In some embodiments, the formulation can include liposomes, micelles, or vesicles intended to improve the penetration of the silver through epidermal and dermal tissue.

The skin condition or an integument condition can be a bacterial and/or bacterial spore skin condition, a biofilm skin condition, an inflammatory skin condition, an autoimmune skin condition, an idiopathic skin condition, a microbial integument condition, an inflammatory integument condition, an autoimmune integument condition, and/or an idiopathic integument condition. Examples of skin conditions or integument conditions include burns, pyoderma gangrenosum, erythema multiforme, rosacea, acne (e.g., acne vulgaris, neonatal acne, infantile acne, pomade acne), Reiter's syndrome, gas gangrene, tetanus, anthrax, ulcer and erosion due to cutaneous trauma (e.g., diabetic foot ulcer).

In some embodiments, the formulation is a controlled-release composition. The controlled-release formulation can be designed to selectively release a therapeutic agent in a desired area of the small and/or large intestines, and/or gradually release the therapeutic agent over a selected area of the small and/or large intestines. The controlled-release composition can include articles (e.g., beads, tablets, pills, capsules) including a therapeutic agent (e.g., one or more metal-containing materials and/or one or more non-metal antibiotic medications). The articles can be coated with a controlled-release coating. The controlled-release coating provides a protective barrier for the therapeutic agent against acidic environments (e.g., the stomach) so that the formulation passes through the stomach with little (e.g., no) therapeutic agent being released, and so that the therapeutic agent is relatively easily released in less acidic environments (e.g., the intestines, the colon). In some embodiments, the controlled-release coating can control the release the therapeutic agent in a desired area of the small and/or large intestines, and/or gradually release the therapeutic agent over a selected area of the small and/or large intestines.

In some embodiments, the controlled-release composition includes a controlled-release bead (e.g., a bead having controlled-release properties and/or a controlled-release coating, an enteric-coated bead). In general, the bead can have a variety of cross-sectional shapes, such as a circle, an ellipse, a regular polygon (e.g., a square, a diamond, a pentagon, a hexagon, or an octagon), and/or an irregular polygon. For example, in some embodiments, the bead is a sphere and has a circular cross-section. The bead can have a maximum average dimension (e.g., a diameter) of from 0.1 to three mm (e.g., from 0.5 to two mm, from 0.5 to one mm, or from one to two mm). In some embodiments, the bead can have a maximum average dimension of at least 0.1 mm (e.g., at least 0.5 mm, at least one mm, at least 1.5 mm, at least two mm) and/or at most three mm (e.g., at most two mm, at most 1.5 mm, at most one mm, or at most 0.5 mm). The maximum average dimension of a bead is determined by measuring the maximum dimension of each bead in a population of beads (e.g., 10, 20, or 50 beads), adding the maximum dimension of each bead, and dividing the sum by the number of measured beads.

In some embodiments, the controlled-release bead has a core that includes a biocompatible and/or bioabsorbable material such as a carbohydrate (e.g., sugar, starch, sodium carboxymethylcellulose, cellulose, alginates, and/or sodium starch glycolate).

In some embodiments, the core is coated with a therapeutic agent, such as a silver-containing material and/or an ebselen derivative. In some embodiments, the therapeutic agent is uniformly or non-uniformly distributed throughout the core. For example, the therapeutic agent remains at a constant concentration, or can increase or decrease in concentration from the periphery of the bead to the center of the core. The controlled-release bead can include from 0.01 to 20 percent by weight (e.g., from 0.05 to 20 percent, from one to 20 percent, from 0.05 to 10 percent, or from 0.05 to five percent) of the therapeutic agent (e.g., a metal-containing material and/or a non-metal antibiotic medication). In some embodiments, the controlled-release bead can include at least 0.01 percent by weight (e.g., at least 0.05 percent by weight, at least 0.1 percent by weight, at least 0.5 percent by weight, at least one percent by weight, at least five percent by weight, at least 10 percent by weight, or at least 15 percent by weight) and/or at most 20 percent by weight (at most 15 percent by weight, at most 10 percent by weight, at most five percent by weight, at most one percent by weight, at most 0.5 percent by weight, at most 0.1 percent by weight, or at most 0.05 percent by weight) of the therapeutic agent.

The controlled-release bead can have a surface covered with a controlled-release coating (e.g., an enteric coating). The coating can include a material that is stable in acidic environments, but that disintegrates relatively rapidly in less acidic environment. Examples of controlled-release coatings include beeswax, beeswax and glyceryl monostearate, shellac and cellulose, cetyl alcohol, mastic and shellac, shellac and stearic acid, polyvinyl acetate and ethyl cellulose, neutral copolymer of polymethacrylic acid ester (Eudragit L30D), copolymer of methacrylic acid and methacrylic acid methylester (Eudragits), neutral copolymers of polymethacrylic acid esters containing metallic stearates, neutralized hydroxypropyl methylcellulose phthalate polymer, and/or combinations thereof.

In some embodiments, the controlled-release composition can include more than one type of controlled-release beads, each type having any combination of therapeutic agent, maximum average dimension, concentration, distribution of therapeutic agent, core materials, and/or coating materials.

In some embodiments, the controlled-release beads are made by forming a granulated wet mixture of core materials (e.g., a carbohydrate), a binder and/or a therapeutic agent, extruding the mixture, and forming beads by placing the extrudate into a spheronizer. In some embodiments, a bead having a core without any therapeutic agents can be sprayed with a solution and/or a dispersion (e.g., a nanodispersion) of a therapeutic agent. The weight percent of the therapeutic agent can be determined by measuring the bead before and after coating, or by pre-measuring the mass of each component of a bead prior to forming a mixture of core materials. Methods for making coated compositions are described, for example, in Garcia et al., U.S. Pat. No. 7,217,429, and Ullah et al., U.S. Pat. No. 6,224,910, expressly incorporated herein by reference. In some embodiments, the bead cores are commercially available (e.g., from Chr. Hansen, Denmark).

In some embodiments, the controlled-release beads are pressed into a tablet or a pill, encapsulated in a capsule, or suspended in a solution to form a suspension. In some embodiments, a tablet, pill, or capsule can be formed directly from a therapeutic agent and any of a number of excipients, binders, and/or fillers. The tablet, pill, or capsule can contain varying percentage amounts of the therapeutic agents and carriers. For example, the tablet, pill, or capsule can contain more than 0.01 percent (e.g., more than 0.1 percent, more than one percent, more than five percent, or more than 10 percent) and/or less than 20 percent by weight (e.g., less than 10 percent, less than five percent, less than one percent, or less than 0.1 percent) of the therapeutic agent (e.g., a metal-containing material and/or a non-metal antibiotic medication). Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The tablet, pill, or capsule can then be coated with a controlled-release coating.

In some embodiments, to deliver the controlled-release composition to an area of a subject, the composition can be ingested by a subject, injected into a subject, or delivered as a suppository or enema to a subject. Examples of formulations and methods for delivery of medicaments to the intestinal tract for increased absorption are described, for example, in Davis, Drug Discovery Today, 10(4) 2005, 249-257; Fell, J. Anat. (1996) 189, 517-519; Ibekwe et al., The Drug Discovery Companies Report Spring/Summer 2004 (2004) 27-30.

In some embodiments, the formulation is a cream that has a cosmetically acceptable appearance, such as a uniform color and texture, and be absent of offensive odors. The metal-containing material can be dispersed (e.g., uniformly distributed) within a cream. The metal-containing material can be in the form of particles having a maximum dimension of at most five microns (e.g., at most four microns, at most three microns, at most two microns, at most one micron, at most 500 nm, at most 400 nm, at most 300 nm, at most 200 nm, or at most 100 nm). In some embodiments, the particles are agglomerated, and can form clusters of agglomerated particles having a maximum dimension of at most 25 microns (e.g., at most 20 microns, at most 15 microns, or at most 10 microns).

The cream can include components such as: water, cetearyl alcohol, glycerol monostearate, stearic acid, light mineral oil, isopropyl myristate, polyoxyl 40 stearate, propylparaben, methylparaben, xanthan gum (e.g., Xantural), white petrolatum, polyethylene glycol (e.g., PEG 400, PEG 300), titanium dioxide, propylene glycol, diethylene glycol monoethyl ether (Transcutol), cetyl alcohol, benzyl alcohol, hexylene glycol, EDTA, (hydroxypropyl)methylcellulose (HPMC), sodium benzoate, hydroxypropylcellulose (HPC), methyl cellulose (e.g., methyl cellulose A4M), sodium carboxymethylcellulose, sodium parabens, crosslinked polyacrylate polymer (e.g., Carbopol), and/or carrageenan.

In some embodiments, the cream includes at least 0.1 percent (e.g., at least 0.2 percent, at least 0.3 percent, at least 0.4 percent, at least 0.5 percent, at least 0.6 percent, at least 0.8 percent, at least one percent, at least 1.5 percent, at least two percent, at least three percent, or at least four percent) and/or at most five percent (at most four percent, at most three percent, at most two percent, at most 1.5 percent, at most one percent, at most 0.8 percent, at most 0.6 percent, at most 0.5 percent, at most 0.4 percent, at most 0.3 percent, or at most 0.2 percent) by weight of a silver-containing material. In some embodiments, the cream includes from 0.1 to five (e.g., from 0.1 to two, from 0.1 to one, from 0.1 to 0.5, from 0.2 to four, from 0.4 to three, from 1 to three, from two to three) percent by weight of an ebselen derivative. In some embodiments, the cream includes from 100 µg to 20000 µg (e.g., from 100 µg to 10000 µg, from 100 µg to 1000 µg, from 1000 µg to 20000, or from 1000 to 20000 µg) of the metal-containing material per gram of the cream. In some embodiments, the concentration of the metal-containing material in a cream is at most the minimum inhibitory concentration for a given bacterium species (e.g., a sporulating bacterium species).

In some embodiments, the cream includes white petrolatum as an emollient, and can moisturize an area of the skin by decreasing evaporation from the skin.

In some embodiments, the cream includes isopropyl myristate, which can be a moisturizing agent and an emollient, and can be unreactive with the metal-containing material. In some embodiments, isopropyl myristate is a vehicle for the metal-containing material and can enhance the absorption of the metal-containing material through the skin.

In some embodiments, the cream includes polyoxyl 40 stearate, a nonionic surface-active agent, and can be an emulsifying agent in a cream.

In some embodiments, the cream includes cetearyl alcohol, which can form an occlusive film and decrease the likelihood of skin moisture evaporation.

In some embodiments, the cream includes cetyl alcohol, which is an emollient, a thickening agent, and/or can lighten the color of the cream (e.g., a cream including a metal-containing material).

In some embodiments, the cream includes glycerol monostearate, which can provide moisturizing properties and/or can thicken the cream.

In some embodiments, the cream includes stearic acid, which can stabilize the cream and can help maintain the cream in a similar color and texture for a period of time (e.g., at least one month, at least two months, at least three months, at least six months, or at least a year) after cream formation. In some embodiments, stearic acid is an emollient and can provide moisturizing properties to skin.

In some embodiments, the cream includes poly(ethylene glycol). An example of a polyethylene glycol is PEG 400. PEG 400 can be compatible with a metal-containing material and enhance the texture of the cream to produce a smooth feeling during application. In some embodiments, PEG 400 can stabilize the cream. In some embodiments, PEG 400 can slow the drying process of the formulation and moisturize a skin area to which the cream has been applied.

In some embodiments, the cream includes benzyl alcohol, which is a preservative and can decrease the likelihood of microbial proliferation in the cream. In some embodiments, benzyl alcohol is absent when the cream includes a metal-containing material.

In some embodiments, the cream includes titanium dioxide, which can lighten the color of the cream, for example, to provide a more aesthetically pleasing color. In some embodiments, titanium dioxide is coated with stearic acid prior to addition to a cream. In certain embodiments, titanium dioxide is coated with stearic acid in situ during formation of the cream. In some embodiments, titanium dioxide is not coated with stearic acid prior to addition to a formulation, or during formation of the cream.

In some embodiments, the cream includes light mineral oil, which is an emollient and can moisturize the skin to which the cream is applied.

In certain embodiments, the cream can include propyl paraben or methyl paraben, preservatives that can decrease the likelihood of microbial proliferation in the cream (or the cbase cream before compounding with antibiotic).

In certain embodiments, the cream can include xanthan gum, which can thicken a formulation and help suspend the components of the cream to form a homogeneous mixture. In some embodiments, xantham gum is absent when the cream contains a metal-containing material.

In some embodiments, the cream can include water.

In some embodiments, the cream can include iron oxide, which can be added for color matching between creams having different concentrations of a metal-containing material.

In some embodiments, the material can be in the form of a nanodispersion.

The nanodispersion can be formed, for example, by dispersing a free standing powder of the material in a solution and sonicating the mixture. In some embodiments, formation of the nanodispersion further includes separating a supernatant nanodispersion from a precipitate, for example, by decantation and/or by filtration. The nanodispersion solvent can be an aqueous or an organic solvent. For example, the solvent can be an alcohol (e.g., propanol, ethanol), an organic solvent (e.g., DMSO, azone), or water. The aqueous solvent can be a solution or a buffer, such as a lactate buffer, an EDTA buffer, a citrate buffer, a glycolate buffer, or a gluconate buffer.

The nanodispersion can include a stabilizing agent, such as surfactant and/or an emulsifier. A stabilizing agent stabilizes nanodispersions by decreasing the likelihood of agglomeration of individual particles. Examples of stabilizing agents include surfactants and/or emulsifiers, such as docusate sodium, sodium lauryl sulfate, cetrimide, PEG povidone, propylene glycol, propylene glycol alginate, benzalkonium chloride, poloxamer, polyethylene alkyl ethers, sorbitan esters, xanthan gum, polysorbate (e.g., Tween 80), lecithin, pectin, polysorbate, sorbitan (e.g., SPAN) and/or polyvinyl alcohol (PVA). In some embodiments, a stabilizing agent helps suspend the metal-containing material and provides a homogeneous nanodispersion. In some embodiments, a stabilizing agent lowers the surface charge of the particles and decreases the attraction between the particles. In some embodiments, a stabilizing agent (e.g., PVA) acts as a physical barrier between particles to decrease contact between the particles. In other embodiments, stabilizing agents (e.g., lecithin) change the charge on the particles to increase particle-particle repulsion. The surface charge on the particles is assessed by measuring the zeta potential using a Zetasizer nano-ZS instrument (Malvern Instruments Ltd).

The nanodispersion can include one or more surfactants or emulsifiers.

In some embodiments, the metal-containing material can be in the form of a foam, a spray, or a drop. The foam, spray, or drop can have the same composition as a nanodispersion.

In some embodiments, the metal-containing material is in the form of a solution including dissolved metal species. The dissolved metal species can be ionic. The solution is relatively free of particulates having a size greater than one nm. The solution can be formed by dissolving a free standing powder of the material in a solvent for the powder, and filtering the mixture through a filter (e.g., a 0.1 μm filter, a 0.2 μm filter). As an example, a container (e.g., a tea bag-type container) with the free standing powder within it can be immersed in the water or solvent and the resulting solution can be filtered. As another example, a substrate (e.g., in the form of a strip or a bandage) carrying the material can be immersed in the solvent to disperse the metal-containing material. The solvent containing the substrate can be shaken in a shaking incubator (e.g., at 180 RPM and 37° C. for 30 minutes) and/or stirred, then filtered.

In some embodiments, the metal containing material can be in the form of a foam, a spray, or a drop. The foam, spray, or drop can have the same composition as a solution.

In some embodiments, the metal-containing material can be a freeze-dried powder, formed from freeze-drying a nanodispersion of the metal-containing material that further includes a bulking agent (e.g., mannitol, glycine, gelatin, dextran, glucose, sucrose, and/or lactose) and/or a cryoprotectant (e.g., glycine, glucose, fructose, sucrose, lactose). Without wishing to be bound by theory, it is believed that a bulking agent decreases the likelihood of particle agglomeration, which can occur at high particle concentrations as the solvent is removed by freeze-drying. A cryoprotectant decreases the likelihood of formation of water crystals, which can push the particles into close proximity and increase the likelihood of particle agglomeration. In some embodiments, the freeze-dried powder can be reconstituted into a suspension and/or nanodispersion, for example, by adding water or an aqueous solution and/or by ultrasonicating. In some embodiments, the freeze-dried powder can be incorporated into a pill, capsule, or tablet.

In some embodiments, the metal-containing material is in the form of a suppository.

While a controlled-release composition, a cream, a nanodispersion, a solution, a freeze-dried powder, and a suppository have been described in the foregoing, in certain embodiments, the formulation can be in the form of a lotion, a gel, a paste, or an ointment. The lotion can have a lower viscosity than a cream; the gel can be transparent, translucent, and/or opaque, the paste can have more solids than a cream; and an ointment can have low levels of water or be substantially free of water (e.g., about 80% free of water, about 90% free of water, about 95% free of water, about 98% free of water, about 99% free of water, 100% free of water).

In some embodiments, various formulations can optionally include one or more components which can be biologically active or biologically inactive. Examples of components are described above. Further examples of such optional components include base components (e.g., water and/or an oil, such as liquid paraffin, vegetable oil, peanut oil, castor oil, cocoa butter), thickening agents (aluminum stearate, hydrogenated lanolin), gelling agents, dispersing agents, suspending agents, thickening agents, coloring agents, perfumes, excipients (starch, tragacanth, cellulose derivatives, silicones, bentonites, silicic acid, talc), foaming agents (e.g., surfactants), surface active agents, preservatives (e.g., methyl paraben, propyl paraben, benzyl alcohol), and cytoconductive agents (e.g., betaglucan). In certain embodiments, a pharmaceutical carrier composition can include a constituent (e.g., DMSO) to assist in the penetration of skin. In some embodiments, a formulation can include tinting agents, emollients, skin conditioning agents, humectants, preservatives, antioxidants, perfumes, chelating agents: physically and chemically compatible with other components of the composition.

In some embodiments, depending on the condition to be treated, a solution and/or a nanodispersion containing the material can contact an area having mucous membranes such as mouth, eyes, colon, lungs, and/or other organs, in the form of a rinse, a bath, a wash, an enema, a gargle, a spray, and/or drops, with or without the use of a device. As an example, the solution and/or the nanodispersion can be injected into a subject using a small needle injector and/or a needleless injector. As an another example, the solution and/or the nanodispersion containing the material can be formed into an aerosol (e.g., an aerosol prepared by a mechanical mister, such as a spray bottle or a nebulizer), and the aerosol can be contacted with the subject using an appropriate device (e.g., a hand held inhaler, a mechanical mister, a spray bottle, a nebulizer, an oxygen tent). As a further example, a solution and/or nanodispersion containing the material can be contacted with the subject via a catheter.

In some embodiments, the metal-containing material is in the form of an aerosol or dry powder, formed from lyophilizing, freeze-drying, or drying a nanodispersion. The aerosol or dry powder can be inhaled to contact a respiratory area such as the mouth, lungs, or nasal passage for treatment of respiratory conditions. In some embodiments, the metal-containing material is sub-micron in size.

In some embodiments, the metal-containing material in the form of an article such as a controlled-release composition (e.g., a tablet, pill, capsule or bead having controlled-release properties and/or a controlled-release coating, an enteric-coated tablet, an enteric-coated capsule, an enteric-coated pill, a suspension of enteric-coated beads), a suppository, a solution, a nanodispersion, or a foam can contact the gastrointestinal system of a subject to treat, for example, inflammatory bowel disease (IBD). The article can include a sustained release formulation (e.g., a sustained release capsule) which can allow the metal-containing material to be released at a predetermined rate (e.g., a relatively constant rate). In some embodiments, an article can include a material (e.g., in the form of a coating and/or in the form of a matrix material) that allows the article to pass through certain portions of the gastrointestinal system with relatively little (e.g., no) release of the metal-containing material, but that allows a relatively large amount of the metal-containing material to be released in a desired portion of the gastrointestinal system. As an example, the article can be a controlled-release article (e.g., a tablet, pill, capsule or bead having a controlled-release coating, an enteric-coated tablet, an enteric-coated capsule, an enteric-coated pill, a suspension including an enteric-coated bead) so that the formulation passes through the stomach with little (e.g., no) metal-containing material being released, and so that the metal-containing material is relatively easily released by the article in the intestines. In some embodiments, the article can be an enema or a suppository, which can contact the gastrointestinal system (e.g., the colon) to provide a therapeutic effect.

In some embodiments, the metal-containing formulation (e.g., a cream) is an anti-microbial barrier. In some embodiments, the metal-containing formulation is anti-inflammatory and reduces inflammation in a subject, for example, by suppressing the expression of inflammatory cells. The metal-containing formulation can have enhanced emollient properties such that the formulation can soften and soothe the skin when applied locally. An emollient property is assessed by measuring the extent to which a formulation decreases water evaporation (e.g., from skin). The metal-containing formulation can be substantially free of steroids. The metal-containing formulation can be non-allergenic (e.g., non-allergenic to nuts). In some embodiments, a formulation without metal-containing material, such as a cream, has moisturizing and protecting properties, which can provide therapeutic effects when applied onto an area of a subject. The moisturizing property is measured by a transepidermal water loss (TEWL) test using healthy volunteers (International Research Services Inc (IRSI). Port Chester, N.Y.). In some embodiments, water loss is measured using a Vapometer (Delfin Technologies Ltd., Finland).

In some embodiments, the metal containing formulation has good spreadability, such that the formulation can be spread into a thin layer when topically applied before drying. The spreadability can depend on the viscosity, the melting temperature, the evaporation rate, and/or the solid content of the formulation. For example, in some embodiments, a low viscosity formulation (e.g., viscosity of less than 45,000 cPs) can have a large spreadability and a watery feeling when rubbed into an area of the skin, and a high viscosity (e.g., greater than 2,000,000 cPs) can limit the spreadability of the formulation.

In some embodiments, a metal-containing formulation including metal-containing particles of small particle size (e.g., about 400 nm or less, about 300 nm or less, about 200 nm or less, about 150 nm or less, about 100 nm or less, about 50 nm or less, or about 25 nm or less; and/or about 10 nm or more, about 25 nm or more, about 50 nm or more, about 100 nm or more, about 150 nm or more, about 200 nm or more, or about 300 nm or more) can be more therapeutically effective (e.g., 2× more effective, 5× more effective, 10× more effective, 20× more effective, 50× more effective, 100× more effective) than a metal-containing formulation that does not include metal-containing particles of small particle size, such that a smaller quantity of metal-containing material (e.g., 1/100 of a quantity, 1/50 of a quantity, 1/20 of a quantity, 1/10 of a quantity, 1/5 of a quantity, 1/2 of a quantity) is needed to achieve the same therapeutic effect when the formulation is administered to a subject, for example, to an open wound, past the skin barrier, and/or to a mucosal or serosal area. A decreased quantity of a metal-containing material in a formulation can have decreased toxicological effect on a subject, and can facilitate the administration of a formulation.

In some embodiments, when applied to an area of a subject, the formulation can release a steady amount of a therapeutic agent (e.g., a metal-containing material and/or a non-metal antibiotic medication) over a period of time (e.g., at least 30 minutes, at least one hour, at least two hours, at least three hours, at least six hours, at least 12 hours, or at least 24 hours; and/or at most 48 hours, at most 24 hours, at most 12 hours, at most six hours, at most three hours, at most two hours, or at most one hour). In some embodiments, the period of time is from 30 minutes to 48 hours (e.g., from 30 minutes to 24 hours, from one hour to 24 hours, from six hours to 24 hours). A steady amount refers to an amount that varies by less than 90% (less than 80%, less than 70%, less than 60%) of the initial amount over the period of time.

Examples of silver-containing materials include silver oxide, colloidal silver, silver nitrate and silver sulfadiazine, silver carbonate, silver acetate, silver lactate, silver citrate, silver hydroxide, silver succinate, silver chlorate, silver stearate, silver sorbate, silver oleate, silver gluconate, silver glycolate, silver adipate, silver myristate, silver benzoate, silver methanesulfonate, silver trifluoracetate, silver trifluoromethanesulfonate, silver behenate, silver phthalate, silver oxalate, silver sulfonate, and alkali silver thiosulphate (e.g., sodium silver thiosulphate, potassium silver thiosulphate).

In addition to one or more metal elements, a metal-containing material can contain, for example, oxygen, nitrogen, carbon, boron, sulfur, phosphorus, silicon, a halogen (e.g., fluorine, chlorine, bromine, iodine) and/or hydrogen. Examples of such metal-containing materials include metal oxides, metal hydroxides, metal nitrides, metal carbides, metal phosphides, metal silicates, metal borides, metal sulfides, metal halides (e.g., metal fluorides, metal chlorides, metal bromides, metal iodides), metal myristates, metal sorbates, metal stearates, metal oleates, metal gluconates, metal glycolates, metal adipates, metal silicates, metal phosphides, metal hydrides, metal nitrates, metal carbonates, metal sulfadiazines, metal hydrides, metal acetates, metal lactates, metal citrates, metal benzoate, metal methanesulfonate, metal trifluoracetate, metal trifluoromethanesulfonate, metal behenate, metal phthalate, metal oxalate, metal sulfonate, alkali metal thiosulphates (e.g., sodium metal thiosulphate, potassium metal thiosulphate). In certain embodiments, a metal-containing material contains at least about one atomic percent (e.g., at least about three atomic percent, at least about five atomic percent, at least about 10 atomic percent, at least about 20 atomic percent, at least about 30 atomic percent, at least about 40 atomic percent, or at least about 50 atomic percent) and/or at most about 90 atomic percent (e.g., at most about 80 atomic percent, at most about 70 atomic percent, at most about 60 atomic percent, at most about 50 atomic percent, at most about 40 atomic percent, at most about 30 atomic percent, at most about 20 atomic percent, at most about 15 atomic percent, at most about 12 atomic percent, or at most about 10 atomic percent) of nonmetallic elements. For example, in some embodiments, a silver-containing material can contain oxygen in an amount from about five atomic percent to about 20 atomic percent (e.g., from about five atomic percent to about 15 atomic percent, from about eight atomic percent to about 12 atomic percent).

Examples of antimicrobial metal-containing materials (which may or may not also be an atomically disordered crystalline material or a nanocrystalline material) include antimicrobial silver-containing materials (e.g., antimicrobial silver, silver alloys, silver oxides, silver carbides, silver nitrides, silver borides, silver sulfides, silver myristates, silver stearates, silver oleates, silver gluconates, silver glycolates, silver adipates, silver silicates, silver phosphides, silver halides, silver hydrides, silver nitrates, silver carbonates, silver sulfadiazines, silver acetates, silver lactates, silver citrates, silver benzoate, silver methanesulfonate, silver trifluoracetate, silver trifluoromethanesulfonate, silver behenate, silver phthalate, silver oxalate, silver sulfonate, alkali silver thiosulphates (e.g., sodium silver thiosulphate, potassium silver thiosulphate)), antimicrobial gold-containing materials (e.g., antimicrobial gold, gold alloys, gold oxides, gold carbides, gold nitrides, gold borides, gold sulfides, gold myristates, gold stearates, gold oleates, gold gluconates, gold glycolates, gold adipates, gold silicates, gold phosphides, gold halides, gold hydrides, gold nitrates, gold carbonates, gold sulfadiazines, gold acetates, gold lactates, gold citrates, gold benzoate, gold methanesulfonate, gold trifluoracetate, gold trifluoromethanesulfonate, gold behenate, gold phthalate, gold oxalate, gold sulfonate, alkali gold thiosulphates (e.g., sodium gold thiosulphate, potassium gold thiosulphate)), antimicrobial platinum-containing materials (e.g., antimicrobial platinum, platinum alloys, platinum oxides, platinum carbides, platinum nitrides, platinum borides, platinum sulfides, platinum myristates, platinum stearates, platinum oleates, platinum gluconates, platinum glycolates, platinum adipates, platinum silicates, platinum phosphides, platinum halides, platinum hydrides, platinum nitrates, platinum carbonates, platinum sulfadiazines, platinum acetates, platinum lactates, platinum citrates, platinum benzoate, platinum methanesulfonate, platinum trifluoracetate, platinum trifluoromethanesulfonate, platinum behenate, platinum phthalate, platinum oxalate, platinum sulfonate, alkali platinum thiosulphates (e.g., sodium platinum thiosulphate, potassium platinum thiosulphate)), antimicrobial palladium-containing materials (e.g., antimicrobial palladium, palladium alloys, palladium oxides, palladium carbides, palladium nitrides, palladium borides, palladium sulfides, palladium myristates, palladium stearates, palladium oleates, palladium gluconates, palladium glycolates, palladium adipates, palladium silicates, palladium phosphides, palladium halides, palladium hydrides, palladium nitrates, palladium carbonates, palladium sulfadiazines, palladium acetates, palladium lactates, palladium citrates, palladium benzoate, palladium methanesulfonate, palladium trifluoracetate, palladium trifluoromethanesulfonate, palladium behenate, palladium phthalate, palladium oxalate, palladium sulfonate, and/or alkali palladium thiosulphates (e.g., sodium palladium thiosulphate, potassium palladium thiosulphate)), antimicrobial zinc-containing materials (e.g., antimicrobial zinc, zinc alloys, zinc oxides, zinc carbides, zinc nitrides, zinc borides, zinc sulfides, zinc myristates, zinc stearates, zinc oleates, zinc gluconates, zinc glycolates, zinc adipates, zinc silicates, zinc phosphides, zinc halides, zinc hydrides, zinc nitrates, zinc carbonates, zinc sulfides, zinc sulfadiazines, zinc acetates, zinc lactates, zinc citrates, zinc benzoate, zinc methanesulfonate, zinc trifluoracetate, zinc trifluoromethanesulfonate, zinc behenate, zinc phthalate, zinc oxalate, zinc sulfonate), antimicrobial copper-containing materials (e.g., antimicrobial copper, copper alloys, copper oxides, copper carbides, copper nitrides, copper borides, copper sulfides, copper myristates, copper stearates, copper oleates, copper gluconates, copper glycolates, copper adipates, copper silicates, copper phosphides, copper halides, copper hydrides, copper nitrates, copper carbonates, copper sulfides, copper sulfadiazines, copper acetates, copper lactates, copper citrates, copper benzoate, copper methanesulfonate, copper trifluoracetate, copper trifluoromethanesulfonate, copper behenate, copper phthalate, copper oxalate, copper sulfonate, alkali copper thiosulphates (e.g., sodium copper thiosulphate, potassium copper thiosulphate)).

While the preceding paragraph lists certain metal-containing materials that are anti-microbial, similar metal-containing materials (oxides, carbides, nitrides, borides, sulfides, myristates, stearates, oleates, gluconates, glycolates, adipates, silicates, phosphides, halides, hydrides, nitrates, hydroxides, carbonates, sulfides, sulfadiazines, acetates, lactates, citrates, benzoates, methanesulfonates, trifluoracetates, trifluoromethanesulfonates, behenates, phthalates, oxalates, sulfonates, and/or alkali metal thiosulphates of silver, gold, palladium, and/or platinum can be anti-biofilm materials, antibacterial (e.g., antibacterial, anti-bacterial spore) materials, anti-inflammatory materials, antifungal materials, antiviral materials, anti-autoimmune materials, anti-cancer materials, and/or MMP modulating materials.

The metal-containing material can be used to treat, for example a human or an animal (e.g., a dog, a cat, a horse, a bird, a reptile, an amphibian, a fish, a turtle, a guinea pig, a hamster, a rodent, a cow, a pig, a goat, a primate, a monkey, a chicken, a turkey, a buffalo, an ostrich, a sheep, a llama).

Examples of commercially available metal-containing materials include the Acticoat™ family of dressings (Smith & Nephew, Hull, UK), which are formed of antimicrobial, anti-inflammatory atomically disordered, nanocrystalline silver-containing material coated on one or more substrates. Such dressings include the Acticoat™ dressings, the Acticoat7™ dressings, the Acticoat™ moisture coating dressings, and the Acticoat™ absorbent dressings.

A coating of a metal-containing material (e.g., an antimicrobial, atomically disordered, nanocrystalline silver-containing material) can be formed on a substrate using a desired technique. In certain embodiments, the coating is formed by depositing the material on the substrate surface using chemical vapor deposition, physical vapor deposition, and/or liquid phase deposition. Exemplary deposition methods include vacuum evaporation deposition, arc evaporation deposition, reactive sputtering deposition, sputter deposition, magnetron sputter deposition and ion plating.

The substrate/coating article can be used in a variety of articles. For example, the article can be in the shape of a medical device. Exemplary medical devices include wound closure devices (e.g., sutures, staples, adhesives), tissue repair devices (e.g., meshes, such as meshes for hernia repair), prosthetic devices (e.g., internal bone fixation devices, physical barriers for guided bone regeneration, stents, valves, electrodes), tissue engineering devices (e.g., for use with a blood vessel, skin, a bone, cartilage, a liver), controlled drug delivery systems (e.g., microcapsules, ion-exchange resins) and wound coverings and/or fillers (e.g., alginate dressings, chitosan powders). In some embodiments, the article is a transcutaneous medical device (e.g., a catheter, a pin, an implant), which can include the substrate/coating supported on, for example, a solid material (e.g., a metal, an alloy, latex, nylon, silicone, polyester and/or polyurethane). In some embodiments, the article is in the form of a patch (e.g., a patch having an adhesive layer for adhering to the skin, such as a transdermal patch).

The metal-containing material can be in the form of a powder impregnated material. Such powder impregnated materials can, for example, be in the form of a hydrocolloid having the free standing powder blended therein. A powder impregnated material can be, for example, in the form of a dressing, such as a hydrocolloid dressing.

DETAILED DESCRIPTION OF THE PREFERRED EMBODIMENTS

Figure 1A:
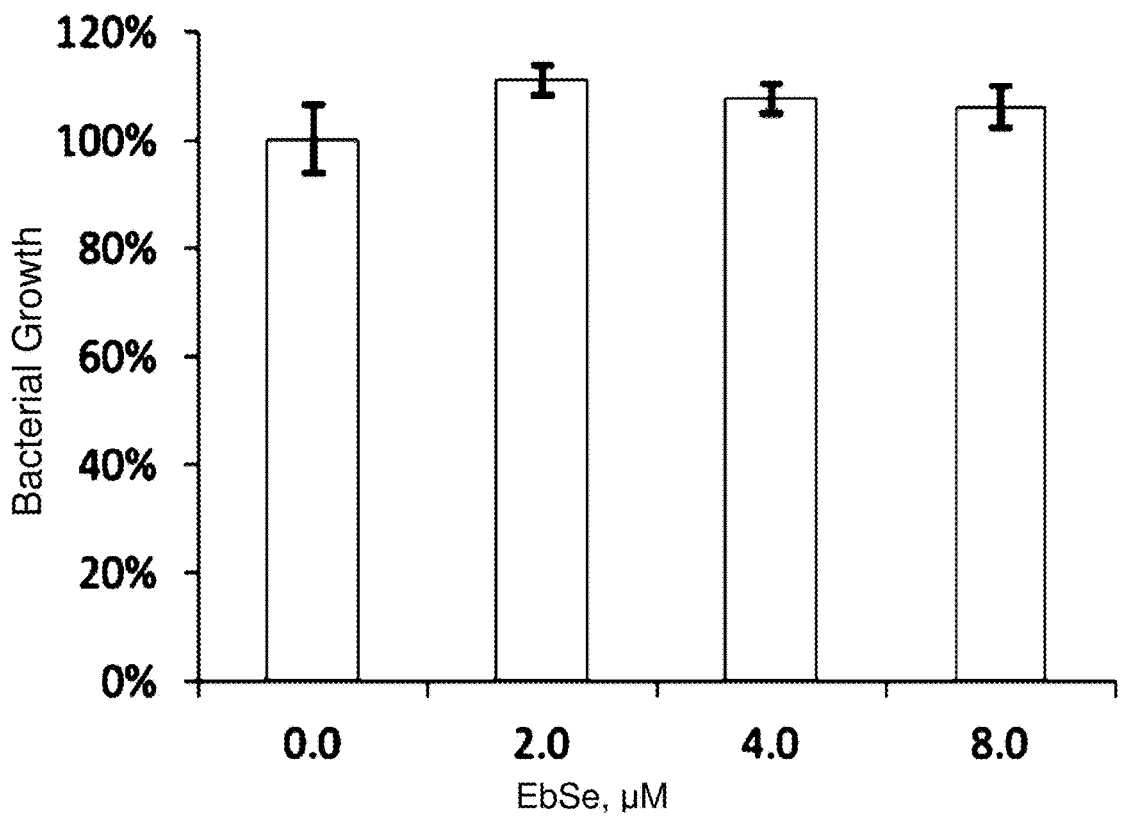
FIGS. 1A-1D show the synergistic effects of the combination of ebselen and silver against bacteria.

Material and Methods
Reagents and Bacterial Strains.

Silver nitrate, NADPH, 5,5'-dithiobis-2-nitrobenzoic acid (DTNB), Dimethyl sulfoxide (DMSO), glutathione reductase were obtained from Sigma-Aldrich (St. Louis, Mo., USA). Ebselen (EbSe) were the products of Daiichi Pharmaceutical Co., Ltd (Tokyo, Japan). Wild type *E. coli* Trx1, were from IMCO corporation, Stockholm, Sweden (www.imcocorp.se). The *E. coli* DHB4 strains wild type, mutants gshA$^-$, oxyR$^-$, trxA$^-$trxB$^-$trxC$^-$ were described in a previous study (9).

Growth Inhibition of *E. coli* Strains by Ebselen and Silver Nitrate.

*E. coli* strains (wild type, mutants gshA$^-$, trxA$^-$trxB$^-$trxC$^-$) were cultured overnight in LB medium at 37° C. with shaking. Then the overnight cultures were diluted 1000 times and grown in LB medium containing different concentration of ebselen and silver nitrate in 96 well plates. Bacterial growth was determined as A$_{600}$ after 16 hour or 42 h culture at 37° C. The culture without treatment was used as a control.

Preparation of Bacterial Cell Lysates

The *E. coli* strains were grown till the absorbance around 0.3 in LB medium, the bacterial cells were treated with different combinations of silver nitrate and ebselen for 1 h, and the absorbance at 600 nm was measured to detect the growth of the bacteria. To analyze the TrxR activity and GSH amount in the bacteria, the cells were harvested by centrifugation and washed with PBS, then the cells were resuspended in TE buffer (50 mM Tris-HCl, pH 7.5, 1 mM EDTA) containing protease inhibitor cocktail and lysed by sonication. The cell lysates were obtained by centrifugation at 13,000 rpm for 30 min and the protein concentration were measured by Lowry protein assay (Bio-Rad DC).

Measurement of TrxR Activity and GSH Amount in Cell Lysates

*E. coli* TrxR activity was measured by insulin coupled reduction endpoint assay. The experiment was performed with a 96 well plate in the solution containing 50 mM Tris-HCl, pH 7.5, 200 µM NADPH, 1 mM EDTA, 100 µM insulin, in the presence of 5 µM *E. coli* Trx. The reaction continued for 30 min. Then, 200 µM of 6 M guanidinium hydrochloride, 1 mM DTNB was added into the 50 µl of reaction solution to stop the reaction and convert DTNB into TNB$^{2-}$, which was quantified by measuring the absorbance at 412 nm to represent TrxR activity. A sample without *E. coli* Trx was used as the background control.

*E. coli* TrxR activity in cell lysates was also determined by a DTNB reduction activity assay. The reaction solution was same as above described except that using 1 mM DTNB instead of 100 µM insulin. The absorbance at 412 nm was measured for 5 min with a VERSA microplate reader and the slope of initial 2 min was used to represent DTNB reduction activity.

To measure GSH levels, 10 µg of the cell lysates was added in the solution containing 50 nM GR, 50 mM Tris-HCl, pH 7.5, 200 µM NADPH, 1 mM EDTA, 1 mM DTNB. The absorbance at 412 nm was measured for 5 min.

Toxicity of Ebselen on Mammalian Cells.

RAW 264.7, J774, HEK 293T, Hela cells were cultured in DMEM medium (GIBCO) supplemented with 10% FCS, 100 units/ml penicillin, and 100 µg/ml streptomycin at 37° C. in a 5% CO$_2$ incubator. The cells were seeded in 96 micro-well plates and grown till 70-80% confluency. The cells were treated with different combination of ebselen and silver for 24 h. The cell toxicity was detected by MTT assay (15). Data are means±SD of three independent experiments.

Results

Effects of the Combination of EbSe and Silver on the Growth of Bacteria

Since both ebselen and silver show antibacterial activity, interacting with thiol dependent redox systems, the effects of the combination of the two compounds on the growth of bacteria was investigated. For both of gram-negative bacteria *E. coli* and gram-positive bacteria *Bacillus subtilis*, low amounts of ebselen dramatically enhanced the inhibitory efficiency of bacterial growth by silver.

Figure 1B:
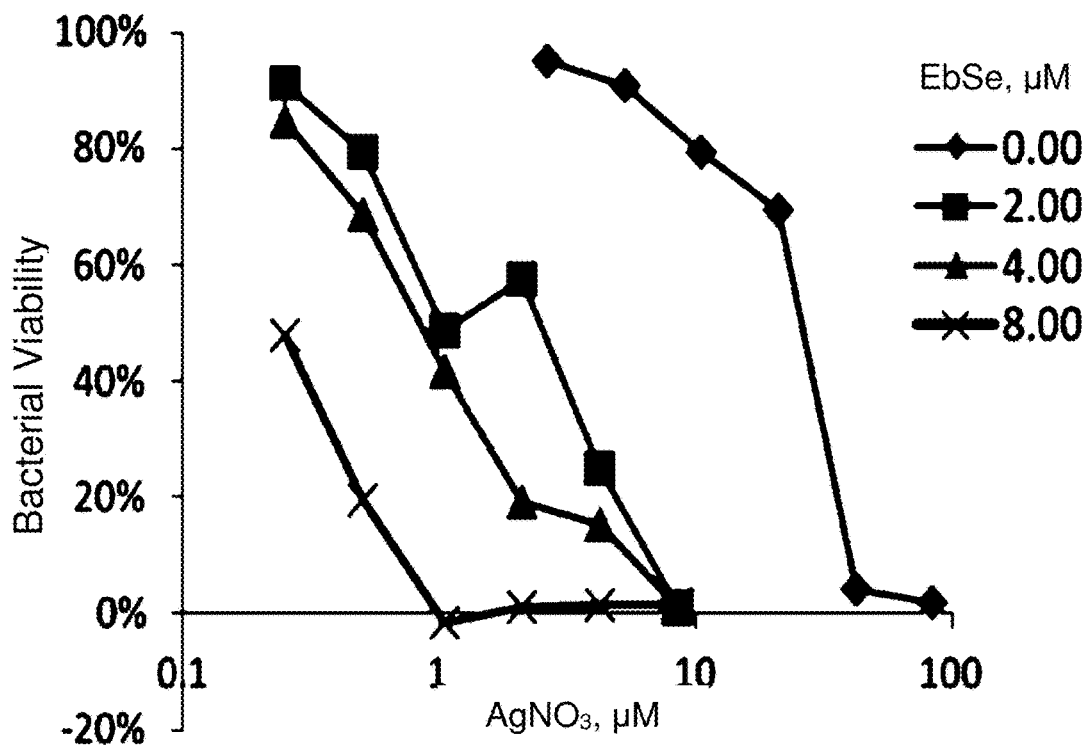

FIGS. 1A-1D show the synergistic effects of the combination of ebselen and silver against bacteria. The overnight bacterial cultures were diluted 1000 times and grown in LB medium containing 2, 4, 8 µM ebselen and the indicated concentration of silver nitrate placed in 96 well plates. Bacterial growth was determined as A$_{600}$ after 16 h at 37° C. The culture without treatment was used as a control and showed an A$_{600}$ around 0.40 which is regarded as 100 percent. FIG. 1A shows the effects of EbSe alone on the growth of *E. coli*. FIG. 1B shows the effects of combination of EbSe and silver on the inhibition of growth of *E. coli*.

Figure 1C:
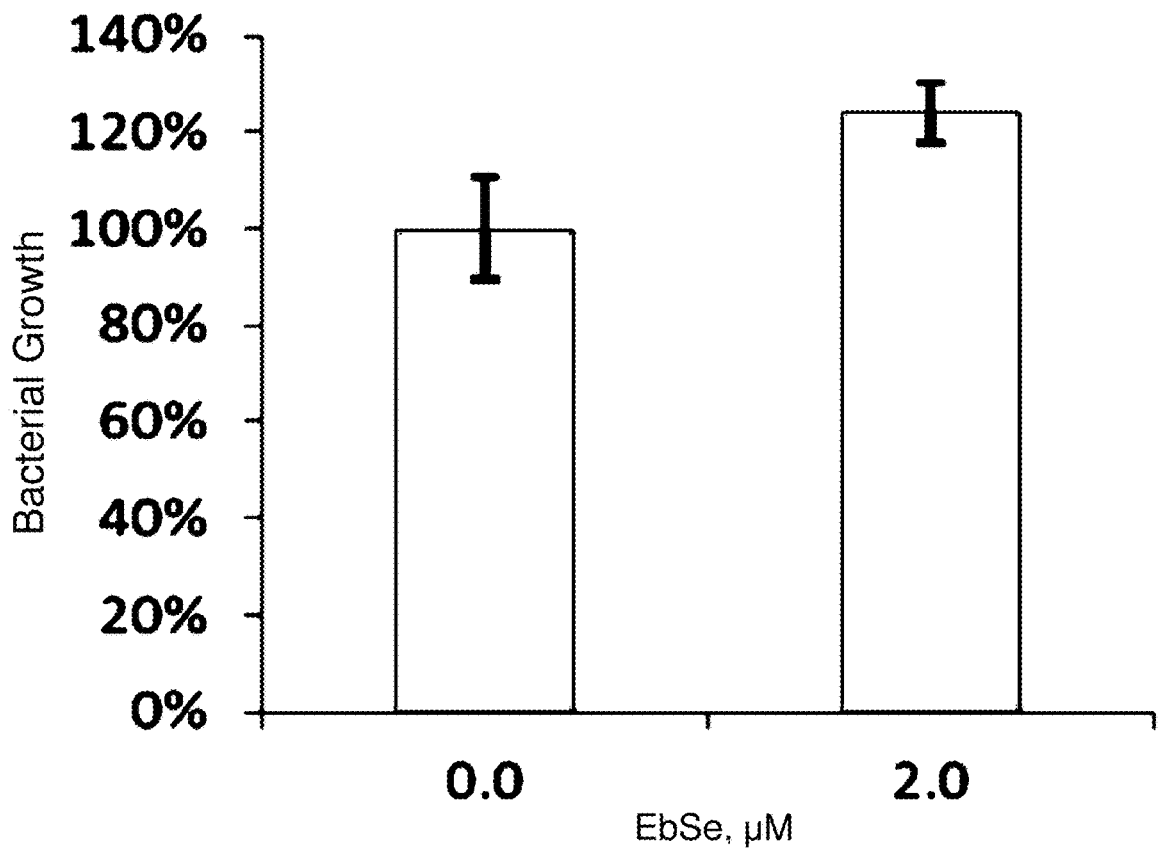
Figure 1D:
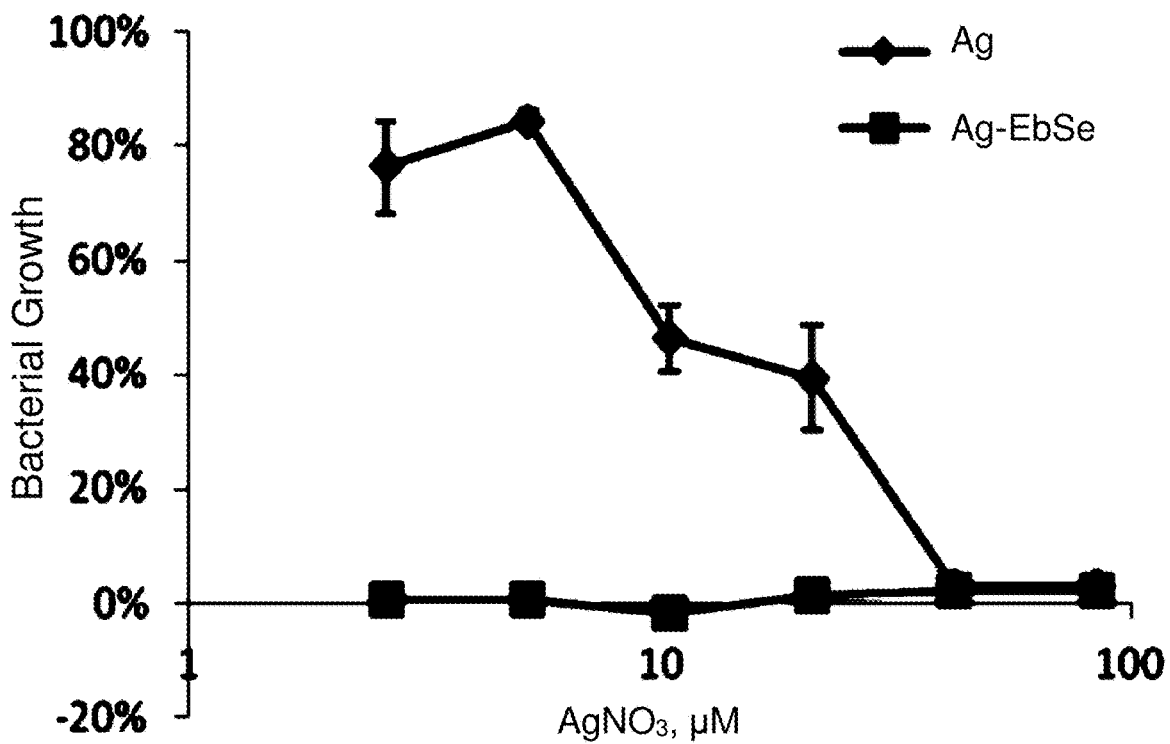

FIG. 1C shows the effects of 2 µM EbSe on the growth of *Bacillus subtilis*. FIG. 1D shows the effects of combination of EbSe and silver on the inhibition of growth of *B. subtilis*.

In LB medium, ebselen at 2, 4, 8 µM did not show the inhibition effects on bacterial growth (FIG. 1A). Interestingly, silver alone inhibited the growth of *E. coli* with MIC about 42 µM after the treatment for 16 h; in the presence of 2 µM ebselen, the MIC for silver was 8.4 µM; in the presence of 8 µM ebselen, 1 µM silver inhibited *E. coli* growth (FIG. 1B).

*B. subtilis* is a glutathione negative bacteria and was shown to be more susceptible to ebselen compared to *E. coli* (9 and data not shown). Ebselen at 2 µM did not inhibit the growth of *B. subtilis* (FIG. 1C), but strongly helped the antibacterial activity of silver (FIG. 1D).

Figure 2A:
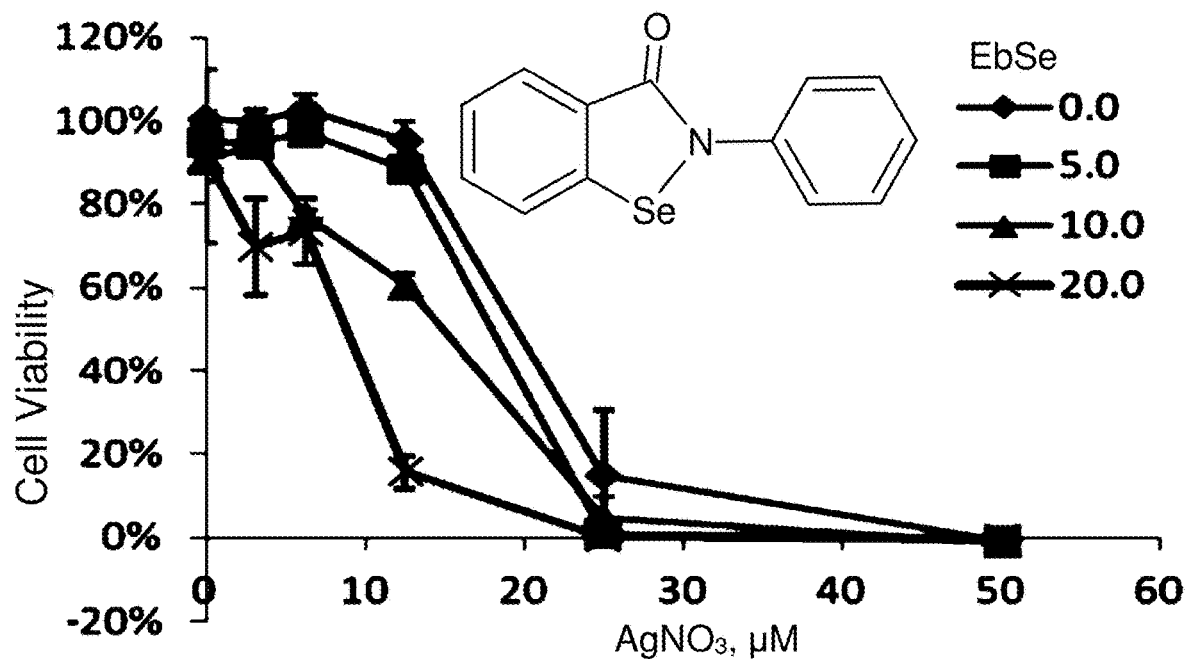
FIGS. 2A-2D show toxicity of the combination of EbSe analogues and silver toward Hela cells and *E. coli*.
Figure 2B:
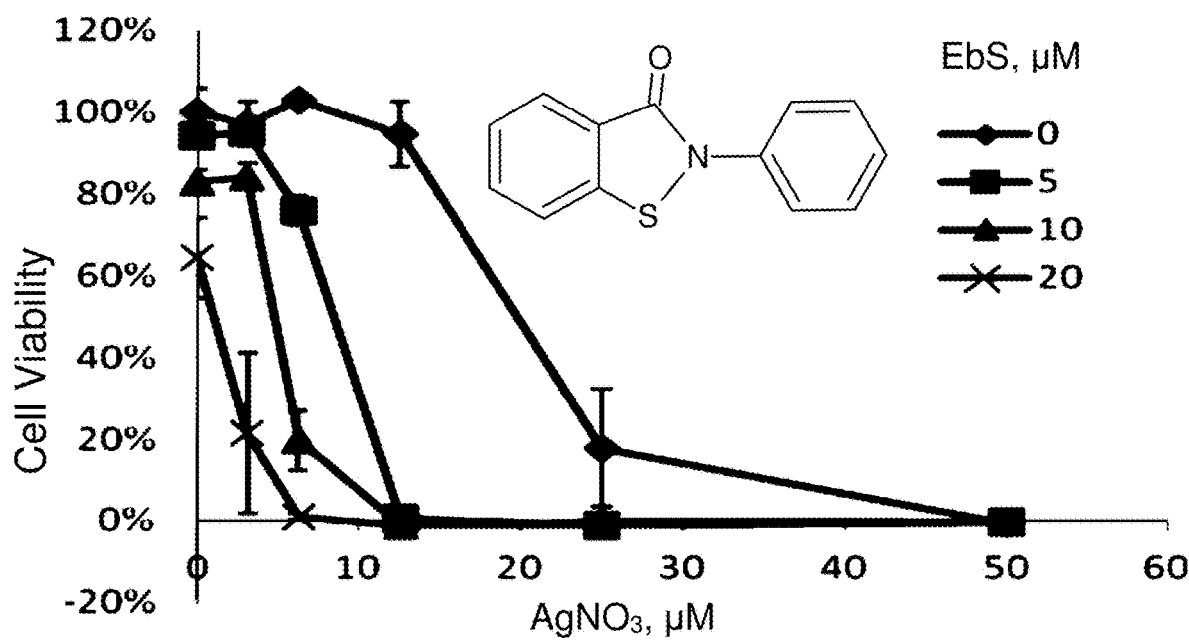
Figure 2C:
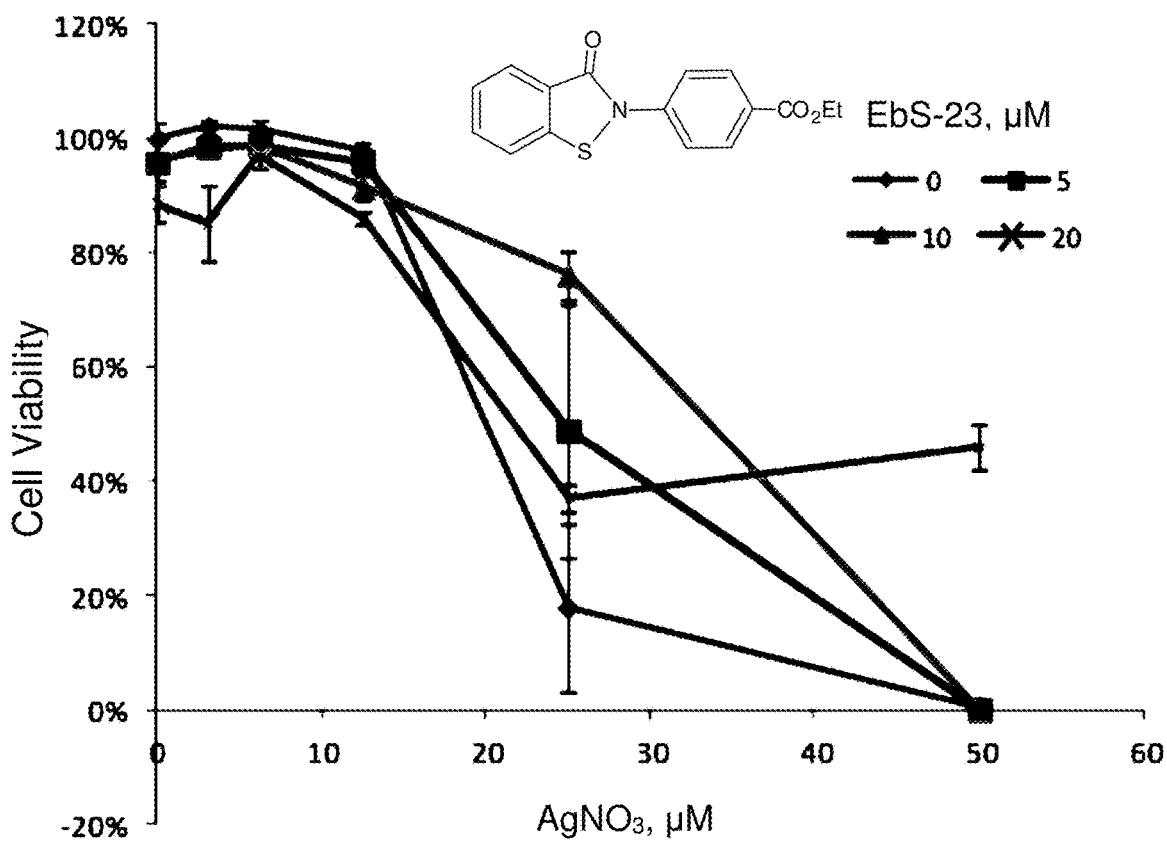
Figure 2D:
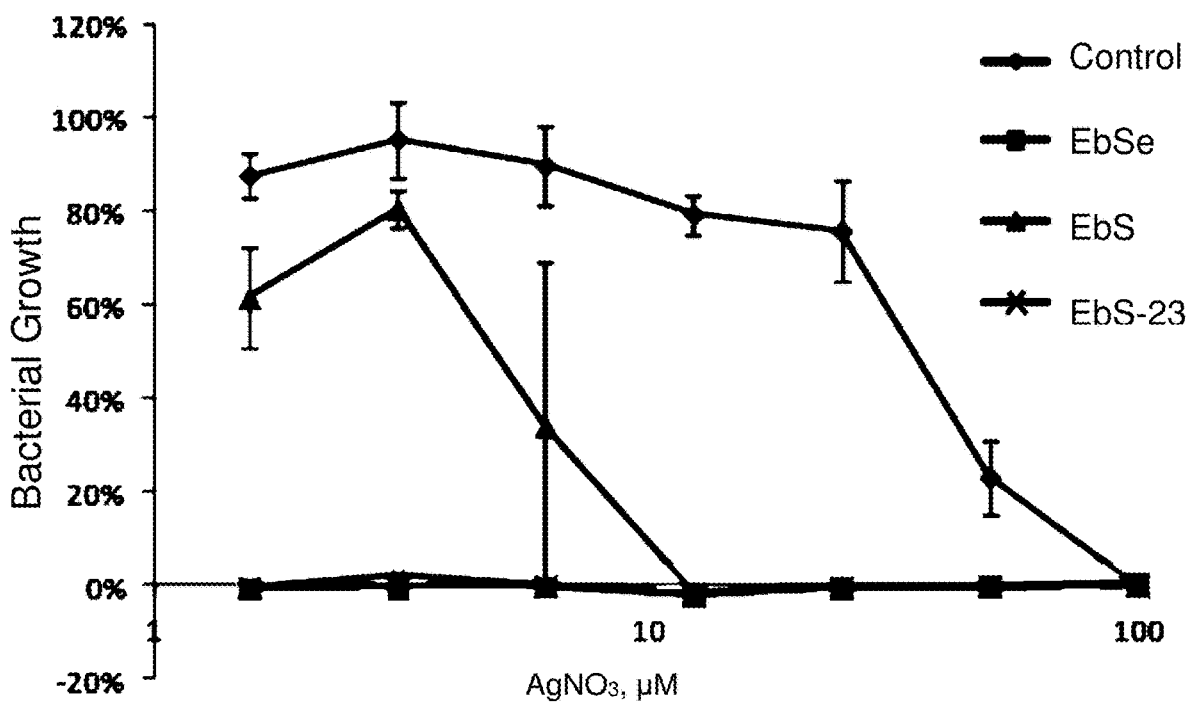

Toxicity of the Combination of EbSe Analogues and Silver Toward Mammalian and Bacterial Cells To check whether there are synergistic toxic effects on mammalian cells, the toxicity of combination of ebselen and silver towards HeLa cells was studied. FIGS. 2A-2D show toxicity of the combination of EbSe analogues and silver toward HeLa cells and *E. coli*. Nearly confluent HeLa cells were treated with combination of indicating concentration of ebselen and its analogues and silver for 24 h. then the cell toxicity was detected by MTT assay. FIG. 2A shows EbSe, FIG. 2B shows Ebsulfur, FIG. 2C shows ebsulfur-23, the sulphur analog of EbSe-10. FIG. 2D shows a comparison of the combination of EbSe analogues and silver toward *E. coli*. The overnight bacterial cultures were diluted 1000 times and grown in LB medium containing 4 µM ebselen and its analogues and the indicating concentration of silver nitrate in 96 well plates. Bacterial growth was determined as $A_{600}$ after 24 h at 37° C. The culture without treatment was used as a control.

At the concentration 5 µM, ebselen did not show synergistic of toxicity towards HeLa cells, and only at the high concentration (20 µM), ebselen enhanced the toxicity of silver at the high concentration (FIG. 2A). The other mammalian cell lines displayed similar properties. The ebselen sulfur analogue, ebsulfur, showed stronger synergistic toxic effects towards mammalian cells and less enhancement for the toxicity of silver toward bacteria (FIGS. 2B and D). Intriguingly, one ebsulfur derivative EbS23, which has been shown to possess an anti-parasitic effect in a previous study (16), had a protection role for mammalian cells (FIG. 2C), but also possessed strong enhancement effects for silver towards bacteria (FIG. 2D).

Role of Thioredoxin and Glutathione System in the Synergistic Antibacterial Effects of the Combination of Silver and Ebselen Since Trx and glutathione system may be the major interacting thiol system for ebselen, the role of the bacterial Trx and GSH system in the defense against combination treatment by silver and ebselen was investigated. Compared to wild type *E. coli*, both mutant gshA⁻ lacking the synthesis of glutathione and mutant trxA⁻trxB⁻trxC⁻ lacking the whole thioredoxin system did not exhibit a great difference for the sensitivity to silver alone.

Figure 3:
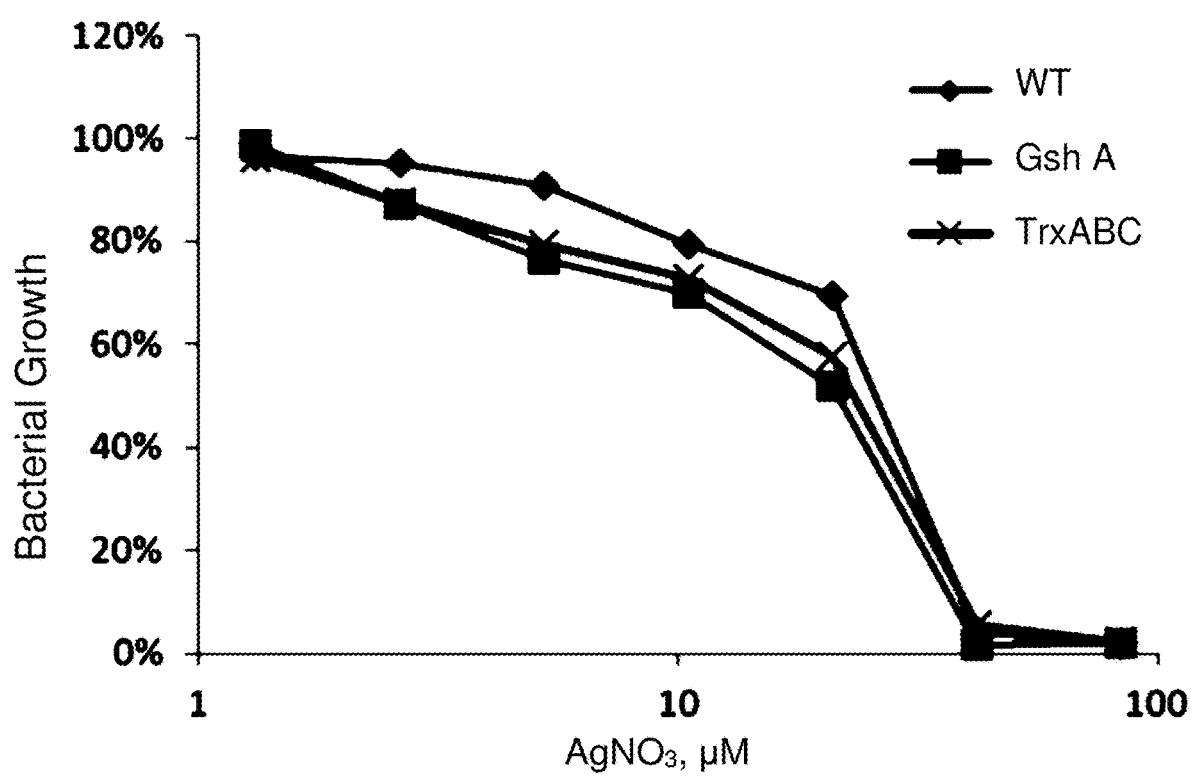
FIG. 3 shows growth inhibition of *E. coli* mutants gshA$^-$ and trxA$^-$ trxB$^-$ trxC$^-$ by AgNO$_3$.

FIG. 3 shows growth inhibition of *E. coli* mutants gshA⁻ and trxA⁻ trxB⁺ trxC⁻ by AgNO₃. The overnight *E. coli* strains (wild type, mutants gshA⁻, trxA⁻trxB⁻ trxC⁻) were diluted 1000 times and grown in LB medium containing different concentration of silver nitrate in 96 well plates. Bacterial growth was determined as $A_{600}$ after 42 h culture at 37° C. The culture without treatment was used as a control.

Figure 4A:
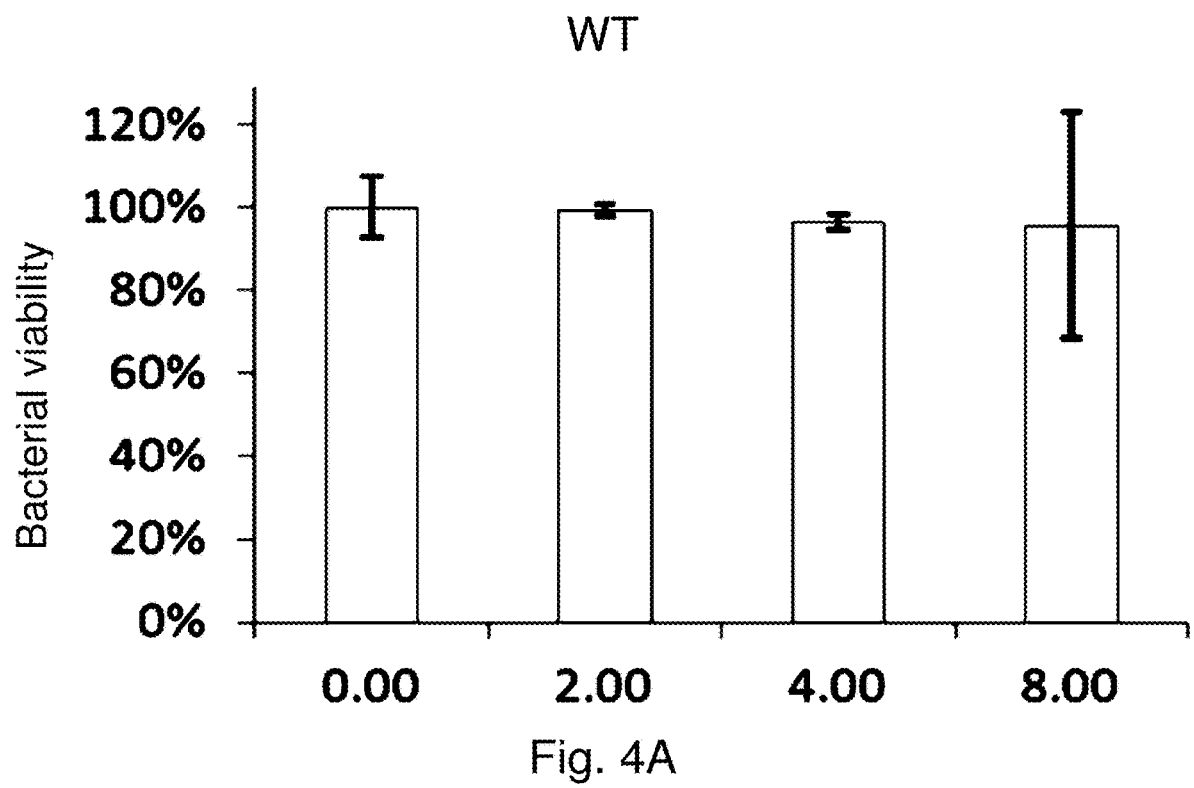
FIGS. 4A-4F demonstrate the role of bacterial Trx and GSH in the defense against the combination treatment of AgNO$_3$ and ebselen.
Figure 4B:
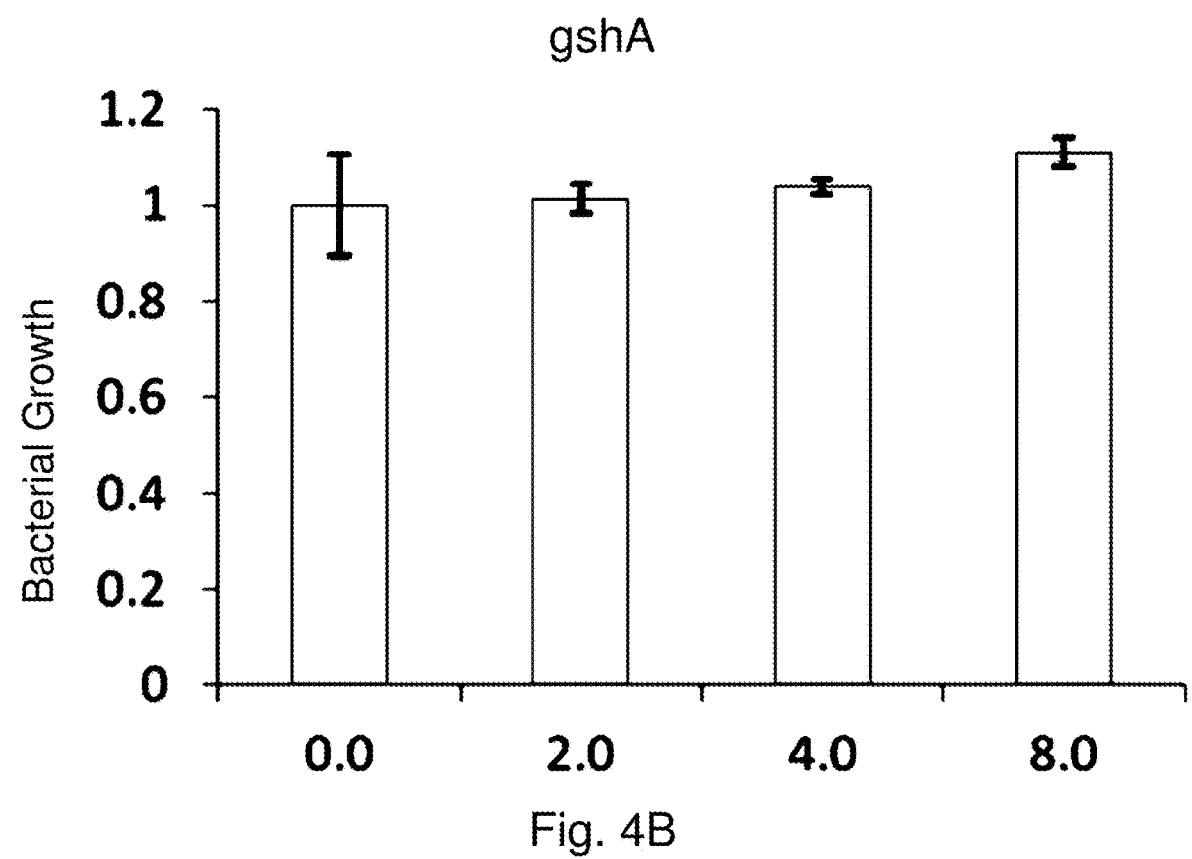
Figure 4C:
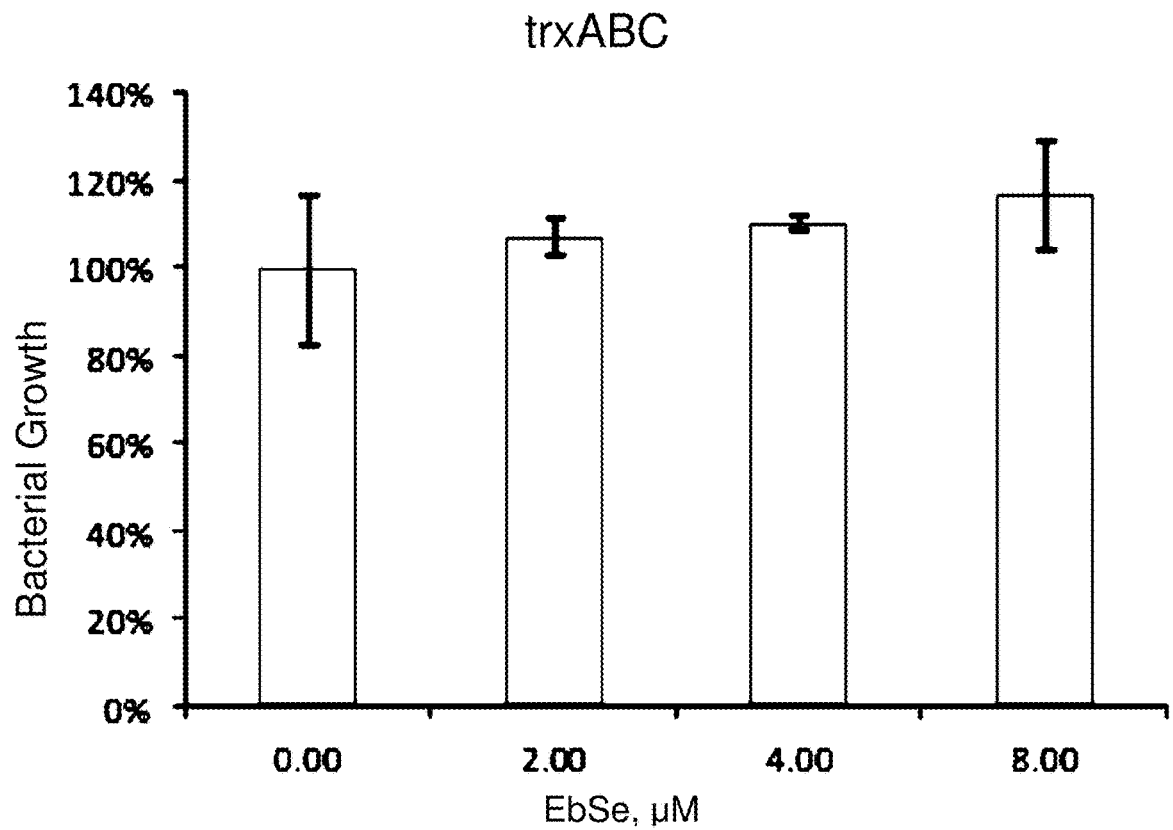
Figure 4D:
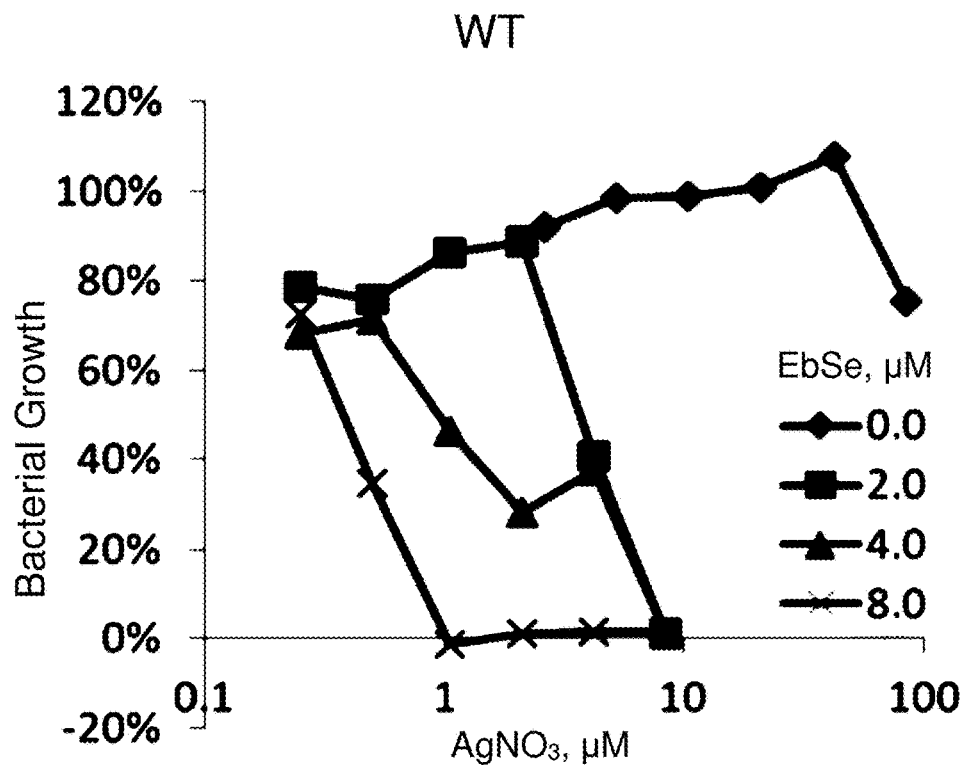
Figure 4E:
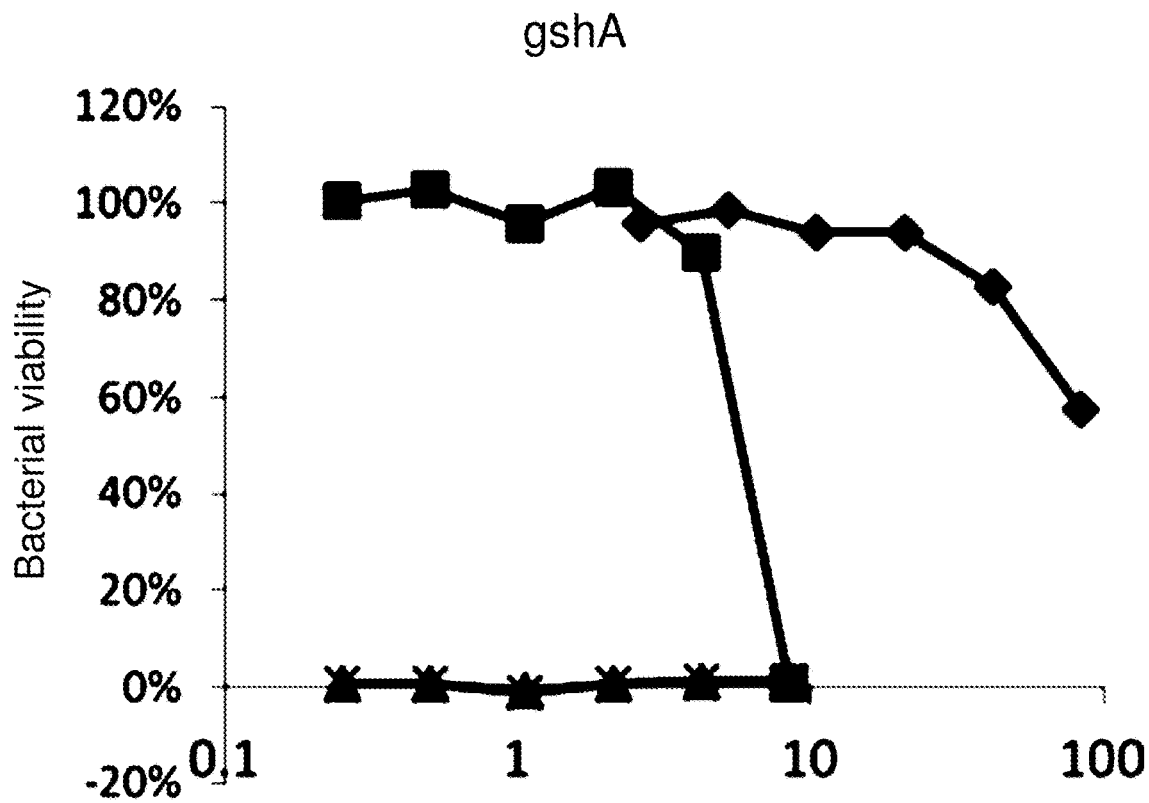
Figure 4F:
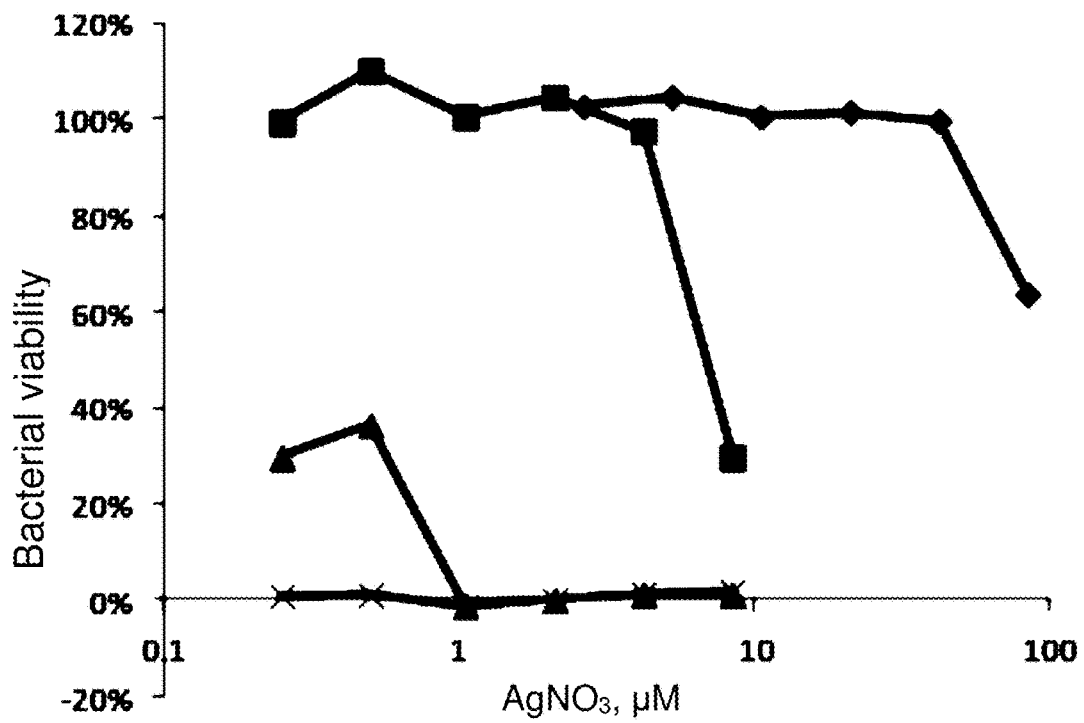

FIGS. 4A-4F demonstrate the role of bacterial Trx and GSH in the defense against the combination treatment of AgNO₃ and ebselen. The overnight *E. coli* strains (wild type, mutants gshA⁻, trxA⁻ trxfB⁻ trxC⁻) were diluted 1000 times and grown in LB medium containing different concentration of silver nitrate and ebselen in 96 well plates. Bacterial growth was determined as $A_{600}$ after 42 h culture at 37° C. The culture without treatment was used as a control. FIGS. 4A, 4C, and 4E show the effects of ebselen on the growth of *E. coli* strains (wt, gshA⁻, trxA⁻ trxB⁻ trxC⁻). FIGS. 4B, 4D, and 4F show growth inhibition of *E. coli* strains (wt, gshA⁻, trxA⁻, trxB⁻ trxC⁻) by the combination treatment of silver and ebselen.

Figure 5A:
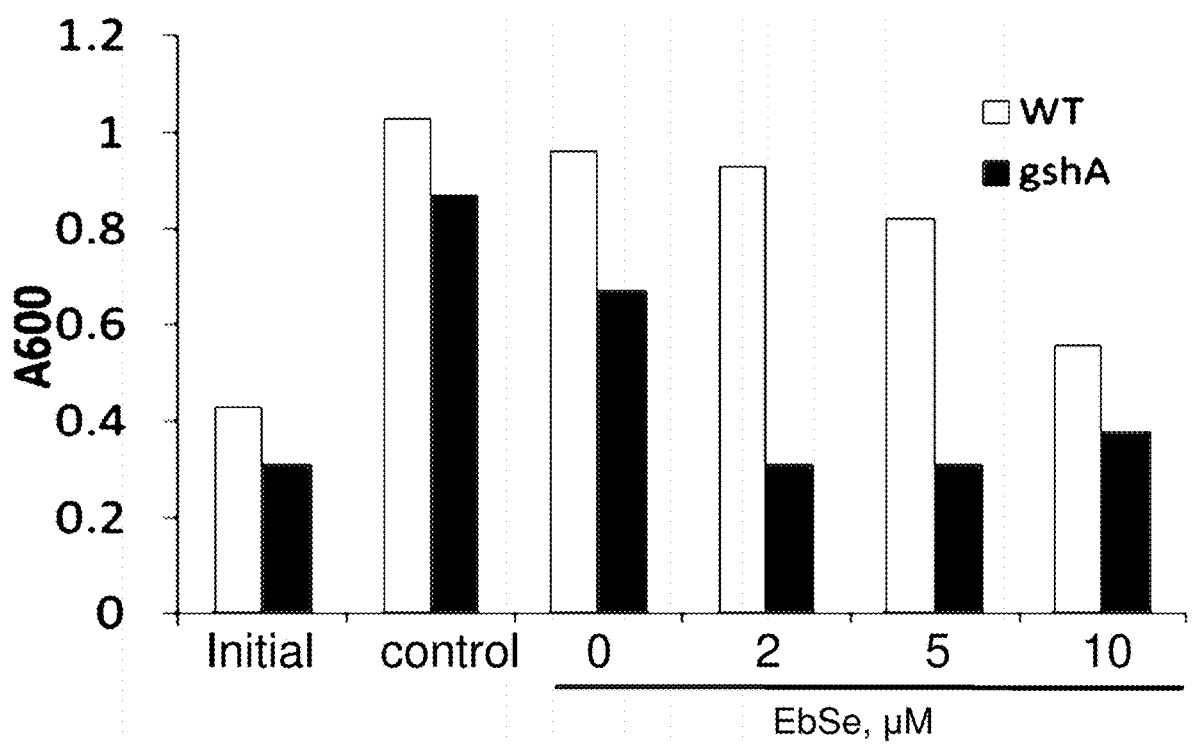
FIGS. 5A-5C show the effects of combination treatment of silver and ebselen on the bacterial Trx and GSH systems.
Figure 5B:
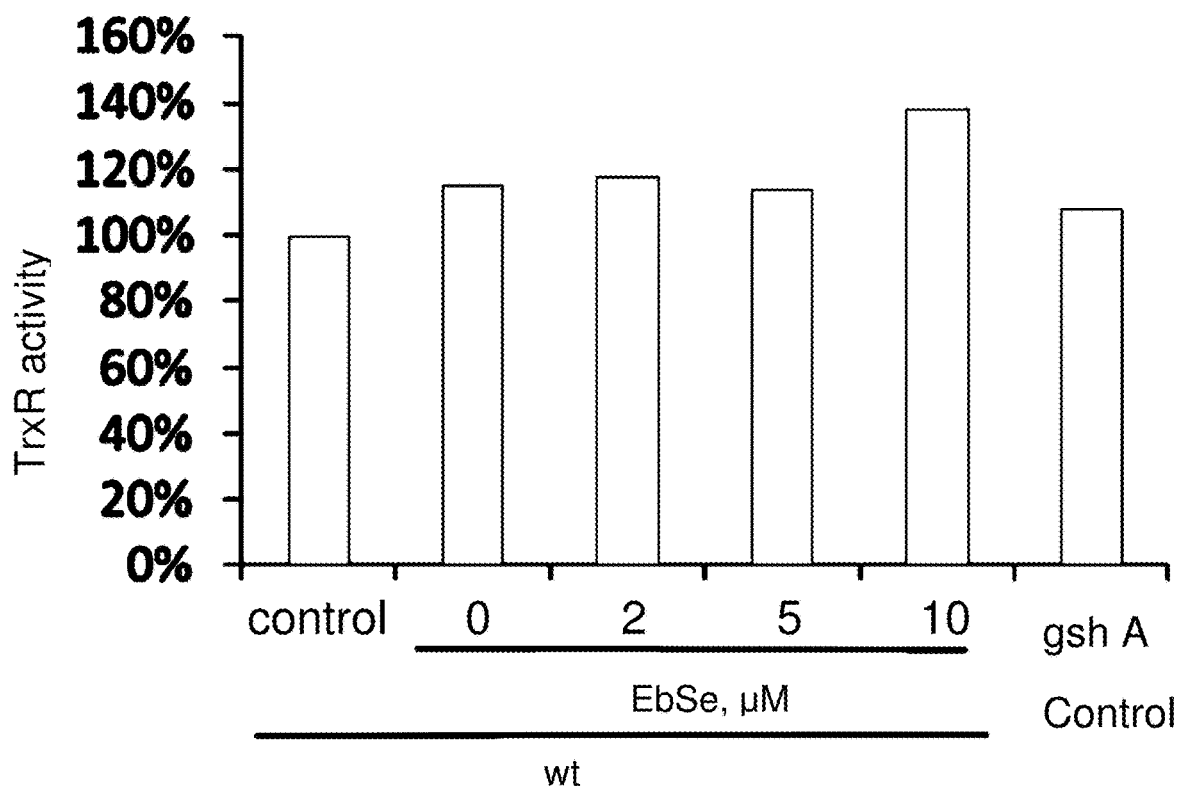
Figure 5C:
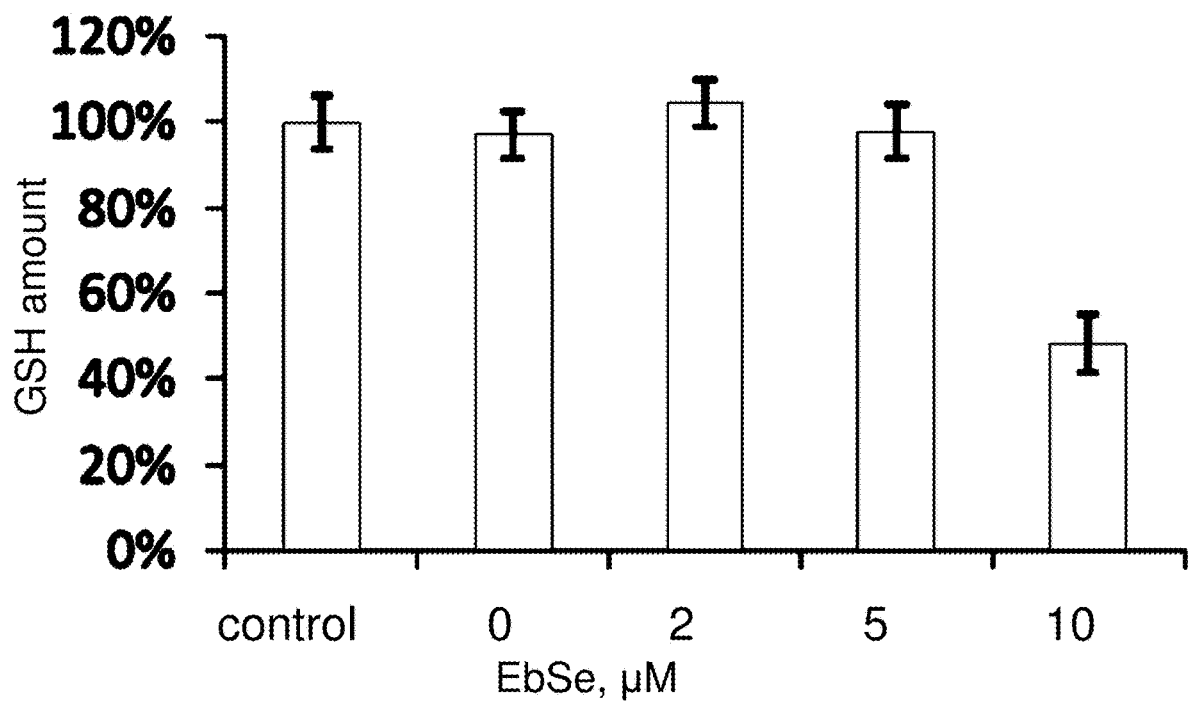
Figure 6:
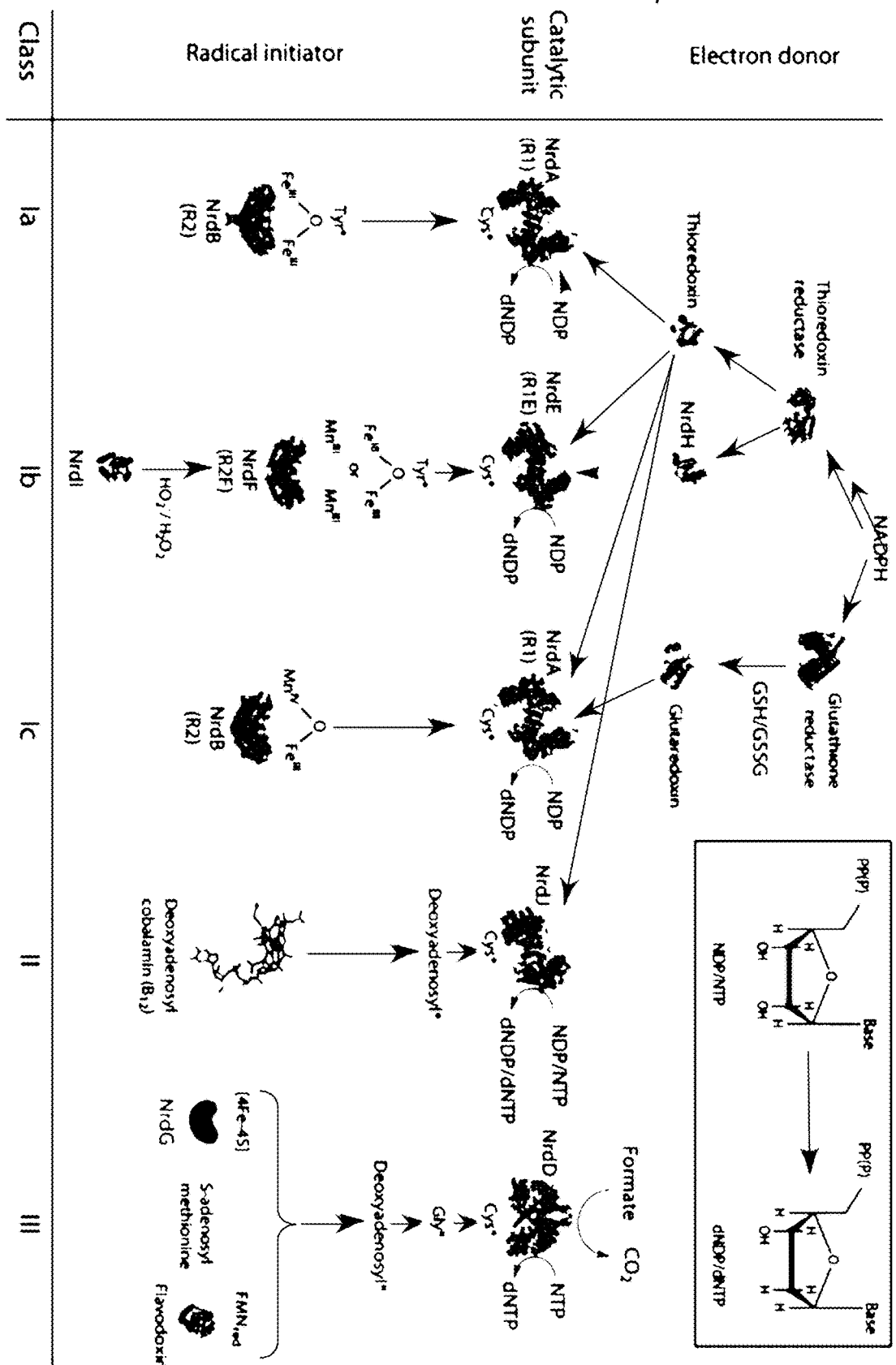
FIG. 6 shows ribonucleotide reductase (RNR) and electron transport pathways in bacteria.

FIGS. 5A-5C show the effects of combination treatment of silver and ebselen on the bacterial Trx and GSH systems. FIG. 5A shows the results from *E. coli* strains which were grown in LB medium till the absorbance around 0.3. Then the bacterial cells were treated with different combination of silver nitrate (5 µM) and varying ebselen for 1 h. The absorbance at 600 nm were measured to detect the growth of the bacteria. After that cells were harvested and sonicated to get cell lysates. FIG. 5B shows the effect of combination of silver and ebselen on the bacterial TrxR activity. *E. coli* TrxR activity was measured by insulin coupled reduction endpoint assay as described in material and methods. FIG. 5C shows the effect of combination of silver and ebselen on the bacterial GSH level. GSH amounts were measured as the description in material and methods.

Intriguingly, both gshA⁻ and trxA⁻ trxB⁻ trxC⁻ mutants are more sensitive to the combination treatment of ebselen and silver (FIGS. 4A-4F and FIG. 5A). In particular, for the gshA⁻ mutant, less than 1 µM silver inhibited the bacterial growth in the presence of 4 µM of ebselen. These results suggest that bacterial Trx and GSH systems are critical for the bacteria to defense against the combination treatment.

Furthermore, the effects of combination treatment of silver and ebselen on bacterial Trx and GSH were investigated. *E. coli* strains were cultured until the $OD_{600}$ got around to 0.4, and then the bacteria were treated with 5 µM silver and different concentrations of ebselen (2, 5, 10 µM). Ebselen at 10 µM inhibited the growth of wild type (wt) *E. coli*, whereas 2 µM ebselen inhibit the growth of *E. coli* gshA⁻ strain, which is consistent with above results (FIG. 5A). In the bacterial lysates, TrxR activity was not affected (FIG. 5B), which is probably due to the fact that inhibition of TrxR by ebselen in a reversible process. Interestingly, for the wt *E. coli*, bacteria were inhibited by the combination of 5 µM silver and 10 µM ebselen, and in the cell lysate, GSH amount was obviously lower than the others (FIG. 5C), indicating that the combination treatment causing GSH consumption is a key factor for the inhibition of bacterial growth and killing.

The combination of ebselen and silver ions results in a strong synergistic effect and killing of both *E. coli* and *B. subtilus* as a new antibiotic principle. Previously it was shown that gram-positive bacteria such as *S. aureus* were sensitive to ebselen and analogs because the essential thioredoxin system was targeted and these organisms that lack GSH and glutaredoxin. It is now shown that the gram-negative *E. coli* is highly sensitive to silver and ebselen in combination.

The foregoing disclosure of embodiments and exemplary applications of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

TABLE 1

Inhibition constants of ebselen derivates on *E. coli* TrxR, mammalian TrxR, *E. coli* growth, glutathione peroxidase activity and HEK 293T cells growth

| Compound Number | Structural Formula | IC$_{50}$ for *E. coli* TrxR (μM) | K$_i$ for *E. coli* TrxR (μM) | MIC for wild type DHB4 *E. coli* (μM) | MIC for gshA$^-$ DHB4 *E. coli* (μM) | MIC for Gor DHB4 *E. coli* (μM) | Relative GPx activity | IC$_{50}$ for recombinant rat TrxR (μM) | IG50 for HEK 293T (μM) |
|---|---|---|---|---|---|---|---|---|---|
| EbSe 2 | | 15 | Not detected 1.00 | | | | 0.97 | >10 | 95 |
| EbSe 3 | | 15 | Not detected | | | | 1.2 | >10 | 100 |
| EbSe 4 | | 15 | Not detected | | | | 1.1 | >10 | 75 |
| EbSe 5 | | 2.125 | 0.035 | | | | | | |
| EbSe 6 | | 6 | 0.30 | 40 | 26 | 15 | 1 | >10 | 120 |
| EbSe 7 | | 7 | 0.55 | 34 | 20 | 23 | 0.64 | >10 | 120 |
| EbSe 8 | | 6 | 0.25 | 47 | 13 | 24 | 0.67 | >10 | 80 |
| EbSe 9 | | 7.5 | 1.20 | 49 | 24 | 31 | 2.1 | 0.8 | >160 |
| EbSe 10 | | 15 | Not detected | | | | 1.8 | >10 | 55 |

TABLE 1-continued

Inhibition constants of ebselen derivates on *E. coli* TrxR, mammalian TrxR, *E. coli* growth, glutathione peroxidase activity and HEK 293T cells growth

| Compound Number | Structural Formula | IC$_{50}$ for *E. coli* TrxR (μM) | K$_i$ for *E. coli* TrxR (μM) | MIC for wild type DHB4 *E. coli* (μM) | MIC for gshA⁻ DHB4 *E. coli* (μM) | MIC for Gor DHB4 *E. coli* (μM) | Relative GPx activity | IC$_{50}$ for recombinant rat TrxR (μM) | IG50 for HEK 293T (μM) |
|---|---|---|---|---|---|---|---|---|---|
| EbSe 11 | | >40 | 0.3 Not detected | No Inhibition | No Inhibition | No Inhibition | 0.87 | >10 | >160 |
| EbSe 12 | | 3 | 0.25 | No Inhibition | No Inhibition | No Inhibition | 0.93 | >10 | 80 |
| EbSe 13 | | 3 | 1.5 | 45 | 21 | 24 | 1.4 | >10 | 60 |
| EbSe 14 | | 2 | 0.05 | 23 | 23 | 19 | No activity | 0.06 | 12.5 |
| EbSe 15 | | 2.1 | 008 (0.038 for the selenium released stock) | | | | | | 9.5 |
| EbSe 16 | | 2.25 | 0.025 (0.01 for the selenuim released stock) | 20 | 20 | 35 | | | 9.2 |
| EbSe19 | | 3 | 0.5 | | | | | | |
| EbSe 22 | | >10 | 7.5 | | | | | | |
| Dise1 | | >20 | No Inhibition | No Inhibition | No Inhibition | No Inhibition | | 2.1 | |
| 2 | | >10 | 7.5 | No Inhibition | No Inhibition | No Inhibition | | | 60 |

The invention claimed is:

1. A method for inhibiting growth of a prokaryotic organism, comprising administering to the prokaryotic organism a source of metal ions and at least one compound according to Formula I or a pharmaceutically acceptable salt thereof, in an amount of at least 1 mg:

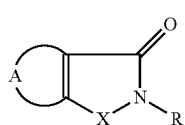

wherein X is selenium or sulfur,
wherein A represents a saturated, unsaturated or polyunsaturated 3 to 6 member carbon chain,
wherein N may optionally substitute for one or more carbons, and which is optionally substituted with one or more of OR, SR, alkylamino, $C_1$-$C_5$ alkyl, OH, alkoxyl, SH, $NH_2$, N-alkylamino, N,N-dialkylamino, COOH, CHO, $NO_2$, F, Cl, Br, and I, and
wherein R is independently selected from the group consisting of:
H,
alkyl having a carbon chain of 1 to 14 carbon atoms wherein the carbon chain is branched or unbranched which is optionally substituted with bensisoselenazol-3(2H)-one-2-yl, bensisotiazol-3(2H)-one-2-yl, OH, alkoxyl, SH, $NH_2$, N-alkylamino, N,N-dialkylamino, COOH, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, I, and heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I, and
heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
wherein the at least one compound according to Formula I or the pharmaceutically acceptable salt is effective as an inhibitor of prokaryotic thioredoxin reductase having an $IC_{50}$ of less than about 25 μM; and
an effective amount of a water soluble source of at least one metal ion, comprising at least 1 mg of the water soluble source of at least one metal ion, to achieve a dose-dependent reduction of at least 33% in the inhibitory concentration ($IC_{50}$) for *E. coli* thioredoxin reductase of the at least one compound according to Formula I or the pharmaceutically acceptable salt thereof in the absence of the water soluble source of the at least one metal ion,
wherein the water soluble source of the at least one metal ion comprises a water soluble source of metal ions which releases the metal ions for an extended duration at a constant rate.

2. The method according to claim 1, wherein the water soluble source of metal ions and the at least one compound according to Formula I or the pharmaceutically acceptable salt thereof, are together in unit dosage form, comprising a therapeutically effective amount of between 1 mg and 1000 mg of the at least one compound of Formula I or the pharmaceutically acceptable salt thereof, and a therapeutically effective amount of between 1 mg and 100 mg of a silver salt comprising the metal ion.

3. The method according to claim 1, wherein X is selenium.

4. The method according to claim 1, wherein Formula I is selected from the group consisting of ebselen and ebsulfur-23.

5. The method according to claim 1, wherein the water soluble source of metal ions and the at least one compound according to Formula I or a pharmaceutically acceptable salt thereof are administered to an animal or human to treat an infection of the animal or human.

6. A method for inhibiting growth of a prokaryotic organism, comprising exposing the prokaryotic organism to:
(a) at least one compound according to Formula I or a pharmaceutically acceptable salt thereof, which is effective as an inhibitor of prokaryotic thioredoxin reductase having an $IC_{50}$ of less than about 25 μM:

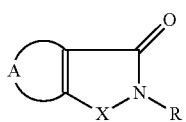

wherein X is selenium or sulfur,
wherein A represents a saturated, unsaturated or polyunsaturated 3 to 6 member carbon chain,
wherein N may optionally substitute for one or more carbons, and which is optionally substituted with one or more of OR, SR, alkylamino, $C_1$-$C_5$ alkyl, OH, alkoxyl, SH, $NH_2$, N-alkylamino, N,N-dialkylamino, COOH, CHO, $NO_2$, F, Cl, Br, and I, and
wherein R is independently selected from the group consisting of:
H,
alkyl having a carbon chain of 1 to 14 carbon atoms wherein the carbon chain is branched or unbranched which is optionally substituted with bensisoselenazol-3(2H)-one-2-yl, bensisotiazol-3(2H)-one-2-yl, OH, alkoxyl, SH, $NH_2$, N-alkylamino, N,N-dialkylamino, COOH, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, I, and heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I; and
(b) at least one water soluble source of metal ions in an amount of at least 1 mg of the water soluble source of metal ions, effective to achieve a dose-dependent reduction of at least 33% in the inhibitory concentration ($IC_{50}$) for *E. coli* thioredoxin reductase with respect to the at least one compound according to Formula I or pharmaceutically acceptable salt thereof absent of the water soluble source of the at least one metal ion, wherein the water soluble source of metal ions comprises a water soluble source of metal ions which releases the metal ions for an extended duration at a constant rate.

7. The method according to claim 6, wherein the method provides a treatment of infection by the prokaryotic organism causing an infection in an animal or human, said exposing comprising administering a pharmaceutically acceptable unit dosage form comprising both the at least one compound of Formula I or a pharmaceutically acceptable salt thereof and the at least one water soluble source of metal ions to an animal or human having the infection by the prokaryotic organism, wherein:
the at least one compound of Formula I or a pharmaceutically acceptable salt thereof is present in a therapeutically effective amount of between 1 mg and 1000 mg, and
the water soluble source of metal ions comprises a water soluble source of silver ions, and is present in a therapeutically effective amount of between 1 mg and 100 mg.

8. The method according to claim 6, wherein X is selenium.

9. The method according to claim 6, wherein Formula I is ebselen.

10. The method according to claim 6, wherein Formula I is ebsulfur-23.

11. A method for inhibiting growth of a prokaryotic organism, comprising co-administering to an environment of the prokaryotic organism:

(a) at least one compound selected from the group consisting of Formula I and a pharmaceutically acceptable salt thereof:

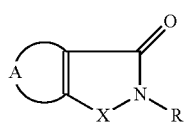

(I)

wherein X is selenium or sulfur,
wherein A represents a saturated, unsaturated or polyunsaturated 3 to 6 member carbon chain,
wherein N may optionally substitute for one or more carbons, and which is optionally substituted with one or more of OR, SR, and alkylamino, $C_1$-$C_5$ alkyl, OH, alkoxyl, SH, $NH_2$, N-alkylamin-o, N,N-dialkylamino, COOH, CHO, $NO_2$, F, Cl, Br, and I, and
wherein R is independently selected from the group consisting of:
H,
alkyl having a carbon chain of 1 to 14 carbon atoms wherein the carbon chain is branched or unbranched which is optionally substituted with bensisoselenazol-3(2H)-one-2-yl, bensisotiazol-3(2H)-one-2-yl, OH, alkoxyl, SH, $NH_2$, N-alkylamino, N,N-dialkylamino, COOH, aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, I, and heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
aryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
heteroaryl which is optionally substituted with $C_1$-$C_5$ alkyl, OH, alkoxyl, SH, $NH_2$, N-alkylamino, N,N-dialkylamino, COOH, CHO, $NO_2$, F, Cl, Br, and I,
effective as a selective prokaryotic thioredoxin reductase inhibitor having a 50% inhibitory concentration ($IC_{50}$) of less than about 25 µM for E. coli thioredoxin reductase; and (b) an effective amount of a water soluble source of at least one metal ion, to achieve a dose-dependent reduction of at least 33% in the inhibitory concentration ($IC_{50}$) for E. coli thioredoxin reductase of the at least one compound selected from the group consisting of Formula I and the pharmaceutically acceptable salt thereof, in the absence of the water soluble source of the at least one metal ion,
wherein the water soluble source of the at least one metal ion comprises a water soluble source of metal ions which releases the metal ions for an extended duration at a constant rate.

12. The method according to claim 11, wherein the at least one compound according to Formula I is a benzoisoselenazol.

13. The method according to claim 11, wherein the at least one compound according to Formula I is a benzoisothiazol.

14. The method according to claim 13, wherein the benzoisothiazol comprises ebsulfur-23.

15. The method according to claim 11, wherein the effective amount of the water soluble source of the at least at least one metal ion comprises a metal salt or a metal complex of the at least one compound selected from the group consisting of Formula I and the pharmaceutically acceptable salt thereof.

16. The method according to claim 11, wherein water soluble source of the at least one metal ion is selected from the group consisting of one or more of a silver salt, a silver colloid, and an organo-silver complex.

17. The method according to claim 11, wherein the at least one compound selected from the group consisting of Formula I and the pharmaceutically acceptable salt thereof, acts synergistically with the at least one metal ion with respect to an inhibition of prokaryotic thioredoxin reductase.

18. The method according to claim 11, further comprising:
obtaining a microbiological sample from a patient comprising the prokaryotic organism; and
determining a sensitivity of the prokaryotic organism to a range of pharmaceutically acceptable treatments, each treatment comprising administration of at least one compound selected from the group consisting of Formula I and the pharmaceutically acceptable salt thereof, and the water soluble source of the at least one metal ion.

19. The method according to claim 18, further comprising adjusting a treatment of the patient to achieve inhibition of growth of the prokaryotic organism, based on the determined sensitivity.

* * * * *